United States Patent
Brader

(10) Patent No.: US 6,531,448 B1
(45) Date of Patent: Mar. 11, 2003

(54) INSOLUBLE COMPOSITIONS FOR CONTROLLING BLOOD GLUCOSE

(75) Inventor: Mark Laurence Brader, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/217,275

(22) Filed: Dec. 21, 1998

Related U.S. Application Data

(60) Provisional application No. 60/068,601, filed on Dec. 23, 1997, provisional application No. 60/088,859, filed on Jun. 11, 1998, and provisional application No. 60/109,940, filed on Nov. 25, 1998.

(51) Int. Cl.$^7$ ............................ A61K 38/28; C07K 7/00
(52) U.S. Cl. ............................. 514/3; 514/4; 514/314; 424/491; 530/303; 530/304; 530/345
(58) Field of Search ................................ 530/303, 304, 530/345; 514/314, 317; 424/491

(56) References Cited

U.S. PATENT DOCUMENTS

| | | | |
|---|---|---|---|
| 2,538,018 A | 1/1951 | Krayenbuhl et al. | 167/75 |
| 2,801,953 A | 8/1957 | Dorzbach et al. | 167/75 |
| 2,849,370 A | 8/1958 | Petersen et al. | 167/75 |
| 3,060,093 A | 10/1962 | Poulsen et al. | 167/75 |
| 3,102,077 A | 8/1963 | Christensen et al. | 167/75 |
| 3,684,791 A | 8/1972 | Geiger et al. | 260/112.7 |
| 3,864,325 A | 2/1975 | Smyth | 260/112.7 |
| 3,868,356 A | 2/1975 | Smyth | 260/112.7 |
| 3,868,358 A | 2/1975 | Jackson | 260/112.7 |
| 3,869,437 A | 3/1975 | Lindsay | 260/112.7 |
| 3,907,763 A | 9/1975 | Brandenberg et al. | 260/112.7 |
| 3,950,517 A | 4/1976 | Lindsay | 424/178 |
| 4,183,849 A | 1/1980 | Hansen et al. | 260/112.7 |
| 4,343,898 A | 8/1982 | Markussen | 435/71 |
| 4,400,465 A | 8/1983 | Morihara | 435/71 |
| 4,401,757 A | 8/1983 | Morihara | 435/71 |
| 4,489,159 A | 12/1984 | Markussen | 435/71 |
| 4,601,852 A | 7/1986 | Obermeier et al. | 530/303 |
| 4,601,979 A | 7/1986 | Andresen et al. | 435/70 |
| 4,608,364 A | 8/1986 | Grau | 514/4 |
| 4,959,351 A | 9/1990 | Grau | 514/4 |
| 5,028,587 A | 7/1991 | Dorschug et al. | 514/3 |
| 5,149,777 A | 9/1992 | Hansen et al. | 530/303 |
| 5,164,366 A | 11/1992 | Balschmidt et al. | 514/3 |
| 5,430,016 A | 7/1995 | Balschmidt et al. | 514/4 |
| 5,461,031 A | 10/1995 | DeFelippis | 514/4 |
| 5,474,978 A | 12/1995 | Bakaysa et al. | 514/4 |
| 5,514,646 A | 5/1996 | Chance et al. | 514/3 |
| 5,547,930 A | 8/1996 | Balschmidt | 514/3 |
| 5,618,913 A | 4/1997 | Brange et al. | 530/303 |
| 5,650,486 A | 7/1997 | DeFelippis | 530/305 |
| 5,700,904 A | 12/1997 | Baker et al. | 530/305 |
| 5,747,642 A | 5/1998 | DeFelippis | 530/304 |
| 5,834,422 A | 11/1998 | Baischmidt | 514/3 |
| 5,898,028 A | 4/1999 | Jensen et al. | 514/4 |
| 5,948,751 A | 9/1999 | Kimer et al. | 514/4 |
| 6,051,551 A | 4/2000 | Hughes et al. | 514/3 |
| 6,127,334 A | 10/2000 | Kimer et al. | 514/3 |
| 6,268,335 B1 | 7/2001 | Brader | 514/3 |
| 6,335,316 B1 | 1/2002 | Hughes et al. | 514/3 |

FOREIGN PATENT DOCUMENTS

| | | |
|---|---|---|
| EP | 0214826 | 3/1987 |
| EP | 0375437 | 6/1990 |
| EP | 0383472 | 8/1990 |
| EP | 0709395 | 5/1996 |
| EP | 0861851 | 9/1998 |
| JP | 1-254699 | 10/1989 |
| WO | 90/07522 | 7/1990 |
| WO | 95/00550 | 1/1995 |
| WO | 95/07931 | 3/1995 |
| WO | 96/29344 | 9/1996 |
| WO | 97/47312 | 12/1997 |
| WO | WO 97/48413 | 12/1997 |
| WO | 98/34953 | 8/1998 |

OTHER PUBLICATIONS

Scott and Fisher, *j. Pharmacol. Exp. Ther.*, 58:78 (1936).

Hagedorn, et al., *J. Am. Med. Assn.*, 106:177–180 (1936).

Krayenbühl and Rosenberg, *Rep. Steno. Mem. Hosp. Nor. Insulinlab.*, 1:60 (1946).

Harding, et al., "The Crystal Structure of Insulin: II. An Investigation of Rhombohedral Zinc Insulin Crystals and a Report of other Crystalline Forms," *J. Mol. Biol.*, 16:212–226 (1966).

Wallhausser, K–H, "Antimicrobial Preservatives in Europe," *Int'l. Sympos. Preservatives in Biological Products*, San Francisco, vol. 24:9–28 (S. Karger, Basel, 1974).

Low, B.W., et al., "Insulin/Proinsulin, a New Crystalline Complex," *Nature*, 248:339–340 (1974).

(List continued on next page.)

*Primary Examiner*—Bennett Celsa
(74) *Attorney, Agent, or Firm*—Grant E. Reed; James J. Kelley; Lynn D. Apelgren

(57) ABSTRACT

The present invention relates to insoluble compositions comprising a protein selected from the group consisting of insulin, insulin analogs, and proinsulins; a derivatized protein selected from the group consisting of derivatized insulin, derivatized insulin analog, and derivatized proinsulin; a complexing compound; a hexamer-stabilizing compound; and a divalent metal cation. Formulations of the insoluble composition are suitable for both parenteral and non-parenteral delivery for treating hyperglycemia and diabetes. Microcrystal forms of the insoluble precipitate are pharmaceutically analogous to the neutral protamine Hagedorn (NPH) insulin crystal form. Surprisingly, it has been discovered that suspension formulations of such insoluble compositions possess unique and controllable dissolution properties that provide therapeutically advantageous glucodynamics compared with insulin NPH formulations.

47 Claims, 4 Drawing Sheets

OTHER PUBLICATIONS

Chance, R.E., et al., "The Production of Human Insulin using Recombinant DNA Technology and a New Chain Combination Procedure," *Peptides: Synthesis, Structure, Function, Proceedings of 7th American Peptide Symposium*, Rick, D.H. and Gross, E., Eds., Pierce Chemical Company (1981).

Derewenda, et al., *Nature*, 338:13,594–596 (Apr. 1989).

Dodson, et al., *Phil Trans. R. Soc. Lond. A*, 345, 153–164 (1993).

Myers, S.R., et al., "Acylation of Human Insulin with Palmitic Acid Extends the Time Action of Human Insulin in Diabetic Dogs," *Diabetes*, 46:637–642 (1997).

Whittingham, J.L., et al., *Biochemistry* 36:2826–2831 (1997).

Whittingham, J.L., et al., *Biochemistry* 37:11516–11523 (1998).

DeFelippis, M.R., et al., Preparation and Characterization of a Cocrystalline Suspension of [LysB28, ProB29] –Human Insulin Analog, *J. Phrarmaceut. Sci.*, 87:170–176 (1998).

Hashimoto, M., et al., "Synthesis of palmitoyl derivatives of insulin and their biological activities," *Pharmaceut. Res.* 6:171 (1989).

Steiner, D.F., "Cocrystallization of proinsulin and insulin," *Nature* 243:528–530 (1973).

Simkin, R.D., et al., "Precipitation and Crystallization of Insulin in the Presence of Lysozyme and Salmine," *Biochem. Biophys. Acta*, 200:385–394 (1970).

Galloway, John A., et al., "Mixtures of Intermediate–Acting Insulin (NPH and Lente) with Regular Insulin: An Update," *Insulin Update: 1992, Proceedings of a Symposium*, Key Biscayne, *Florida, Dec. 5–7, 1981*, Excerpta Medica, Princeton, N.J. (1982).

Chen, Ing–Jun, et al., "Application of Mugiline β to the Preparation of Isophane Insulin," *Proc. Natl. Sci. Counc. ROC(A)*, vol. 6, No. 3, 185–189 (1982).

Fullerton, W. Wardle, et al., "Insulin Crystallization in the Presence of Basic Proteins and Peptides," *Biochim. Biophys. Acta*, 214:141–147 (1970).

Kurtzhals, P. et al., "Albumin Binding and Time Action of Acyalted Insulins in Various Species," *J. Pharm. Sci. 85: 304–308* (Mar., 1996), Amerian Chemical Society and American Pharmaceutical Association, Washington, DC.

Markussen, J. et al., "Soluble, fatty acid acylted insulins bind to albumin and show protracted action in pigs," *Diabetologia 39*: 2821–288 (Mar., 1996), Springer–Verlag, New York, NY).

Claims for U.S. Application No. 09/761,903 (Claims 110–162).

Claims for U.S. Application No. 10/010,038 (Claims 85–118).

INSOLUBLE COMPOSITIONS FOR CONTROLLING BLOOD GLUCOSE

This Application claims benefit to Ser. No. 60/068,601 (Dec. 23, 1997) Ser. No. 60/088,859 (Jun. 11, 1998) Ser. No. 60/109,940 (Nov. 25, 1998)

BACKGROUND OF THE INVENTION

1. Field of the Invention

This invention is in the field of human medicine. More particularly, this invention is in the field of pharmaceutical treatment of the diseases of diabetes and hyperglycemia.

2. Description of Related Art

It has long been a goal of insulin therapy to mimic the pattern of endogenous insulin secretion in normal individuals. The daily physiological demand for insulin fluctuates and can be separated into two phases: (a) the absorptive phase requiring a pulse of insulin to dispose of the meal-related blood glucose surge, and (b) the post-absorptive phase requiring a sustained delivery of insulin to regulate hepatic glucose output for maintaining optimal fasting blood glucose.

Accordingly, effective therapy for people with diabetes generally involves the combined use of two types of exogenous insulin formulations: a rapid acting meal time insulin provided by bolus injections and a long-acting, so-called, basal insulin, administered by injection once or twice daily to control blood glucose levels between meals. An ideal basal insulin will provide an extended and "flat" time action—that is, it will control blood glucose levels for at least 12 hours, and preferably for 24 hours or more, without significant risk of hypoglycemia. Furthermore, an ideal basal insulin should be mixable with a soluble meal-time insulin, and should not cause irritation or reaction at the site of administration. Finally, basal insulin preparations that are suspension formulations should be able to be readily, and uniformly resuspended by the patient prior to administration.

As is well understood by those skilled in this art, long-acting insulin formulations have been obtained by formulating normal insulin as microcrystalline suspensions for subcutaneous injection. Examples of commercial basal insulin preparations include NPH (Neutral Protamine Hagedorn) insulin, protamine zinc insulin (PZI), and ultralente (UL).

Early versions of present-day commercial NPH insulin that contained a surplus of protamine were developed in the 1930's by Scott, et al. [*J. Pharmacol. Exp. Ther.* 58:78, et seq. (1936)] and Hagedorn, et al. [*J. Am. Med. Assoc.* 106:177–180 (1936)]. In 1946, NPH insulin having isophane proportions of insulin and protamine, together with zinc, were developed by Krayenbuhl, et al. [*Rep. Steno Mem. Hosp. Nord. Insulinlab.* 1:60, et seq. (1946)]. These workers found that when insulin and protamine were combined in so-called isophane proportions at a neutral pH, in the presence of zinc and a phenolic compound, that an amorphous precipitate formed, and that upon standing the amorphous precipitate was transformed into oblong, tetragonal crystals having pyramidal shaped ends. These crystals have been described as rod-like. The isophane ratio of insulin and protamine sulfate is observed to be about 0.09 mg of protamine sulfate per mg of insulin. Zinc is needed in an amount of at least about 3.5 $\mu$g per mg of insulin, and a phenolic compound at a concentration higher than about 0.1%.

Insulin NPH is the most widely-used insulin preparation, constituting from 50 to 70 per cent of the insulin used worldwide. It is a suspension of a microcrystalline complex of insulin, zinc, protamine, and one or more phenolic preservatives. NPH insulin preparations are commercially available incorporating human insulin, pork insulin, beef insulin, or mixtures thereof. Also, NPH-like preparations of a monomeric insulin analog, LysB298, ProB29-human insulin analog, are known in the art [abbreviated herein as "NPL": De Felippis, M. R., U.S. Pat. No. 5,461,031, issued Oct. 24, 1995; De Felippis, M. R., U.S. Pat. No. 5,650,486, issued Jul. 22, 1997; and De Felippis, M. R., U.S. Pat. No. 5,747,642, issued May 5, 1998]. It is widely accepted that insulin NPH provides extended control of blood glucose compared with regular insulin because insulin must first dissolve from the insulin NPH microcrystals before it can be absorbed. With regular insulin, there is no dissolution needed prior to absorption. For insulin NPH, dissolution is the rate-controlling step in determining the pharmacodynamics and pharmacokinetics.

NPH insulin microcrystals possess a distinctive rod-shaped morphology of typical dimensions about 5 microns long by 1 micron thick and 1 micron wide. The extended duration of action of NPH insulin microcrystals results from their slow absorption from the subcutaneous injection site.

Therapy using currently-available NPH insulin preparations fails to provide the ideal "flat" pharmacokinetics necessary to maintain optimal fasting blood glucose for an extended period of time between meals. Consequently, treatment with NPH insulin can result in undesirably high levels of insulin in the blood, which may cause life-threatening hypoglycemia.

In addition to failing to provide an ideal flat pharmacokinetic profile, the duration of action of NPH insulin also is not ideal. In particular, a major problem with NPH therapy is the "dawn phenomenon" which is hyperglycemia that results from the loss of effective glucose control overnight while the patient is sleeping. These deficiencies in glycemic control contribute to serious long-term medical complications of diabetes and impose considerable inconvenience and quality-of-life disadvantages to the patient.

Protamine zinc insulin (PZI) has a composition similar to NPH, but contains higher levels of protamine and zinc than NPH. PZI preparations may be made as intermediate-acting amorphous precipitates or long-acting crystalline material. PZI, however, is not an ideal basal insulin pharmaceutical because it is not mixable with a soluble meal-time insulin, and the high zinc and protamine can cause irritation or reaction at the site of administration.

Human insulin ultralente is a microcrystalline preparation of insulin having higher levels of zinc than NPH, and not having either protamine or a phenolic preservative incorporated into the microcrystal. Human ultralente preparations provide moderate time action that is not suitably flat, and they do not form stable mixtures with insulin. Furthermore, they are difficult to resuspend.

There have been attempts to address the perceived inadequacies of known insulin suspensions. Fatty acid-acylated insulins have been investigated for basal control of blood glucose [Havelund, S., et al., WIPO publication WO95/07931, Mar. 23, 1995]. Their extended time action is caused by binding of the fatty acyl portion of these molecules to serum albumin. The fatty acyl chain lengths of these molecules is such as to take advantage of the fatty acid binding capability of serum albumin. The fatty acid chains used in fatty acid-acylated insulins are typically longer than about ten carbon atoms, and chain lengths of fourteen and sixteen carbon atoms are optimal for binding to serum albumin and extending time action.

Unlike NPH insulin, which is insoluble, the aforementioned fatty acid-acylated insulins are soluble at the usual therapeutic concentrations of insulin. However, the time action of these preparations may not be sufficiently long enough, or flat enough, to provide ideal basal control, and they are less potent than insulin, thereby requiring administration of greater amounts of the drug agent [Radziuk, J., et al., *Diabetologia* 41:116–120, 489–490 (1998)].

Whittingham, J. L., et al. [*Biochemistry* 36:2826–2831 (1997)] crystallized B29-Nε-tetradecanoyl-des(B30)-human insulin analog as a hexamer complex with zinc and phenol for the purpose of structural studies by X-ray crystallography. The hexamer was found to be in the R6 conformation, and to have certain properties different from hexamers of human insulin. Whittingham, et al. do not disclose any pharmaceutical or pharmacological properties of the crystal that was formed, nor do they suggest that such a crystal would have any advantageous properties for treating diabetes or hyperglycemia. It is not possible to predict from Whittingham, et al. whether protamine-containing crystals of the NPH type could be formed with derivatized insulins and insulin analogs, or what the pharmacokinetics or pharmacodynamic response of such crystals would be.

Thus, there remains a need to identify insulin preparations that have flatter and longer time action than NPH insulin, that are mixable with soluble, meal-time insulins, that can be readily resuspended, and that do not pose risk of irritation or reaction at the site of administration. I discovered quite surprisingly that these properties are provided by insoluble compositions that include a derivatized protein, an un-derivatized protein, zinc, protamine, and a phenolic preservative. In addition to the properties mentioned above, the insoluble compositions provide flexibility of control over the duration and shape of the glucodynamic response profile. They are thought to function as controlled release compositions, wherein the release rate is controlled by the proportion and nature of the derivatized protein. Thus, one aspect of the present invention is an insoluble composition comprising an un-derivatized protein, a derivatized protein, a complexing compound, a hexamer-stabilizing compound, and a divalent metal cation. Other aspects of this invention that relate to the preparation, formulation, and use of such compositions will be discussed herein.

There are no examples known to me of mixtures of derivatized and un-derivatized insulins, as those terms are to be understood in the context of the present disclosure. Crystals comprised of proinsulin and insulin [Steiner, D. F., *Nature* 243:528–530 (1973); Low, B. W., et al., *Nature* 248:339–340 (1974)] and crystals comprised of a insulin or an insulin analog having approximately the same isoelectric point as insulin and an insulin analog having additional basic amino acids [Dorschug, M., et al., U.S. Pat. No. 5,028,587, issued Jul. 2, 1991] are known.

Steiner produced crystals comprised of proinsulin and insulin with mole ratios of about 1:11, 1:5, 1:2, and 1:1, respectively (i.e., 0.5, 1, 2, and 3 moles of proinsulin per 6 moles total insulin and proinsulin) in 0.095 M sodium citrate, pH 6.0, 0.03 M NaCl, 0.012 M ZnCl2, and 16% acetone., The proportion of proinsulin greatly affected the rate of crystallization. The crystals differed greatly from those of pure insulin under the same conditions, and were characterized as rhombohedral crystals with rounded borders. There was great variability within and between preparations. The utility ascribed to crystallizing proinsulin and insulin was that it facilitated isolating small amounts of proinsulin and related structures from pancreatic extracts. The author speculated that crystallization may occur between precursor and product peptides, and among other closely related proteins.

Low, B. W., et al. produced very large crystals comprised of equimolar proportions of beef or pork insulin and their respective proinsulins, wherein the proinsulin and insulin were formed into homogenous hexamers prior to crystallization. Analysis by X-ray crystallography and quantitative electrophoresis supported a conclusion that the unit cell in the crystals was formed of twelve insulin hexamers and twelve proinsulin hexamers. It was specifically stated that no studies were known to suggest that insulin and proinsulin form mixed dimers and hexamers in solution.

Dörschug, M., et al. disclosed crystals comprised of insulin, des(PheB1) insulin, des(ThrB30) human insulin, or des(AlaB30) beef insulin, and at least one insulin having a basic modification at the C-terminal end of the B chain ("modified insulin"). Such modified insulins are disclosed, for example, in European Patent Application No. 132,769. Globin or protamine sulfate were stated to be auxiliary compounds that could be used in the crystal preparations. There are no examples of the use of protamine, nor any suggestion that the inventors appreciated the effect of adding such compounds. Furthermore, the modified insulins used in Dorschug, et al. are different than the derivatives used in the present invention.

As mentioned above, I have unexpectedly observed that when a protein selected from insulin, an insulin analog, and proinsulin is made less soluble in an aqueous solvent or more lipophilic by derivatizing one or more of its reactive side groups, the derivatized protein and an un-derivatized protein selected from insulin, an insulin analog, and proinsulin can be incorporated into insoluble precipitates and into NPH-like crystals with protamine. When such proteins are jointly precipitated or crystallized to form insoluble compositions, the rate at which the proteins dissolve from the insoluble composition is greatly reduced compared with the rate at which physically similar insoluble compositions comprised of un-derivatized protein dissolve.

I have furthermore discovered that both amorphous precipitates and microcrystals comprised of derivatized protein, protein, a complexing compound, a divalent metal cation, and a hexamer-stabilizing compound provide flatter and longer time action than do physically similar microcrystals comprised solely of un-derivatized protein. Additionally, I have surprisingly discovered that the benefits of flatter and longer time action can be obtained even from amorphous precipitates comprised of one of the proteins and a derivatized protein.

SUMMARY OF THE INVENTION

Accordingly, in its broadest aspect, the present invention provides insoluble compositions comprising a derivatized protein selected from the group consisting of insulin derivatives, insulin analog derivatives, and proinsulin derivatives, a protein selected from the group consisting of insulin, insulin analogs, and proinsulins, a complexing compound, a hexamer-stabilizing compound, and a divalent metal cation. The derivatized protein is either less soluble in an aqueous solvent than is the un-derivatized protein, is more lipophilic than un-derivatized insulin, or produces a complex with zinc and protamine that is less soluble than the corresponding complex with the un-derivatized protein. The insoluble compositions of the present invention may be in the form of amorphous precipitates, or more preferably, in the form of microcrystals. The microcrystals may be either rod-shaped or irregular in morphology. These insoluble compositions are useful for treating diabetes and hyperglycemia, and provide the advantages of having flatter and longer time action than NPH insulin. The insoluble compositions are mixable in a formulation with soluble protein or with soluble derivatized protein, or both. Furthermore, by varying the ratio between protein and derivatized protein, the extent of protraction of the time action can be finely controlled over a very great range of time-action, from that nearly the same as NPH insulin to much greater than that of NPH insulin.

More specifically, the present invention provides insoluble compositions of proteins and fatty acid-acylated proteins that are useful for treating diabetes and hyperglycemia. These compositions are comprised of fatty acid-acylated protein selected from the group consisting of fatty acid-acylated insulin, fatty acid-acylated insulin analog, and fatty acid-acylated proinsulin, protein selected from the group consisting of insulin, insulin analogs, and proinsulin, protamine, a phenolic preservative, and zinc. The present invention is distinct from previous fatty acid-acylated insulin technology in that the extension of time action of the present invention does not rely necessarily on albumin-binding, though albumin binding may further protract the time action of certain of the compositions of the present invention.

The invention provides a microcrystal comprising a protein selected from the group consisting of insulin, insulin analog, and proinsulin, a derivatized protein selected from the group consisting of derivatized insulin, derivatized insulin analog, and derivatized proinsulin, a complexing compound a divalent metal cation, and a hexamer-stabilizing compound. The microcrystals of the present invention are useful for treating diabetes and for controlling blood glucose in a patient in need thereof.

The invention provides an amorphous precipitate comprising a protein selected from the group consisting of insulin, insulin analog, and proinsulin; a derivatized protein selected from the group consisting of derivatized insulin, derivatized insulin analog, and derivatized proinsulin, a complexing compound a divalent metal cation, and a hexamer-stabilizing compound. The amorphous precipitates of the present invention are useful for treating diabetes and for controlling blood glucose in a patient in need thereof. They are also useful as intermediates in the formation of the microcrystals of the present invention.

The invention provides aqueous suspension formulations comprising an insoluble composition and an aqueous solvent. One such aqueous suspension formulation is comprised of a microcrystalline composition of the present invention and an aqueous solvent. Another such aqueous suspension formulation comprises an amorphous precipitate of the present invention and an aqueous solvent. The soluble, aqueous phase of the present suspension formulations may optionally be comprised of a protein, such as human insulin, or a soluble analog of human insulin, such as a monomeric insulin analog, that control blood glucose immediately following a meal, and may additionally or alternatively be comprised of a derivatized protein. The formulations of the present invention have superior pharmacodynamics compared with human insulin NPH, and their time-action can be purposefully selected over a wide range, from just slightly extended compared with human insulin NPH to very greatly extended compared with human insulin NPH.

The invention also provides processes for preparing hybrid hexamers, mixed hexamers, the amorphous precipitates, and the co-crystals of the present invention, The invention provides a method of treating diabetes or hyperglycemia comprising, administering to a patient in need thereof a sufficient quantity of an insoluble composition of the present invention to regulate blood glucose levels in the patient.

The invention includes hybrid hexamer compositions comprising a protein selected from the group consisting of insulin, insulin analog, and proinsulin; a derivatized protein selected from the group consisting of derivatized insulin, derivatized insulin analogs, and derivatized proinsulins, and zinc. The hybrid hexamers of the present invention are useful for treating diabetes and for controlling blood glucose in a patient in need thereof. They are also useful as intermediates in the formation of the insoluble compositions of the present invention, which are themselves useful for treating diabetes and for controlling blood glucose in a patient in need thereof. Hybrid hexamers are believed to be formed when a protein and a derivatized protein are first mixed together under conditions that strongly favor dissolution into lower states of aggregation than the hexameric state, and second, the conditions are changed to strongly favor the hexameric aggregation state.

The invention includes mixed hexamer compositions, comprised zinc hexamers of a protein selected from the group consisting of insulin, an insulin analog, or proinsulin and zinc hexamers of a derivatized protein selected from the group consisting of a derivatized insulin, derivatized insulin analog, or a derivatized proinsulin. The mixed hexamers of the present invention are useful for treating diabetes and for controlling blood glucose in a patient in need thereof. They are also useful as intermediates in the formation of the insoluble compositions of the present invention, which are themselves useful for treating diabetes and for controlling blood glucose in a patient in need thereof. Mixed hexamers are believed to be formed when a protein and a derivatized protein are first separately dissolved under conditions that favor the hexameric aggregation state, and then are mixed together under conditions that continue to strongly favor the hexameric aggregation state.

The invention includes the use of an insoluble composition of the present invention to prepare a medicament for the treatment of diabetes or hyperglycemia.

BRIEF DESCRIPTION OF THE INVENTION

FIG. 1 depicts the dissolution over a five-hour period of co-crystals of the present invention having ratios of human insulin to B29-Nε-octanoyl-human insulin of 3:1 (- - -), 1:1 (———), and 1:3 (■■■), compared with the dissolution of a preparation of human insulin-protamine crystals (----).

FIG. 2 depicts dissolution data from the same experiments as depicted in FIG. 1, but with the time axis extended to show data for the 1:3 co-crystal up to about 13.5 hours. Dissolution of co-crystals of the present invention having ratios of human insulin to B29-Nε-octanoyl-human insulin of 3:1 (- - -), 1:1 (———), and 1:3 (■■■) are compared with the dissolution of co-crystals of a preparation of human insulin-protamine crystals (----).

DESCRIPTION OF THE INVENTION

Figure 1:
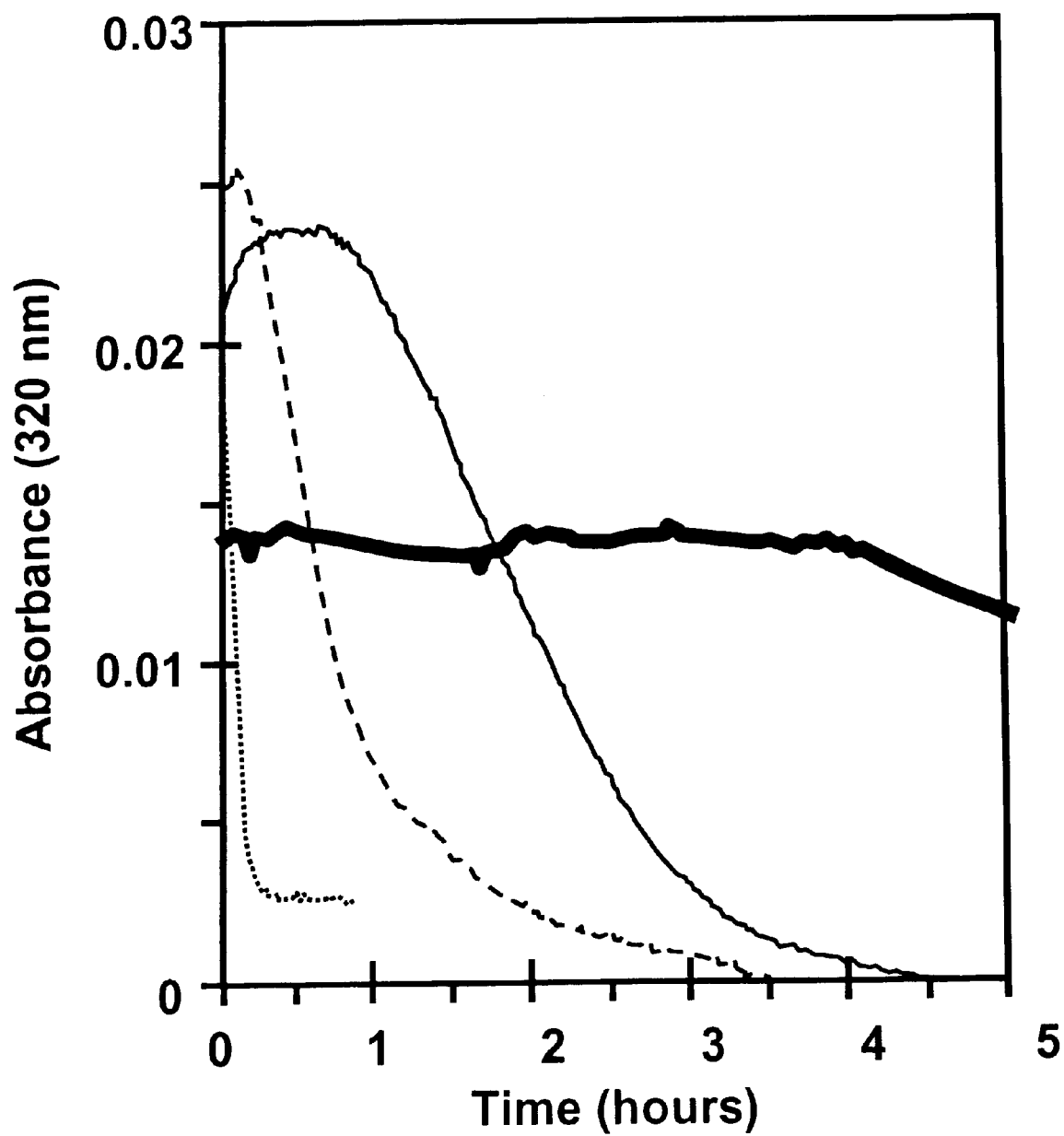
Figure 2:
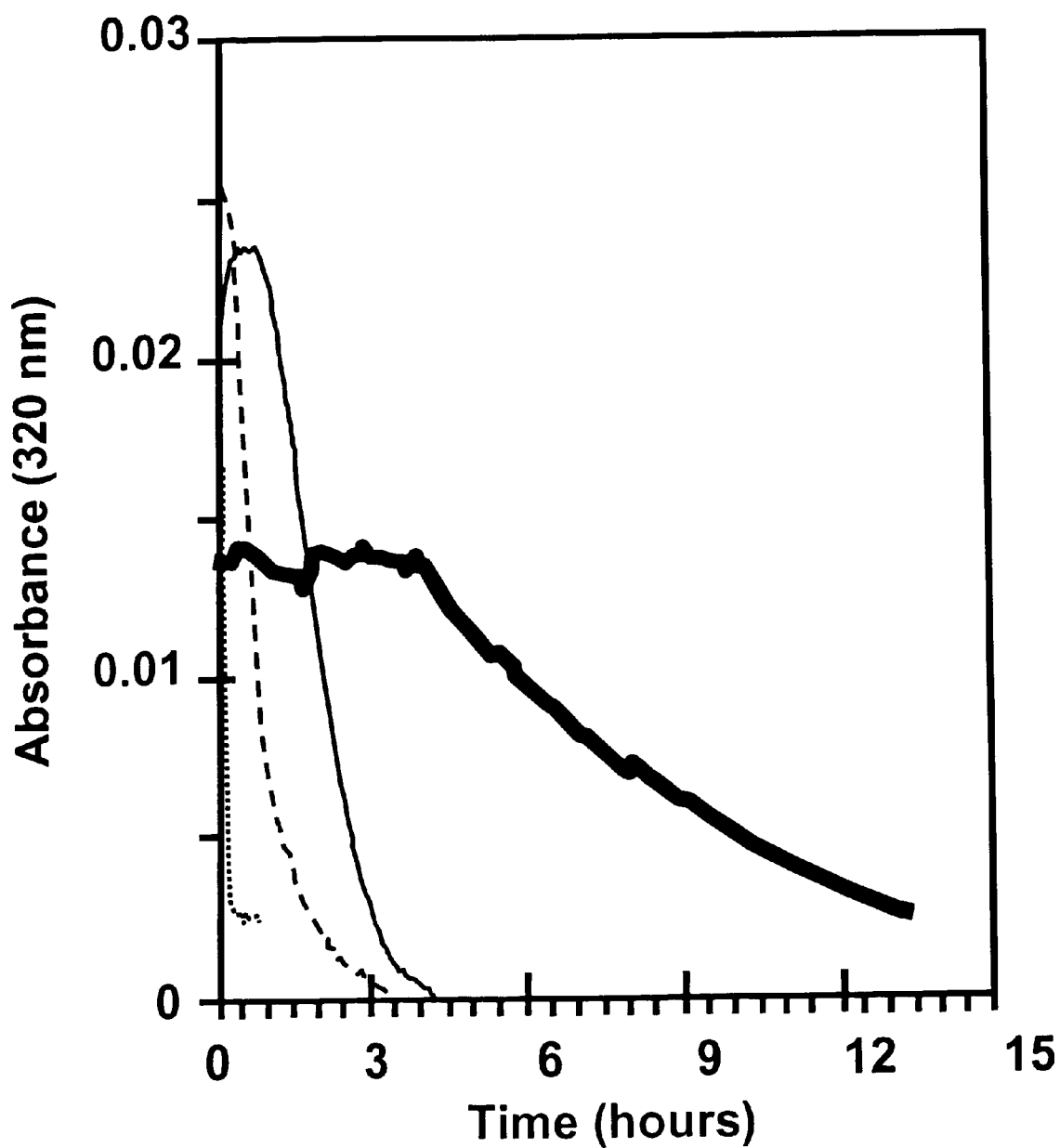

The term "mixed hexamers" refers to a mixture of protein hexamers and derivatized protein hexamers, wherein the protein hexamers are comprised of zinc and a protein selected from the group consisting of insulin, insulin analogs, and proinsulins, and wherein the derivatized protein hexamers are comprised of zinc and a derivatized protein selected from the group consisting of derivatized insulin, derivatized insulin analogs, and derivatized proinsulins. The level of zinc actually incorporated into a hexamer is between about 2 and about 4 atoms of zinc per hexamer.

The term "hybrid hexamer" refers to a hexamer comprised of six monomers and zinc, wherein at least one monomer is selected from the group consisting of insulin, insulin analogs, and proinsulins, and at least one monomer is selected from the group consisting of derivatized insulin, derivatized insulin analogs, and derivatized proinsulins. The level of zinc actually incorporated into a hexamer is commonly known to be between about 2 and about 4 atoms of zinc per hexamer.

As used herein, the term "co-crystal" means a microcrystal of the present invention.

The term "insoluble composition" refers to matter in either a microcrystalline state or in an amorphous precipitate state. The presence of microcrystals or amorphous precipitate can be ascertained by visual and microscopic examination. Solubility depends on solvent, and a particular composition may be insoluble in one solvent, but soluble in another.

The term, "microcrystal" means a solid that is comprised primarily of matter in a crystalline state, wherein the individual crystals are predominantly of a single crystallographic composition and are of a microscopic size, typically of longest dimension within the range 1 micron to 100 microns. The term "microcrystalline" refers to the state of being a microcrystal.

The term "rod-like" means the distinctive microcrystal morphology that is also described as pyramidal-tipped tetragonal rods. The morphology of microcrystals of the present invention are easily determined by microscopic examination.

The term "irregular morphology" is a characterization of microcrystals whose morphology, as determined by microscopic examination, is not readily classified into any of the well-known crystal types, is not a single type of crystal morphology, or is not readily determinable because the size of the crystals is too small for certain classification.

The term "amorphous precipitate" refers to insoluble material that is not crystalline in form. The person of ordinary skill can distinguish crystals from amorphous precipitate. The amorphous precipitates of the present invention have advantageous pharmacological properties in their own right, and also are intermediates in the formation of the microcrystals of the present invention.

The term "protein" may have its common meaning, that is, a polymer of amino acids. The term "protein," as used herein, also has a narrower meaning, that is, a protein selected from the group consisting of insulin, insulin analogs, and proinsulins. The term "un-derivatized proteins" also refers to a protein selected from the group consisting of insulin, insulin analogs, and proinsulins.

As used in the claims, and elsewhere as the context dictates, the term "total protein" refers to the combined amount of protein (insulin, an insulin analog, or a proinsulin) and derivatized protein (derivatized insulin, a derivatized insulin analog, or a derivatized proinsulin). Although protamine and other known complexing compounds are also proteins in the broadest sense of that term, the term "total protein" does not include them.

The term "derivatized proteins" refers to a protein selected from the group consisting of derivatized insulin, derivatized insulin analogs, and derivatized proinsulin that is derivatized by a functional group such that the derivatized protein is either less soluble in an aqueous solvent than is the un-derivatized protein, is more lipophilic than un-derivatized insulin, or produces a complex with zinc and protamine that are less soluble than the corresponding complex with the un-derivatized protein. The determination of either the solubility or lipophilicity of proteins and derivatized proteins is well-known to the skilled person. The solubility of derivatized proteins and protein in complexes with zinc and protamine can be readily determined by well-known procedures [Graham and Pomeroy, J. Pharm. Pharmacol. 36:427–430 (1983), as modified in DeFelippis, M. R. and Frank, B., EP 735,048], or the procedure used herein.

Many examples of such derivatized proteins are known in the art, including benzoyl, p-tolyl-sulfonamide carbonyl, and indolyl derivatives of insulin and insulin analogs [Havelund, S., et al., WO95/07931, published Mar. 23, 1995]; alkyloxycarbonyl derivatives of insulin [Geiger, R., et al., U.S. Pat. No. 3,684,791, issued Aug. 15, 1972; Brandenberg, D., et al., U.S. 3,907,763, issued Sep. 23, 1975]; aryloxycarbonyl derivatives of insulin [Brandenberg, D., et al., U.S. Pat. No. 3,907,763, issued Sep. 23, 1975]; alkylcarbamyl derivatives [Smyth, D. G., U.S. Pat. No. 3,864,325, issued Feb. 4, 1975; Lindsay, D. G., et al., U.S. Pat. No. 3,950,517, issued Apr. 13, 1976]; carbamyl, O-acetyl derivatives of insulin [Smyth, D. G., U.S. Pat. No. 3,864,325 issued Feb. 4, 1975]; cross-linked, alkyl dicarboxyl derivatives [Brandenberg, D., et al., U.S. Pat. No. 3,907,763, issued Sep. 23, 1975]; N-carbamyl, O-acetylated insulin derivatives [Smyth, D. G., U.S. Pat. No. 3,868,356, issued Feb. 25, 1975]; various O-alkyl esters [Markussen, J., U.S. Pat. No. 4,343,898, issued Aug. 10, 1982; Morihara, K., et al., U.S. Pat. No. 4,400,465, issued Aug. 23, 1983; Morihara, K., et al., U.S. Pat. No. 4,401,757, issued Aug. 30, 1983; Markussen, J., U.S. Pat. No. 4,489,159, issued Dec. 18, 1984; Obermeier, R., et al., U.S. Pat. No. 4,601,8,2, issued Jul. 22, 1986; and Andresen, F. H., et al., U.S. Pat. No. 4,601,979, issued Jul. 22, 1986]; alkylamide derivatives of insulin [Balschmidt, P., et al., U.S. Pat. No. 5,430,016, issued Jul. 4, 1995]; various other derivatives of insulin [Lindsay, D. G., U.S. Pat. No. 3,869,437, issued Mar. 4, 1975]; and the fatty acid-acylated proteins that are described herein.

The term "acylated protein" as used herein refers to a derivatized protein selected from the group consisting of insulin, insulin analogs, and proinsulin that is acylated with an organic acid moiety that is bonded to the protein through an amide bond formed between the acid group of an organic acid compound and an amino group of the protein. In general, the amino group may be the α-amino group of an N-terminal amino acid of the protein, or may be the ε-amino group of a Lys residue of the protein. An acylated protein may be acylated at one or more of the three amino groups that are present in insulin and in most insulin analogs. Mono-acylated proteins are acylated at a single amino group. Di-acylated proteins are acylated at two amino groups. Tri-acylated proteins are acylated at three amino groups. The organic acid compound may be, for example, a fatty acid, an aromatic acid, or any other organic compound having a carboxylic acid group that will form an amide bond-with an amino group of a protein, and that will lower the aqueous solubility, raise the lipophilicity, or decrease the solubility of zinc/protamine complexes of the derivatized protein compared with the underivatized protein.

The term "fatty acid-acylated proteins" refers to a an acylated protein selected from the group consisting of insulin, insulin analogs, and proinsulins that is acylated with a fatty acid that is bonded to the protein through an amide bond formed between the acid group of the fatty acid and an amino group of the protein. In general, the amino group may be the α-amino group of an N-terminal amino acid of the protein, or may be the ε-amino group of a Lys residue of the protein. A fatty acid-acylated protein may be acylated at one or more of the three amino groups that are present in insulin and in most insulin analogs. Mono-acylated proteins are acylated at a single amino group. Di-acylated proteins are acylated at two amino groups. Tri-acylated proteins are acylated at three amino groups. Fatty acid-acylated insulin is disclosed in a Japanese patent application 1-254,699. See also, Hashimoto, M., et al., *Pharmaceutical Research*, 6:171–176 (1989), and Lindsay, D. G., et al., *Biochemical J*. 121:737–745 (1971). Further disclosure of fatty acid-acylated insulins and fatty acylated insulin analogs, and of methods for their synthesis, is found in Baker, J. C., et al, U.S. Ser. 08/342,931, filed Nov. 17, 1994 and issued as U.S. Pat. No. 5,693,609, Dec. 2, 1997; Havelund, S., et al., WO95/07931, published Mar. 23, 1995, and a corresponding U.S. Pat. No. 5,750,497, May 12, 1998; and Jonassen, I., et al., WO96/29342, published Sep. 26, 1996. These disclosures are expressly incorporated herein by reference for describing fatty acid-acylated insulins and fatty acid-acylated insulin analogs and for enabling preparation of the same.

The term "fatty acid-acylated protein" includes pharmaceutically acceptable salts and complexes of fatty acid-acylated proteins. The term "fatty acid-acylated protein" also includes preparations of acylated proteins wherein the population of acylated protein molecules is homogeneous with respect to the site or sites of acylation. For example, Nε-mono-acylated protein, B1-Nα-mono-acylated protein, A1-Nα-mono-acylated protein, A1, B1-Nα-di-acylated protein, Nε, A1-Nα, di-acylated protein, Nε, B1-Nα, di-acylated protein, and Nε, A1, B1-Nα, tri-acylated protein are all encompassed within the term "fatty acid-acylated protein" for the purpose of the present invention. The term also refers to preparations wherein the population of acylated protein molecules has heterogeneous acylation. In the latter case, the term "fatty acid-acylated protein" includes mixtures of mono-acylated and di-acylated proteins, mixtures of mono-acylated and tri-acylated proteins, mixtures of di-acylated and tri-acylated proteins, and mixtures of mono-acylated, di-acylated, and tri-acylated proteins.

The term "insulin" as used herein, refers to human insulin, whose amino acid sequence and special structure are well-known. Human insulin is comprised of a twenty-one amino acid A-chain and a thirty-amino acid B-chain which are cross-linked by disulfide bonds. A properly cross-linked insulin contains three disulfide bridges: one between position 7 of the A-chain and position 7 of the B-chain, a second between position 20 of the A-chain and position 19 of the B-chain, and a third between positions 6 and 11 of the A-chain.

The term "insulin analog" means proteins that have an A-chain and a B-chain that have substantially the same amino acid sequences as the A-chain and B-chain of human insulin, respectively, but differ from the A-chain and B-chain of human insulin by having one or more amino acid deletions, one or more amino acid replacements, and/or one or more amino acid additions that do not destroy the insulin activity of the insulin analog.

"Animal insulins" are analogs of human insulin, and therefore, are insulin analogs as defined herein. Four such animal insulins are rabbit, pork, beef, and sheep insulin. The amino acid substitutions that distinguish these animal insulins from human insulin are presented below for the reader's convenience.

|  | Amino Acid Position | | | |
| --- | --- | --- | --- | --- |
|  | A8 | A9 | A10 | B30 |
| human insulin | Thr | Ser | Ile | Thr |
| rabbit insulin | Thr | Ser | Ile | Ser |
| pork insulin | Thr | Ser | Ile | Ala |
| beef insulin | Ala | Ser | Val | Ala |
| sheep insulin | Ala | Gly | Val | Ala |

Another type of insulin analog, "monomeric insulin analog" is well-known in the art. Monomeric insulin analogs are structurally very similar to human insulin, and have activity similar or equal to human insulin, but have one or more amino acid deletions, replacements or additions that tend to disrupt the contacts involved in dimerization and hexamerization which results in their having less tendency to associate to higher aggregation states. Monomeric insulin analogs are rapid-acting analogs of human insulin, and are disclosed, for example, in Chance, R. E., et al., U.S. Pat. No. 5,514,646, May 7, 1996; Brems, D. N., et al. *Protein Engineering*, 5:527–533 (1992); Brange, J. J. V., et al., EPO publication No. 214,826, published Mar. 18, 1987; Brange, J. J. V., et al., U.S. Pat. No. 5,618,913, Apr. 18, 1997; and Brange, J., et al., *Current Opinion in Structural Biology* 1:934–940 (1991). An example of monomeric insulin analogs is described as human insulin wherein Pro at position B28 is substituted with Asp, Lys, Leu, Val, or Ala, and wherein Lys at position B29 is Lys or is substituted with Pro, and also, AlaB26-human insulin, des(B28–B30)-human insulin, and des(B27)-human insulin. The monomeric insulin analogs employed as derivatives in the present crystals, or employed un-derivatized in the solution phase of suspension formulations, are properly cross-linked at the same positions as is human insulin.

Another group of insulin analogs for use in the present invention are those wherein the isoelectric point of the insulin analog is between about 7.0 and about 8.0. These analogs are referred to as "pI-shifted insulin analogs." Examples of such insulin analogs include ArgB31, ArgB32-human insulin, GlyA21, ArgB31, ArgB32-human insulin, ArgA0, ArgB31, ArgB32-human insulin, and ArgA0, GlyA21, ArgB31, ArgB32-human insulin.

Another group of insulin, analogs consists of insulin analogs that have one or more amino acid deletions that do not significantly disrupt the activity of the molecule. This group of insulin analogs is designated herein as "deletion analogs." For example, insulin analogs with deletion of one or more amino acids at positions B1–B3 are active. Likewise, insulin analogs with deletion of one or more amino acids.at positions B28–B30 are active. Examples of "deletion analogs" include des(B30)-human insulin, desPhe (B1)-human insulin, des(B27)-human insulin, des (B28–B30)-human insulin, and des(B1-B3)-human insulin. The deletion analogs employed as derivatives in the present crystals, or employed un-derivatized in the solution phase of suspension formulations, are properly cross-linked at the same positions as is human insulin.

Amidated amino acids, and particularly asparagine residues in insulin, are known to be chemically unstable [Jorgensen, K. H., et al. U.S. Pat. No. 5,008,241, issued Apr. 16, 1991; Dorschug, M., U.S. Pat. No. 5,656,722, issued Aug. 12, 1997]. Particularly, they are prone to deamidation and various rearrangement reactions under certain conditions that are well-known. Therefore, optionally, an insulin analog may be insulin or an insulin analog that has one or more of its amidated residues replaced with other amino acids for the sake of chemical stability. For example, Asn or Gln may be replaced with a non-amidated amino acid. Preferred amino acid replacements for Asn or Gln are Gly, Ser, Thr, Asp or Glu. It is preferred to replace one or.more Asn residues. In particular, AsnA18, AsnA21, or AsnB3, or any combination of those residues may be replaced by Gly, Asp, or Glu, for example. Also, GlnA15 or GlnB4, or both, may be replaced by either Asp or Glu. Preferred replacements are Asp at B21, and Asp at B3. Also preferred are replacements that do not change the charge on the:protein molecule, so that replacement of Asn or Gln with neutral amino acids is also preferred.

The term "proinsulin" means a single-chain peptide molecule that is a precursor of insulin. Proinsulin may be converted to insulin or to an insulin,analog by chemical or, preferably, enzyme-catalyzed reactions. In proinsulin, proper disulfide bonds are formed as described herein. Proinsulin comprises insulin or an insulin analog and a connecting bond or a connecting peptide. A connecting peptide has between 1 and about 35 amino acids. The connecting bond or connecting peptide connects to a terminal amino acid of the A-chain and to a terminal amino acid of the B-chain by an α-amide bond or by two α-amide bonds, respectively. Preferably, none of the amino acids in the connecting peptide is cysteine. Preferably, the C-terminal amino acid of the connecting peptide is Lys or Arg. Proinsulin may have the formula X-B-C-A-Y or may have the formula X-A-C-B-Y, wherein X is hydrogen or is a peptide of from 1 to about 100 amino acids that has either Lys or Arg at its C-terminal amino acid, Y is hydroxy, or is a peptide of from 1 to about 100 amino acids that has either Lys or Arg at its N-terminal amino acid, A is the A-chain of insulin or the A-chain of an insulin analog, C is a peptide of from 1 to about 35 amino acids, none of which is cysteine, wherein the C-terminal amino acid is Lys or Arg, and B is the B-chain of insulin or the B-chain of an insulin analog.

A "pharmaceutically acceptable salt" means a salt formed between any one or more of the charged groups in a protein and any one or more pharmaceutically acceptable, non-toxic cations or anions. Organic and inorganic salts include, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, carbonic, and the like, or for example, ammonium, sodium, potassium, calcium, or magnesium.

The verb "acylate" means to form the amide bond between a fatty acid and an amino group of a protein. A protein is "acylated" when one or more of its amino groups is combined in an amide bond with the acid group of a fatty acid.

The term "fatty acid" means a saturated or unsaturated, straight chain or branched chain fatty acid, having from one to eighteen carbon atoms.

The term "C1 to C18 fatty acid" refers to a saturated, straight chain or branched chain fatty acid having from one to eighteen carbon atoms.

The term "divalent metal cation" refers to the ion or ions that participate to form a complex with a multiplicity of protein molecules. The transition metals, the alkaline metals, and the alkaline earth metals are examples of metals that are known to form complexes with insulin. The transitional metals are preferred. Zinc is particularly preferred. Other transition metals that may be pharmaceutically acceptable for complexing with insulin proteins include copper, cobalt, and iron.

The term "complex" has two meanings in the present invention. In the first, the term refers to a complex formed between one or more atoms in the proteins that form the complex and one or more divalent metal cations. The atoms in the proteins serve as electron-donating ligands. The proteins typically form a hexamer complex with divalent transition metal cations. The second meaning of "complex" in the present invention is the association between the complexing compound and hexamers. The "complexing compound" is an organic molecule that typically has a multiplicity of positive charges that binds to, or complexes with hexamers in the insoluble composition, thereby stabilizing them against dissolution. Examples of complexing compounds suitable in the present invention include protamine, surfen, various globin proteins [Brange, J., Galenics of Insulin, Springer-Verlag, Berlin Heidelberg (1987)], and various polycationic polymer compounds known to complex with insulin.

The term, "protamine" refers to a mixture of strongly basic proteins obtained from fish sperm. The average molecular weight of the proteins in protamine is about 4,200 [Hoffmann, J. A., et al., Protein Expression and Purification, 1:127–133 (1990)]. "Protamine" can refer to a relatively salt-free preparation of the proteins, often called "protamine base." Protamine also refers to preparations comprised of salts of the proteins. Commercial preparations vary widely in their salt content.

Protamines are well-known to those skilled in the insulin art and are currently incorporated into NPH insulin products. A pure fraction of protamine is operable in the present invention, as well as mixtures of protamines. Commercial preparations of protamine, however, are typically not homogeneous with respect to the proteins present. These are nevertheless operative in the present invention. Protamine comprised of protamine base is operative in the present invention, as are protamine preparations comprised of salts of protamine, and those that are mixtures of protamine base and protamine salts. Protamine sulfate is a frequently used protamine salt. All mass ratios referring to protamine are given with respect to protamine free base. The person of ordinary skill can determine the amount of other protamine preparations that would meet a particular mass ratio referring to.protamine.

The term "suspension" refers to a mixture of a liquid phase and a solid phase that consists of insoluble or sparingly soluble particles that are larger than colloidal size. Mixtures of NPH microcrystals and an aqueous solvent form suspensions. Mixtures of amorphous precipitate and an aqueous solvent also forms a suspension. The term "suspension formulation" means a pharmaceutical composition wherein an active agent is present in a solid phase, for example, a microcrystalline solid, an amorphous precipitate, or both, which is finely dispersed in an aqueous solvent. The finely dispersed solid is such that it may be suspended in a fairly uniform manner throughout the aqueous solvent by the action of gently agitating the mixture, thus providing a reasonably uniform suspension from which a dosage volume may be extracted. Examples of commercially available insulin suspension formulations include, for example, NPH, PZI, and ultralente. A small proportion of the solid matter in a microcrystalline suspension formulation may be amorphous. Preferably, the proportion of amorphous material is less than 10%, and most preferably, less than 1% of the solid matter in a microcrystalline suspension. Likewise, a small proportion of the solid matter in an amorphous precipitate suspension may be microcrystalline.

"NPH insulin" refers to the "Neutral Protamine Hagedorn" preparation of insulin. Synonyms include human insulin NPH and insulin NPH, among many others. Humulin® N is a commercial preparation of NPH insulin. A related term is "NPL" which refers to an NPH-like preparation of LysB28, ProB29-human insulin analog. The meaning of these terms, and the methods for preparing them will be familiar to the person of ordinary skill in the insulin formulation art.

The term "aqueous solvent" refers to a liquid solvent that contains water. An aqueous solvent system may be comprised solely of water, may be comprised of water plus one or more miscible solvents, and may contain solutes. The more commonly-used miscible solvents are the short-chain organic alcohols, such as, methanol, ethanol, propanol, short-chain ketones, such as acetone, and polyalcohols, such as glycerol.

An "isotonicity agent" is a compound that is physiologically tolerated a imparts a suitable tonicity to a formulation to prevent the net flow of water across cell membranes that are in contact with an administered formulation. Glycerol, which is also known as glycerin, is commonly used as an isotonicity agent. Other isotonicity agents include salts, e.g., sodium chloride, and monosaccharides, e.g., dextrose and lactose.

The insoluble compositions of the present invention contain a hexamer-stabilizing compound. The term "hexamer-stabilizing compound" refers to a non-proteinaceous, small molecular weight compound that stabilizes the protein or derivatized protein in a hexameric aggregation state. Phenolic compounds, particularly phenolic preservatives, are the best known stabilizing compounds for insulin and insulin derivatives. Hexamer-stabilizing compounds stabilize the hexamer by binding to it through specific inter-molecular contacts. Examples of hexamer-stabilizing agents include: various phenolic compounds, phenolic preservatives, resorcinol, 4'-hydroxyacetanilide, 4-hydroxybenzamide, and 2,7-dihyroxynaphthalene. Multi-use formulations of the insoluble compositions of the present invention will contain a preservative, in addition to a hexamer-stabilizing compound. The preservative used in formulations of the present invention may be a phenolic preservative, and may be the same as, or different from the hexamer-stabilizing compound.

The term, "preservative" refers to a compound added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are benzalkonium chloride, benzethonium, chlorohexidine, phenol, m-cresol, benzyl alcohol, methylparaben, chlorobutanol, o-cresol, p-cresol, chlorocresol, phenylmercuric nitrate, thimerosal, benzoic acid, and various mixtures thereof. See, e.g., Wallhäusser, K.-H., *Develop. Biol. Standard*, 24:9–28, (1974) (S. Krager, Basel).

The term "phenolic preservative" includes the compounds phenol, m-cresol, o-cresol, p-cresol, chlorocresol, methylparaben, and mixtures thereof. Certain phenolic preservatives, such as phenol and m-cresol, are known to bind to insulin-like molecules and thereby to induce conformational changes that increase either physical or chemical stability, or both [Birnbaum, D. T., et al., *Pharmaceutical. Res.* 14:25–36 (1997); Rahuel-Clermont, S., et al., *Biochemistry* 36:5837–5845 (1997)].

The term "buffe" or "pharmaceutically acceptable buffer" refers to a compound that is known to be safe for use in insulin formulations and that has the effect of controlling the pH of the formulation at the pH desired for the formulation. The pH of the formulations of the present invention is from about 6.0 to about 8.0. Preferably the formulations of the present invention have a pH between about 6.8 and about 7.8. Pharmaceutically acceptable buffers for controlling pH at a moderately acidic pH to a moderately basic pH include such compounds as phosphate, acetate, citrate, arginine, TRIS, and histidine. "TRIS" refers to 2-amino-2-hydroxymethyl-1,3,-propanediol, and to any pharmacologically acceptable salt thereof. The free base and the hydrochloride form are two common forms of TRIS. TRIS is also known in the art as trimethylol aminomethane, tromethamine, and tris(hydroxymethyl)aminomethane. Other buffers that are pharmaceutically acceptable, and that are suitable for controlling pH at the desired level are known to the chemist of ordinary skill.

The term "administer" means to introduce a formulation of the present invention into the body of a patient in need thereof to treat a disease or condition.

The term "treating" refers to the management and care of a patient having diabetes or hyperglycemia, or other condition for which insulin administration is indicated for the purpose of combating or alleviating symptoms and complications of those conditions. Treating includes administering a formulation of present invention to prevent the onset of the symptoms or complications, alleviating the symptoms or complications, or eliminating the disease, condition, or disorder.

As mentioned above, the present invention provides insoluble compositions that have properties similar to NPH insulin in certain respects, and superior to NPH insulin in other respects. They are similar to NPH insulin in respect to their physical properties, as described hereafter. A light microscope equipped with an oil immersion objective and a crossed polarizer was utilized to examine microcrystals comprised of B29-Nε-octanoyl-human insulin, insulin, zinc, protamine, and phenol prepared according to the present invention. Examination at 1000x magnification showed that these microcrystals were single and rod-like, exhibiting a uniform crystal morphology. The sizes of these microcrystals fell generally within the range of approximately 2 microns long to 8 microns long. A direct comparison using this microscope showed that the morphology of these microcrystals appeared to be similar to that of commercially manufactured pork NPH microcrystals, which has elsewhere been described as rod-like. The size range of these microcrystals was also similar to that of commercially manufactured NPH microcrystals, which generally have an average length of about 5 microns. The commercial manufacturing specification for the mean length of NPH microcrystals is from 1 micron to 40 microns.

The microcrystals of the present invention are, however, unexpectedly and unpredictably different from NPH insulin crystals in their dissolution properties, and in their time action. In particular, the microcrystals of the present invention dissolve much more slowly under conditions that simulate physiologic conditions than do NPH insulin crystals, and provide a longer and flatter profile of blood glucose control than does NPH insulin. This was demostrated by the following experiments.

Certain derivatized proteins, in soluble form, were found to have time actions not significantly different from regular human insulin. Three groups of animals were used. Each animal in the first group received a dose (0.75 nmol/kg) of Humulin® R (soluble human insulin), each animal in the second group received a dose (0.75 nmol/kg) of soluble B29-Nε-octanoyl-human insulin ("C8-hI"), and each animal in the third group received a dose (0.75 nmol/kg) of soluble B29-Nε-decanoyl-human insulin ("C10-hI"). The experiments were carried out essentially as described in example 5, with five dogs per group. The proteins were administered subcutaneously. Blood glucose concentrations were determined, and are presented in the table below.

TABLE 1

Blood glucose concentrations before and after administration of Humulin ® R, soluble B29-Nε-octanoyl-human insulin ("C8-hI"), or soluble B29-Nε-decanoyl-human insulin ("C10-hI") in normal dogs simultaneously administered somatostatin to create a transient diabetic state. Values are mean ± standard error.

| Time (h) | Blood Glucose Concentration (mg/dL) | | |
|---|---|---|---|
| | Humulin ® R | Soluble C8-hI | Soluble C10-hI |
| −0.5 | 110 ± 2 | 115 ± 4 | 108 ± 2 |
| 0 | 101 ± 2 | 101 ± 7 | 96 ± 4 |
| 0.5 | 83 ± 5 | 80 ± 5 | 85 ± 6 |
| 1 | 54 ± 6 | 52 ± 4 | 70 ± 5 |
| 1.5 | 49 ± 4 | 51 ± 2 | 57 ± 4 |
| 2 | 48 ± 4 | 51 ± 2 | 52 ± 3 |
| 2.5 | 55 ± 4 | 60 ± 3 | 56 ± 4 |
| 3 | 59 ± 2 | 65 ± 4 | 58 ± 4 |
| 3.5 | 65 ± 2 | 73 ± 5 | 63 ± 4 |
| 4 | 71 ± 2 | 85 ± 6 | 68 ± 4 |
| 5 | 87 ± 2 | 110 ± 8 | 79 ± 3 |
| 6 | 104 ± 3 | 124 ± 4 | 91 ± 7 |
| 7 | 119 ± 8 | 145 ± 14 | 106 ± 8 |
| 8 | 144 ± 5 | 153 ± 16 | 119 ± 11 |

These data clearly show that soluble B29-Nε-octanoyl-human insulin and B29-Nε-decanoyl-human insulin, administered subcutaneously to normal dogs in a transient diabetic state, provide glucose lowering roughly comparable to that obtained with soluble human insulin. Most notably, soluble B29-Nε-octanoyl-human insulin shows a quicker onset, and shorter time action than does human insulin.

In a second experiment, the dissolution rate of co-crystals of insulin and B29-Nε-octanoyl-human insulin prepared in accordance with the present invention was found to be markedly longer than that of a commercially manufactured NPH-pork insulin. This was most unexpected in view of the data above. The rate of dissolution may be measured using well-known procedures [Graham and Pomeroy, *J. Pharm. Pharmacol.* 36:427–430 (1983), as modified in De Felippis, M. R. and Frank, B., EP 735,048], or the procedure used herein.

The dissolution rate of pork insulin NPH microcrystals was measured by placing 5 microliters of U100 pork insulin NPH into 3 mL of Dulbecco's phosphate buffered saline (without calcium or magnesium) in a 1 cm path length square quartz cuvette at a temperature of 22° C. This solution was stirred at a constant rate using a magnetic cuvette stirrer. Absorbance measurements at 320 nm were taken at 1 minute intervals. The absorbance at 320 nm corresponds to the light scattered by the insoluble particles present in the aqueous suspension. Consequently, as the microcrystals dissolve, the absorbance approaches zero. Pork insulin NPH microcrystals were completely dissolved after about 20 minutes.

The dissolution rate of protamine-zinc crystals of human insulin containing no co-crystallized acylated human insulin was also found to be about 20 minutes by the procedure used above. These crystals of NPH-human insulin were prepared essentially by the procedure of Preparation #1, below, except that no acylated protein was used, and 7 parts of human insulin were used. The data generated from this experiment are presented in FIG. 1 as the dashed line.

Co-crystals of the present invention comprised of human insulin and B29-Nε-octanoyl-LysB29 human insulin were prepared as described in Preparations #2, 4, and 5, below. In these preparations, human insulin and the acylated insulin were used in pre-crystallization mass ratios of 3:1, 1:1, and 1:3, respectively.

A procedure as described above was followed to measure the dissolution rate of these co-crystals. In summary, a volume of 12 microliters of each protamine-zinc-B29-Nε-octanoyl-LysB29 human insulin-human insulin co-crystalline suspension (containing no more than 50 U/mL) was placed into 3 mL of Dulbecco's phosphate buffered saline (without calcium or magnesium) in a 1 cm path length square quartz cuvette. This solution was stirred at the same constant rate and at the same temperature of 22° C. The data generated from this experiment are presented in FIG. 1, and show that the 3:1 co-crystals required more than 100 minutes to dissolve, that the 1:1 co-crystals required more than 150 minutes to dissolve, and that the 1:3 co-crystals required did not completely dissolve even after 400 minutes.

The time required for the absorbance during dissolution to reach half way from the starting absorbance value to the final absorbance value is defined as the $t_{1/2}$ value. The $t_{1/2}$ values for these preparations are presented below in Table 2.

TABLE 2

Dissolution $t_{1/2}$ values for Iletin NPH, Human Insulin NPH, and co-crystals of B29-octanoyl-human insulin and human insulin

| Identity | % B29-octanoyl-human insulin | % human insulin | % porcine insulin | $t_{1/2}$ value (minutes) |
|---|---|---|---|---|
| Iletin NPH | 0 | 0 | 100 | 6 |
| Human NPH | 0 | 100 | 0 | 7 |
| 3:1 co-crystal | 25 | 75 | 0 | 38 |
| 1:1 co-crystal | 50 | 50 | 0 | 117 |
| 1:3 co-crystal | 75 | 25 | 0 | >400 |

These experiments establish that, in Dulbecco's phosphate buffered saline (without calcium and magnesium), a solution that mimics the interstitial fluid in certain aspects, the rate of dissolution of the 3:1, 1:1, and 1:3 co-crystals is significantly slower than that of pork NPH microcrystals. These experiments also establish that the rate of dissolution of protamine-zinc-human insulin microcrystals is very similar to that of pork NPH insulin (Iletin NPH). These results further establish that the rate of dissolution of protamine-zinc-B29-Nε-octanoyl-LysB29 human insulin-human insulin co-crystals depends on the ratio of human insulin to B29-Nε-octanoyl-LysB29 human insulin present in the co-crystals, and, in particular, the rate of dissolution of protamine-zinc-B29-Nε-octanoyl-LysB29 human insulin-human insulin co-crystals decreases as the proportion of human insulin decreases.

Another dissolution method, based on HPLC determination of dissolved protein and derivatized protein, was used to compare the dissolution rate of the 1:3 microcrystals described above with commercial preparations of human insulin NPH, human insulin ultralente, and beef ultralente, and also to study the effects on dissolution rate of varying the ratio of protein to derivatized protein.

A volume (0.5 mL) of a U100 formulation was suspended in 200 mL of Dulbecco's phosphate buffered saline adjusted to pH 7.4 in a water-jacketed dissolution apparatus maintained at 25° C. The dissolution buffer also contained 1 mg/mL human serum albumin to prevent adsorption losses of dissolved insulins. The dissolution medium was stirred at a constant rate of 180 rpm. At regular intervals, 3.5 mL of this solution was taken out and filtered through a 0.22 µm, low protein-binding filter. The first 0.5 mL of the filtrate was discarded and the next 1.5 mL of the filtrate was acidified with 4 mL of 5 N HCl and subjected to HPLC analysis. The concentrations of the dissolved insulins were determined based on HPLC peak areas and the results were expressed as the percent dissolved as a function of time, with 100% being the total area of insulins in unfiltered samples. If the total area in unfiltered samples decreased slightly as a function of time, a linearly corrected value was used as 100%, for computation of percent dissolved at each time point. The results of these studies are presented in FIGS. 3 and 4.

Figure 3:
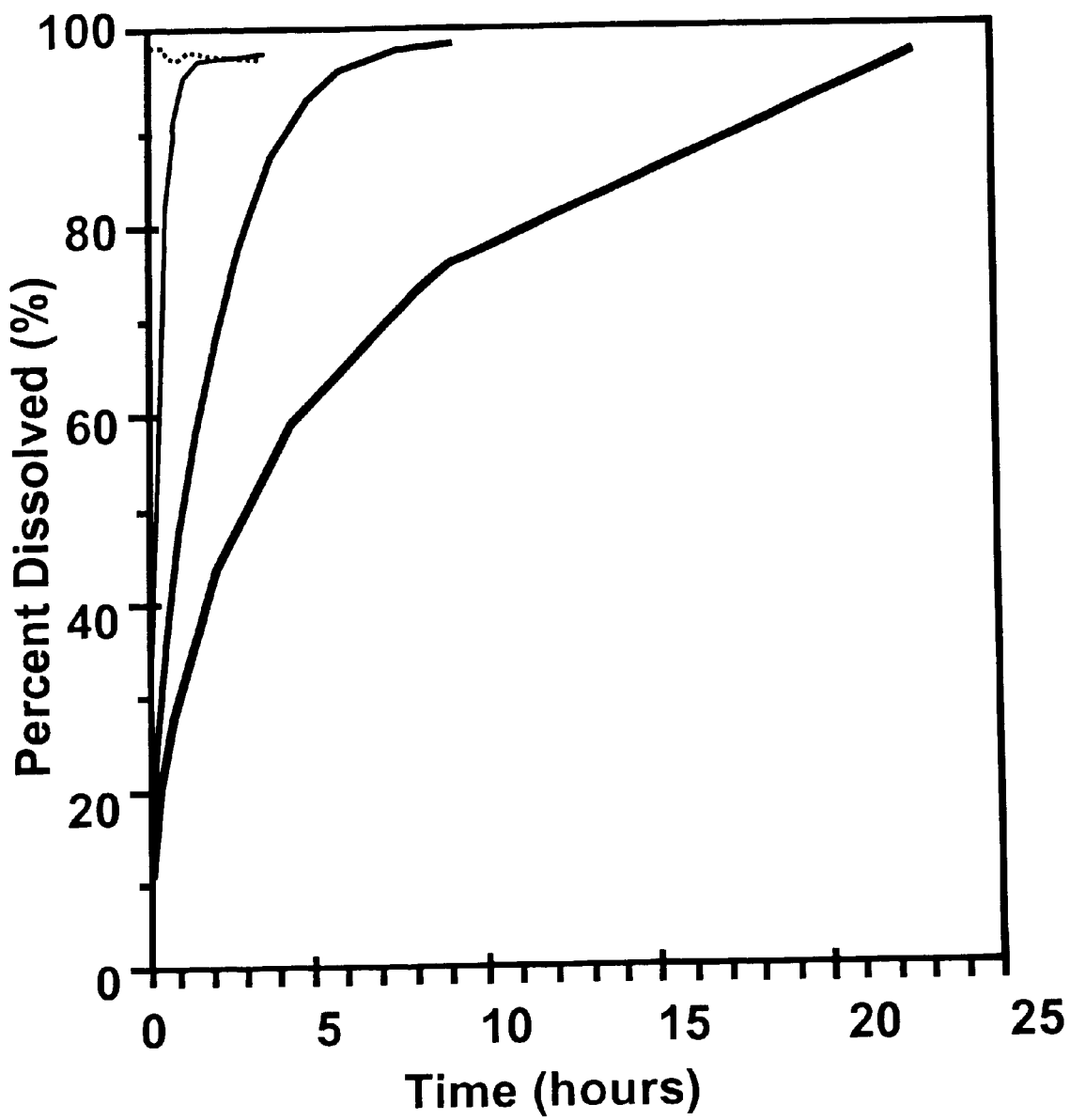
FIG. 3 depicts the dissolution co-crystals of the present invention having ratios of human insulin to B29-Nε-octanoyl-human insulin of 1:1 (———) and 1:3 (———), compared with the dissolution of with microcrystals comprised only of B29-Nε-octanoyl-human insulin (■■■), or a preparation of human insulin-protamine crystals (----).
Figure 4:
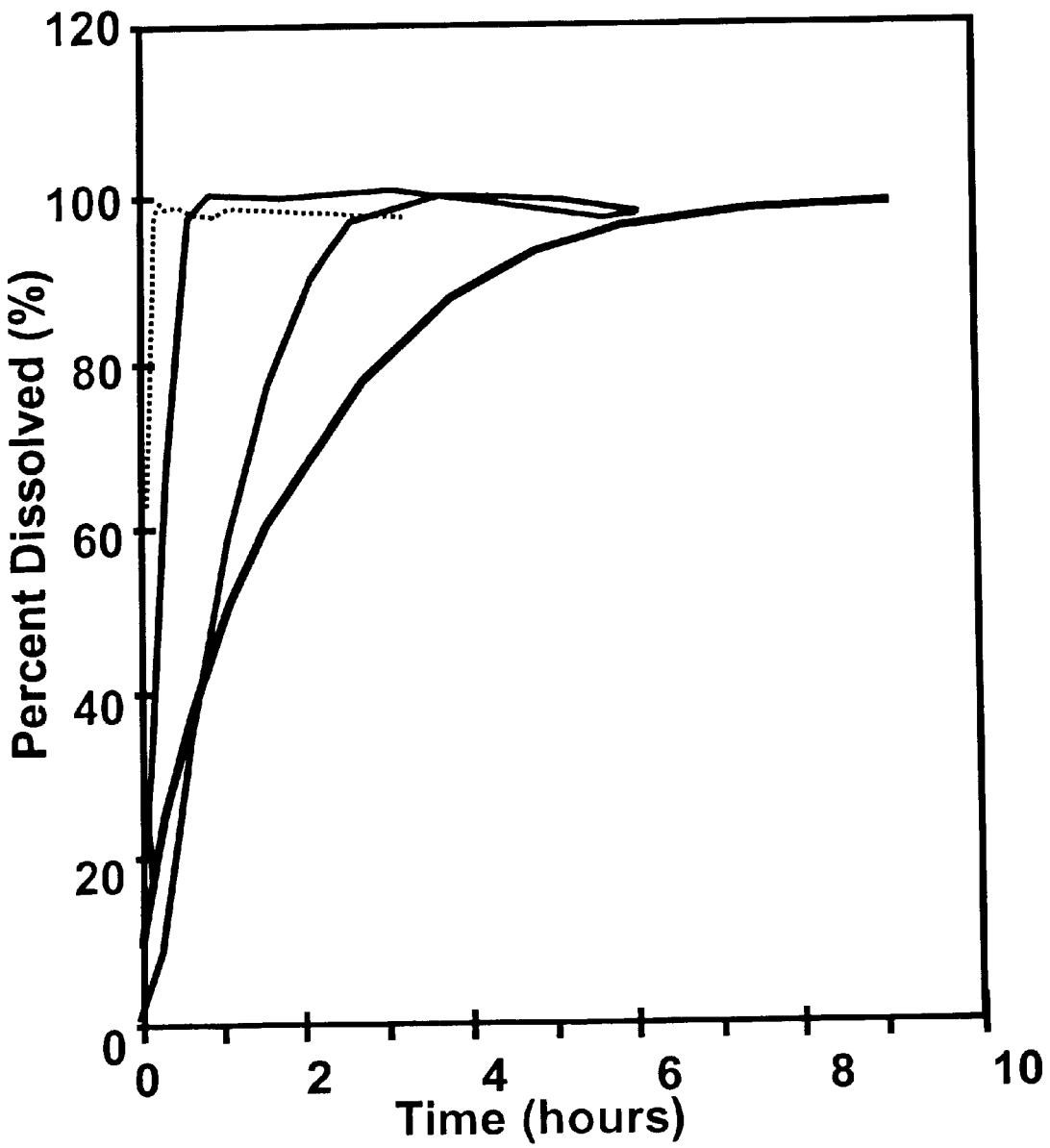
FIG. 4 depicts the dissolution of co-crystals of the present invention having a 1:3 ratio of human insulin to B29-Nε-octanoyl-human insulin (■■■), compared with preparations of human insulin-protamine crystals (----), human insulin ultralente (——) and beef ultralente (———).

The data of FIG. 3 show that the greater the fraction of derivatized protein incorporated into the microcrystal, the slower the dissolution rate. The data of FIG. 4 show that the 1:3 microcrystal of human insulin and B29-octanoyl human insulin dissolves significantly more slowly than both human insulin NPH and human insulin ultralente. Most significantly, the 1:3 microcrystal has a dissolution rate very similar to that of beef ultralente. Beef ultralente has long been considered a nearly ideal long-acting insulin preparations, both because of its very long protraction of biological activity, and because of the flatness of the pharmacodynamic response after its administration. It is thus predicted that these microcrystals may approach or exceed beef ultralente in their ability to provide control of basal glucose output for very long time periods.

Because the time action profile of NPH preparations is related strongly to the rate of dissolution of the microcrystals in the subcutaneous interstitial fluid, it is concluded from these experiments that the microcrystalline compositions of the present invention possess a more protracted duration of action when administered subcutaneously to diabetic patients than existing commercial NHP insulin preparations. Importantly, these results also establish that the present invention makes it possible to control, and even to optimize, the duration of action in patients by manipulating the ratio of protein to derivatized protein.

This ability to manipulate the duration of action by simply varying the ratios of protein and derivatized protein is most significant when viewed against the historical backdrop. Historically, a major obstacle to the development of insulin formulations for controlling basal glucose output has been that their time-action has been inflexibly linked to the inherent molecular properties of the protein, for example, albumin-binding affinity, isoelectric point, or solubility. The consequence was that only a single time-action was possible for each molecule or formulation, and the only recourse for improving the pharmacokinetics was a further modification of the molecule.

A long sought goal has been to develop controlled-release delivery systems where the pharmacokinetics can be precisely and conveniently adjusted by manipulating the formulation matrix. Much academic and industrial research in this area has been directed towards insulin over the past years, however, the goal of controlled release has proven particularly elusive because of the extremely narrow therapeutic index of insulin, its chronic-use requirement, as well as economic considerations which bias against sophisticated and expensive processes and formulations.

A major advantage of the present invention is that it is a controlled release system where the pharmacokinetics of insulin release can be more conveniently controlled than other proposed controlled release technologies. That is, an insoluble composition comprised of a protein insulin with a derivatized protein provides a convenient means to adjust the dissolution rate and hence make controlled-release possible. While not intended to be limiting, it is believed that the pharmacological efficacy of the insoluble compositions of the present invention is based on the slow release of a consistent proportion of protein and derivatized protein from the composition. It is further believed, without limiting the invention, that a significant underlying feature of this invention is the complete or early complete homogeneity of the insoluble composition. For microcrystals, it is believed that every individual microcrystal in the suspension is comprised of very nearly the same ratio of protein and derivatized protein. This ratio closely reflects the ratio of protein to derivatized protein combined in solution prior to crystallization. It is also believed that, as the microcrystals dissolve, a consistent and predetermined proportion of protein and derivatized protein is released throughout the entire duration of dissolution. The significance of this behavior is considerable because it results in a constant, but reduced rate of release of the two active molecules from the site of injection to the bloodstream. In order to achieve this object, particular attention must be given to the process for preparing the compositions.

The present discovery that it is possible to crystallize protein with derivatized protein, and thereby obtain a homogeneous co-crystal, was a surprising finding in view of the complexity of the parameters affecting protein crystallization: specific and non-specific inter-molecular interactions, such as, hydrogen-bonding, electrostatic interactions, hydrophobic interactions, van der Waals forces, excluded-volume effects, solubility, and steric bulk. Although the fundamental understanding of small molecule crystallization is relatively advanced, for complex macromolecules it is still largely a qualitative science and current practice consists of empirically applying large arrays of crystallization recipes.

The hydrophobic effect has been proposed as a major driving force for protein association [Chothia, C. et al., *Nature* 256:705–708 (1975)]. Furthermore, strong correlation between surface hydrophobicity and protein-protein contacts have been noted [Young, L., et al., *Protein Science* 3:717–729 (1994)]. Yet, in view of the complexity of protein crystallization, the finding that derivatized insulins can co-crystallize with un-derivatized protein in a manner that is isomorphous, or nearly isomorphous to normal insulin, is surprising.

The co-crystallization of two related therapeutic proteins for the purpose of modifying therapeutic behavior is a new concept. To a large extent this is because the vast majority of protein crystallization work is motivated by the goal of obtaining single, large, homogeneous crystals suitable for x-ray diffraction structural analysis. Although protein co-crystals are known, such co-crystal systems are characterized as host-substrate complexes e.g. a protein and its receptor, protein-DNA complexes, and protein receptor-drug complexes. These host-substrate complex co-crystals are fundamentally different than the co-crystals of the present invention because there is no complex formed between the protein and derivatized protein.

The predictability of the proportions of protein and derivatized protein and the homogeneity of the insoluble compositions of the present invention were demonstrated by measuring (by HPLC) the concentrations of protein and derivatized protein during dissolution studies using two preparations of microcrystals that were prepared with known quantities of human insulin (protein) and B29-octanoyl-human insulin (derivatized protein). In the first preparation, the mass proportion of protein added to derivatized protein added was 1:3. In the second preparation, the proportion was 55:45. For the 1:3 microcrystals, B29-octanoyl-human insulin constituted between about 73% and 76% of the total protein for 14 measurements over 10 hours during dissolution under conditions as described for the dissolution test above. No trend in the data was observed. For the 55:45 microcrystals, B29-octanoyl-human insulin constituted between about 43% and 47% of the total protein for 9 measurements taken over a period of about 3.75 hours during dissolution under conditions as described for the dissolution test above. Again, no trend in the data was observed.

The insoluble compositions of the present invention may be crystals with rod-like morphology or with an irregular morphology, or they may be amorphous precipitates. Preferred insoluble compositions are comprised of acylated insulin or acylated insulin analog, zinc ions, which are present at about 0.3 to about 0.7 mole per mole of total protein, a phenolic preservative selected from the group consisting of phenol, m-cresol, o-cresol, p-cresol, chlorocresol, methylparaben, and mixtures thereof and is present in sufficient proportions with respect to total protein to stabilize the T3R3 or R6 hexamer conformation, and protamine, which is present at about 0.15 to about 0.7 mole per mole of total protein.

A preferred group of insulin analogs for preparing derivatized insulin analogs used to form the present insoluble compositions consists of animal insulins, deletion analogs, and pI-shifted analogs. A more preferred group consists of animal insulins and deletion analogs. Deletion analogs are yet more preferred.

Another preferred group of insulin analogs for use in the microcrystals of the present invention consists of the monomeric insulin analogs. Particularly preferred are those monomeric insulin analogs wherein the amino acid residue at position B28 is Asp, Lys, Leu, Val, or Ala, the amino acid residue at position B29 is Lys or Pro, the amino acid residue at position B10 is His or Asp, the amino acid residue at position B1 is Phe, Asp or deleted alone or in combination with a deletion of the residue at position B2, the amino acid residue at position B30 is Thr, Ala, Ser, or deleted, and the amino acid residue at position B9 is Ser or Asp; provided that either position B28 or B29 is Lys.

Another preferred group of insulin analogs for use in the present invention consists of those wherein the isoelectric point of the insulin analog is between about 7.0 and about 8.0. These analogs are referred to as "pI-shifted insulin analogs." Examples of pI-shifted insulin analogs include, for example, ArgB31, ArgB32-human insulin, GlyA21, ArgB31, ArgB32-human insulin, ArgA0, ArgB31, ArgB32-human insulin, and ArgA0,GlyA21, ArgB31, ArgB32-human insulin.

Another preferred group of insulin analogs consists of LysB28, ProB29-human insulin (B28 is Lys; B29 is Pro); AspB28-human insulin (B28 is Asp), AspB1-human insulin, ArgB31, ArgB32-human insulin, ArgA0-human insulin, AspB1,GluB13-human insulin, AlaB26-human insulin, GlyA21-human insulin, des(ThrB30)-human insulin, and GlyA21, ArgB31, ArgB32-human insulin.

Especially preferred insulin analogs include LysB28, ProB29-human insulin, des(ThrB30)-human insulin, AspB28-human insulin, and AlaB26-human insulin. Another especially preferred insulin analog is GlyA21, ArgB31, ArgB32-human insulin [Dörschug, M., U. S. Pat. No. 5,656,722, Aug. 12, 1997]. The most preferred insulin analog is LysB28, ProB29-human insulin.

The preferred derivatized proteins are acylated proteins, and the preferred acylated proteins for the microcrystals and formulations of the present invention are fatty acid-acylated insulin, and fatty acid-acylated insulin analogs. Fatty acid-acylated human insulin is highly preferred. Fatty acid-acylated insulin analogs are equally highly preferred.

The particular group used to derivatize insulin, an insulin analog, or a proinsulin (collectively, protein) may be any chemical moiety that does not significantly reduce the biological activity of the protein, is not toxic when bonded to the protein, and most importantly, reduces the aqueous solubility, raises the lipophilicity, or decreases the solubility of zinc/protamine complexes of the derivatized protein.

One preferred group of acylating moieties consists of fatty acids that are straight chain and saturated. This group consists of methanoic acid (C1), ethanoic acid (C2), propanoic acid (C3), n-butanoic acid (C4), n-pentanoic acid (C5), n-hexanoic acid (C6), n-heptanoic acid (C7), n-octanoic acid (C8), n-nonanoic acid (C9), n-decanoic acid (C10), n-undecanoic acid (C11), n-dodecanoic acid (C12), n-tridecanoic acid (C13), n-tetradecanoic acid (C14), n-pentadecanoic acid (C15), n-hexadecanoic acid (C16), n-heptadecanoic acid (C17), and n-octadecanoic acid (C18). Adjectival forms are formyl (C1), acetyl (C2), propionyl (C3), butyryl (C4), pentanoyl (C5), hexanoyl (C6), heptanoyl (C7), octanoyl (C8), nonanoyl (C9), decanoyl (C10), undecanoyl (C11), dodecanoyl (C12), tridecanoyl (C13), tetradecanoyl (C14) or myristoyl, pentadecanoyl (C15), hexadecanoyl (C16) or palmitic, heptadecanoyl (C17), and octadecanoyl (C18) or stearic.

A preferred group of fatty acids for forming the fatty acid-acylated proteins used in the microcrystals of the present invention consists of fatty acids having an even number of carbon atoms—that is, C2, C4, C6, C8, CIO, C12, C14, C16, and C18 saturated fatty acids.

Another preferred group of fatty acids for forming the fatty acid-acylated proteins used in the microcrystals of the present invention consists of fatty acids having an odd number of carbon atoms—that is, C1, C3, C5, C7, C9, C11, C13, C15, and C17 saturated fatty acids.

Another preferred group of fatty acids for forming the fatty acid-acylated proteins used in the microcrystals of the present invention consists of fatty acids having more than 5 carbon atoms—that is, C6, C7, C8, C9, C10, C11, C12, C13, C14, C15, C16, C17, and C18 saturated fatty acids.

Another preferred group of fatty acids for forming the fatty acid-acylated proteins used in the microcrystals of the present invention consists of fatty acids having less than 9 carbon atoms—that is, C1, C2, C3, C4, C5, C6, C7, and C8 saturated fatty acids.

Another preferred group of fatty acids for forming the fatty acid-acylated proteins used in the microcrystals of the present invention consists of fatty acids having between 6 and 8 carbon atoms—that is, C6, C7, and C8, saturated fatty acids.

Another preferred group of fatty acids for forming the fatty acid-acylated proteins used in the microcrystals of the present invention consists of fatty acids having more than between 4 and 6 carbon atoms—that is, C4, C5, and C6, saturated fatty acids.

Another preferred group of fatty acids for forming the fatty acid-acylated proteins used in the microcrystals of the present invention consists of fatty acids having more than between 2 and 4 carbon atoms—that is, C2, C3, and C4, saturated fatty acids.

Another preferred group of fatty acids for forming the fatty acid-acylated proteins used in the microcrystals of the present invention consists of fatty acids having less than 6 carbon atoms—that is, C1, C2, C3, C4, and C5 saturated fatty acids.

Another preferred group of fatty acids for forming the fatty acid-acylated proteins used in the microcrystals of the present invention consists of fatty acids having less than 4 carbon atoms—that is, C1, C2, and C3 saturated fatty acids.

Another preferred group of fatty acids for forming the fatty acid-acylated proteins used in the microcrystals of the present invention consists of fatty acids having more than 9 carbon atoms—that is, C10, C11, C12, C13, C14, C15, C16, C17, and C18 saturated fatty acids.

Another preferred group of fatty acids for forming the fatty acid-acylated proteins used in the microcrystals of the present invention consists of fatty acids having an even number of carbon atoms and more than 9 carbon atoms—that is, C10, C12, C14, C16, and C18 saturated fatty acids.

Another preferred group of fatty acids for forming the fatty acid-acylated proteins used in the microcrystals of the present invention consists of fatty acids having 12, 14, or 16 carbon atoms, that is, C12, C14, and C16 saturated fatty acids.

Another preferred group of fatty acids for forming the fatty acid-acylated proteins used in the microcrystals of the present invention consists of fatty acids having 14 or 16 carbon atoms, that is, C14 and C16 saturated fatty acids. Fatty acids with 14 carbons are particularly preferred. Fatty acids with 16 carbons are also particularly preferred.

Another preferred group of fatty acids for forming the fatty acid-acylated proteins used in the microcrystals of the present invention consists of saturated fatty acids having between 4 and 10 carbon atoms, that is C4, C5, C6, C7, C8, C9, and C10 saturated fatty acids.

Another preferred group of fatty acids for forming the fatty acid-acylated proteins used in the microcrystals of the present invention consists of saturated fatty acids having an even number of carbon atoms between 4 and 10 carbon atoms, that is C4, C6, C8, and C10 saturated fatty acids.

Another preferred group of fatty acids for forming the fatty acid-acylated proteins used in the microcrystals of the present invention consists of fatty acids having between 6, 8, or 10 carbon atoms. Fatty acids with 6 carbons are particularly preferred. Fatty acids with 8 carbons are also particularly preferred. Fatty acids with 10 carbons are particularly preferred.

The skilled person will appreciate that narrower preferred groups are made by combining the preferred groups of fatty acids described above.

Another preferred group of acylating moieties consists of saturated fatty acids that are branched. A branched fatty acid has at least two branches. The length of a "branch" of a branched fatty acid may be described by the number of carbon atoms in the branch, beginning with the acid carbon. For example, the branched fatty acid 3-ethyl-5-methylhexanoic acid has three branches that are five, six, and six carbons in length. In this case, the "longest" branch is six carbons. As another example, 2,3,4,5-tetraethyloctanoic acid has five branches that are 4, 5, 6, 7, and 8 carbons long. The "longest" branch is eight carbons. A preferred group of branched fatty acids are those having from three to ten carbon atoms in the longest branch.

A representative number of such branched, saturated fatty acids will be mentioned to assure the reader's comprehension of the range of such fatty acids that may be used as acylating moieties of the proteins in the present invention: 2-methyl-propioinic acid, 2-methyl-butyric acid, 3-methyl-butyric acid, 2,2-dimethyl-propionic acid, 2-methyl-pentanoic acid, 3-methyl-pentanoic acid, 4-methyl-pentanoic acid, 2,2-dimethyl-butyric acid, 2,3-dimethyl-butyric acid, 3,3-dimethyl-butyric acid, 2-ethyl-butyric acid, 2-methyl-hexanoic acid, 5-methyl-hexanoic acid, 2,2-dimethyl-pentanoic acid, 2,4-dimethyl-pentanoic acid, 2-ethyl-3-methyl-butyric acid, 2-ethyl-pentanoic acid, 3-ethyl-pentanoic acid, 2,2-dimethyl-3-methyl-butyric acid, 2-methyl-heptanoic acid, 3-methyl-heptanoic acid, 4-methyl-heptanoic acid, 5-methyl-heptanoic acid, 6-methyl-heptanoic acid, 2,2-dimethyl-hexanoic acid, 2,3-dimethyl-hexanoic acid, 2,4-dimethyl-hexanoic acid, 2,5-dimethyl-hexanoic acid, 3,3,-dimethyl-hexanoic acid, 3,4-dimethyl-hexanoic acid, 3,5-dimethyl-hexanoic acid, 4,4-dimethyl-hexanoic acid, 2-ethyl-hexanoic acid, 3-ethyl-hexanoic acid, 4-ethyl-hexanoic acid, 2-propyl-pentanoic acid, 2-ethyl-hexanoic acid, 3-ethyl-hexanoic acid, 4-ethyl-hexanoic acid, 2-(1-propyl)pentanoic acid, 2-(2-propyl) pentanoic acid, 2,2-diethyl-butyric acid, 2,3,4-trimethyl-pentanoic acid, 2-methyl-octanoic acid, 4-methyl-octanoic acid, 7-methyl-octanoic acid, 2,2-dimethyl-heptanoic acid, 2,6-dimethyl-heptanoic acid, 2-ethyl-2-methyl-hexanoic acid, 3-ethyl-5-methyl-hexanoic acid, 3-(1-propyl)-hexanoic acid, 2-(2-butyl)-pentanoic acid, 2-(2-(2-methylpropyl))pentanoic acid, 2-methyl-nonanoic acid, 8-methyl-nonanoic acid, 6-ethyl-octanoic acid, 4-(1-propyl)-heptanoic acid, 5-(2-propyl)-heptanoic acid, 3-methyl-undecanoic acid, 2-pentyl-heptanoic acid, 2,3,4,5,6-pentamethyl-heptanoic acid, 2,6-diethyl-octanoic acid, 2-hexyl-octanoic acid, 2,3,4,5,6,7-hexamethyl-octanoic acid, 3,3-diethyl-4,4-diethyl-hexanoic acid, 2-heptyl-nonanoic acid, 2,3,4,5-tetraethyl-octanoic acid, 2-octyl-decanoic acid, and 2-(1-propyl)-3-(1-propyl)-4,5-diethyl-6-methyl-heptanoic acid.

Yet another preferred group of acylating moieties consists of cyclic alkyl acids having from 5 to 24 carbon atoms, wherein the cyclic alkyl moiety, or moieties, have 5 to 7 carbon atoms. A representative number of such cyclic alkyl acids will be mentioned to assure the reader's comprehension of the range of such acids that may be used as acylating moieties of the proteins in the present invention: cyclopentyl-formic acid, cyclohexyl-formic acid, 1-cyclopentyl-acetic acid, 2-cyclohexyl-acetic acid, 1,2-dicyclopentyl-acetic acid, and the like.

A preferred group of derivatized proteins for use in the insoluble compositions of the present invention consists of mono-acylated proteins. Mono-acylation at the &-amino group is most preferred. For insulin, mono-acylation at LysB29 is preferred. Similarly, for certain insulin analogs, such as, LysB28, ProB29-human insulin analog, mono-acylation at the ε-amino group of LysB28 is most preferred. Mono-acylation at the α-amino group of the B-chain (B1) is also preferred. Mono-acylation at the α-amino group of the A-chain (A1) is also preferred.

Another preferred group of acylated proteins for use in the insoluble compositions of the present invention consists of di-acylated proteins. The di-acylation may be, for example, at the ε-amino group of Lys and at the α-amino group of the B-chain, or may be at the ε-amino group of Lys and at the α-amino group of the A-chain, or may be at the α-amino group the A-chain and at the α-amino group of the B-chain.

Another preferred group of acylated proteins for use in the insoluble compositions of the present invention consists of tri-acylated proteins. Tri-acylated proteins are those that are acylated at the ε-amino group of Lys, at the α-amino group of the B-chain, and at the α-amino group of the A-chain.

It is also preferred to use acylated proteins that are a mixture of mono-acylated and di-acylated proteins.

It is likewise preferred to use acylated proteins that are a mixture of mono-acylated and tri-acylated proteins.

Another preferred group of acylated proteins consists of a mixture of di-acylated and tri-acylated proteins.

Also preferred is to use acylated proteins that are a mixture of mono-acylated, di-acylated, and tri-acylated proteins.

Certain fatty acid-acylated proteins used in the present microcrystals will be mentioned to assure the reader's comprehension of the scope of the present invention. The list is illustrative, and the fact that a particular fatty acid-acylated protein is not mentioned does not mean that a microcrystal containing it is not within the scope of the present invention.

B29-Nε-Formyl-human insulin.
B1-Nα-Formyl-human insulin.
A1-Nα-Formyl-human insulin.
B29-Nε-Formyl-, B1-Nα-formyl-human insulin.
B29-Nε-Formyl-, A1-Nα-formyl-human insulin.
A1-Nα-Formyl-, B1-Nα-formyl-human insulin.
B29-Nε-Formyl-, A1-Nα-formyl-, B1-Nα-formyl-human insulin.
B29-Nε-Acetyl-human insulin.
B1-Nα-Acetyl-human insulin.
A1-Nα-Acetyl-human insulin.
B29-Nε-Acetyl-, B1-Nα-acetyl-human insulin.
B29-Nε-Acetyl-, A1-Nα-acetyl-human insulin.
A1-Nα-Acetyl-, B1-Nα-acetyl-human insulin.
B29-Nε-Acetyl-, A1-Nα-acetyl-, B1-Nα-acetyl-human insulin.
B29-Nε-Propionyl-human insulin.
B1-Nα-Propionyl-human insulin.
A1-Nα-Propionyl-human insulin.
B29-Nε-Propionyl-, B1-Nα-propionyl-human insulin.
B29-Nε-Propionyl-, A1-Nα-propionyl-human insulin.
A1-Nα-Propionyl-, B1-Nα-propionyl-human insulin.
B29-Nε-Propionyl-, A1-Nα-propionyl-, B1-Nα-propionyl-human insulin.
B29-Nε-Butyryl-human insulin.
B1-Nα-Butyryl-human insulin.
A1-Nα-Butyryl-human insulin.
B29-Nε-Butyryl-, B1-Nα-butyryl-human insulin.
B29-Nε-Butyryl-, A1-Nα-butyryl-human insulin.
A1-Nα-Butyryl-, B1-Nα-butyryl-human insulin.
B29-Nε-Butyryl-, A1-Nα-butyryl-, B1-Nα-butyryl-human insulin.
B29-Nε-Pentanoyl-human insulin.
B1-Nα-Pentanoyl-human insulin.
A1-Nα-Pentanoyl-human insulin.
B29-Nε-Pentanoyl-, B1-Nα-pentanoyl-human insulin.
B29-Nε-Pentanoyl-, A1-Nα-pentanoyl-human insulin.
A1-Nα-Pentanoyl-, B1-Nα-pentanoyl-human insulin.
B29-Nε-Pentanoyl-, A1-Nα-pentanoyl-, B1-Nα-pentanoyl-human insulin.
B29-Nε-Hexanoyl-human insulin.
B1-Nα-Hexanoyl-human insulin.
A1-Nα-Hexanoyl-human insulin.
B29-Nα-Hexanoyl-, B1-Nα-hexanoyl-human insulin.
B29-Nε-Hexanoyl-, A1-Nα-hexanoyl-human insulin.
A1-Nα-Hexanoyl-, B1-Nα-hexanoyl-human insulin.
B29-Nε-Hexanoyl-, A1-Nα-hexanoyl-, B1-Nα-hexanoyl-human insulin.
B29-Nε-Heptanoyl-human insulin.
B1-Nα-Heptanoyl-human insulin.
A1-Nα-Heptanoyl-human insulin.
B29-Nε-Heptanoyl-, B1-Nα-heptanoyl-human insulin.
B29-Nε-Heptanoyl-, A1-Nα-heptanoyl-human insulin.
A1-Nα-Heptanoyl-, B1-Nα-heptanoyl-human insulin.
B29-Nε-Heptanoyl-, A1-Nα-heptanoyl-, B1-Nα-heptanoyl-human insulin.
B29-Nε-Octanoyl-human insulin.
B1-Nα-Octanoyl-human insulin.
A1-Nα-Octanoyl-human insulin.
B29-Nε-Octanoyl-, B1-Nα-octanoyl-human insulin.
B29-Nε-Octanoyl-, A1-Nα-octanoyl-human insulin.
A1-Nα-Octanoyl-,B1-Nα-octanoyl-human insulin.
B29-Nε-Octanoyl-, A1-Nα-octanoyl-human insulin.
B29-Nε-Nonanoyl-human insulin.
B1-Nα-Nonanoyl-human insulin.
A1-Nα-Nonanoyl-human insulin.
B29-NεNonanoyl-, B1-Nα-nonanoyl-human insulin.
B29-Nε-Nonanoyl-, A1-Nα-nonanoyl-human insulin.
A1-Nα-Nonanoyl-, B1-Nα-nonanoyl-human insulin.
B29-Nε-Nonanoyl-, A1-Nα-nonanoyl-, B1-Nα-nonanoyl-human insulin.
B29-Nε-Decanoyl-human insulin.
B1-Nα-Decanoyl-human insulin.
A1-Nα-Decanoyl-human insulin.
B29-Nε-Decanoyl-, B1-Nα-decanoyl-human insulin.
B29-Nε-Decanoyl-, A1-Nα-decanoyl-human insulin.
A1-Nα-Decanoyl-, B1-Nα-decanoyl-human insulin.
B29-Nε-Decanoyl-, A1-Nα-decanoyl-, B1-Nα-decanoyl-human insulin.
B29-Nε-Undecanoyl-human insulin.
B1-Nα-Undecanoyl-human insulin.
A1-Nα-Undecanoyl-human insulin.
B29-Nε-Dodecanoyl-human insulin.

B1-Nα-Dodecanoyl-human insulin.
A1-Nα-Dodecanoyl-human insulin.
B29-Nε-Tridecanoyl-human insulin.
B1-Nα-Tridecanoyl-human insulin.
A1-Nα-Tridecanoyl-human insulin.
B29-Nε-Tetradecanoyl-human insulin.
B1-Nα-Tetradecanoyl-human insulin.
A1-Nα-Tetradecanoyl-human insulin.
B29-Nε-Pentadecanoyl-human insulin.
B1-Nα-Pentadecanoyl-human insulin.
A1-Nα-Pentadecanoyl-human insulin.
B29-Nε-Hexadecanoyl-human insulin.
B1-Nα-Hexadecanoyl-human insulin.
A1-Nα-Hexadecanoyl-human insulin.
B29-Nε-Heptadecanoyl-human insulin.
B1-Nα-Heptadecanoyl-human insulin.
A1-Nα-Heptadecanoyl-human insulin.
B29-Nε-Octadecanoyl-human insulin.
B1-Nα-Octadecanoyl-human insulin.
A1-Nα-Octadecanoyl-human insulin.
B28-Nε-Formyl-LysB28, ProB29-human insulin analog.
B1-Nα-Formyl-LysB28, ProB29-human insulin analog.
A1-Nα-Formyl-LysB28, ProB29-human insulin analog.
B28-Nε-Formyl-, B1-Nα-formyl-LysB28, ProB29-human insulin analog.
B28-Nε-Formyl-, A1-Nα-formyl-LysB28, ProB29-human insulin analog.
A1-Nα-Formyl-, B1-Nα-formyl-LysB28, ProB29-human insulin analog.
B28-Nε-Formyl-, A1-Nα-formyl-, B1-Nα-formyl-LysB28, ProB29-human insulin analog.
B28-Nε-Acetyl-LysB28, ProB29-human insulin analog.
B1-Nα-Acetyl-LysB28, ProB29-human insulin analog.
A1-Nα-Acetyl-LysB28, ProB29-human insulin analog.
B28-Nε-Acetyl-, B1-Nα-acetyl-LysB28, ProB29-human insulin analog.
B28-Nε-Acetyl-, A1-Nα-acetyl-LysB28, ProB29-human insulin analog.
A1-Nα-Acetyl-, B1-Nα-acetyl-LysB28, ProB29-human insulin analog.
B28-Nε-Acetyl-, A1-Nα-acetyl-, B1-Nα-acetyl-LysB28, ProB29-human insulin analog.
B28-Nε-Propionyl-LysB28, ProB29-human insulin analog.
B1-Nα-Propionyl-LysB28, ProB29-human insulin analog.
A1-Nα-Propionyl-LysB28, ProB29-human insulin analog.
B28-Nε-Propionyl-, B1-Nα-propionyl-LysB28, ProB29-human insulin analog.
B28-Nε-Propionyl-, A1-Nα-propionyl-LysB28, ProB29-human insulin analog.
A1-Nα-Propionyl-, B1-Nα-propionyl-LysB28, ProB29-human insulin analog.
B28-Nε-Propionyl-, A1-Nα-propionyl-, B1-Nα-propionyl-LysB28, ProB29-human insulin analog.
B28-Nε-Butyryl-LysB28, ProB29-human insulin analog.
B1-Nα-Butyryl-LysB28, ProB29-human insulin analog.
A1-Nα-Butyryl-LysB28, ProB29-human insulin analog.
B28-Nα-Butyryl-, B1-Nα-butyryl-LysB28, ProB29-human insulin analog.
B28-Nε-Butyryl-, A1-Nα-butyryl-LysB28, ProB29-human insulin analog.
A1-Nα-Butyryl-, B1-Nα-butyryl-LysB28, ProB29-human insulin analog.
B28-Nε-Butyryl-, A1-Nα-butyryl-, B1-Nα-butyryl-LysB28, ProB29-human insulin analog.
B28-Nε-Pentanoyl-LysB28, ProB29-human insulin analog.
B1-Nα-Pentanoyl-LysB28, ProB29-human insulin analog.
A1-Nα-Pentanoyl-LysB28, ProB29-human insulin analog.
B28-Nε-Pentanoyl-, B1-Nα-pentanoyl-LysB28, ProB29-human insulin analog.
B28-Nε-Pentanoyl-, A1-Nα-pentanoyl-LysB28, ProB29-human insulin analog.
A1-Nα-Pentanoyl-, B1-Nα-pentanoyl-LysB28, ProB29-human insulin analog.
B28-Nε-Pentanoyl-, A1-Nα-pentanoyl-, B1-Nα-pentanoyl-LysB28, ProB29-human insulin analog.
B28-Nε-Hexanoyl-LysB28, ProB29-human insulin analog.
B1-Nα-Hexanoyl-LysB28, ProB29-human insulin analog.
A1-Nα-Hexanoyl-LysB28, ProB29-human insulin analog.
B28-Nε-Hexanoyl-, B1-Nα-hexanoyl-LysB28, ProB29-human insulin analog.
B28-Nε-Hexanoyl-, A1-Nα-hexanoyl-LysB28, ProB29-human insulin analog.
A1-Nα-Hexanoyl-, B1-Nα-hexanoyl-LysB28, ProB29-human insulin analog.
B28-Nε-Hexanoyl-, A1-Nα-hexanoyl-, B1-Nα-hexanoyl-LysB28, ProB29-human insulin analog.
B28-Nε-Heptanoyl-LysB28, ProB29-human insulin analog.
B1-Nα-Heptanoyl-LysB28, ProB29-human insulin analog.
A1-Nα-Heptanoyl-LysB28, ProB29-human insulin analog.
B28-Nε-Heptanoyl-, B1-Nα-heptanoyl-LysB28, ProB29-human insulin analog.
B28-Nε-Heptanoyl-, A-Nα-heptanoyl-LysB28, ProB29-human insulin analog.
A1-Nα-Heptanoyl-, B1-Nα-heptanoyl-LysB28, ProB29-human insulin analog.
B28-Nε-Heptanoyl-, A1-Nα-heptanoyl-, B1-Nα-heptanoyl-LysB28, ProB29-human insulin analog.
B28-Nε-Octanoyl-LysB28, ProB29-human insulin analog.
B1-Nα-Octanoyl-LysB28, ProB29-human insulin analog.
A1-Nα-Octanoyl-LysB28, ProB29-human insulin analog.
B28-Nε-Octanoyl-, B1-Nα-octanoyl-LysB28, ProB29-human insulin analog.
B28-Nε-Octanoyl-, A1-Nα-octanoyl-LysB28, ProB29-human insulin analog.
A1-Nα-Octanoyl-, B1-Nα-octanoyl-LysB28, ProB29-human insulin analog.
B28-Nε-Octanoyl-, A1-Nα-octanoyl-, B1-Nα-octanoyl-LysB28, ProB29-human insulin analog.

B28-Nε-Nonanoyl-LysB28, ProB29-human insulin analog.

B1-Nα-Nonanoyl-LysB28, ProB29-human insulin analog.

A1-Nα-Nonanoyl-LysB28, ProB29-human insulin analog.

B28-Nε-Nonanoyl-, B1-Nα-nonanoyl-LysB28, ProB29-human insulin analog.

B28-Nε-Nonanoyl-, A1-Nα-nonanoyl-LysB28, ProB29-human insulin analog.

A1-Nα-Nonanoyl-, B1-Nα-nonanoyl-LysB28, ProB29-human insulin analog.

B28-Nε-Nonanoyl-, A1-Nα-nonanoyl-, B1-Nα-nonanoyl-LysB28, ProB29-human insulin analog.

B28-Nε-Decanoyl-LysB28, ProB29-human insulin analog.

B1-Nα-Decanoyl-LysB28, ProB29-human insulin analog.

A1-Nα-Decanoyl-LysB28, ProB29-human insulin analog.

B28-Nε-Decanoyl-, B1-Nα-decanoyl-LysB28, ProB29-human insulin analog.

B28-Nε-Decanoyl-, A1-Nα-decanoyl-LysB28, ProB29-human insulin analog.

A1-Nα-Decanoyl-, B1-Nα-decanoyl-LysB28, ProB29-human insulin analog.

B28-Nε-Decanoyl-, A1-Nα- decanoyl-, B1-Nα-decanoyl-LysB28, ProB29-human insulin analog.

B28-Nε-Undecanoyl-LysB28, ProB29-human insulin analog.

B1-Nα-Undecanoyl-LysB28, ProB29-human insulin analog.

A1-Nα-Undecanoyl-LysB28, ProB29-human insulin analog.

B28-Nε-Dodecanoyl-LysB28, ProB29-human insulin analog.

B1-Nα-Dodecanoyl-LysB28, ProB29-human insulin analog.

A1-Nα-Dodecanoyl-LysB28, ProB29-human insulin analog.

B28-Nε-Tridecanoyl-LysB28, ProB29-human insulin analog.

B1-Nα-Tridecanoyl-LysB28, ProB29-human insulin analog.

A1-Nα-Tridecanoyl-LysB28, ProB29-human insulin analog.

B28-Nε-Tetradecanoyl-LysB28, ProB29-human insulin analog.

B1-Nα-Tetradecanoyl-LysB28, ProB29-human insulin analog.

A1-Nα-Tetradecanoyl-LysB28, ProB29-human insulin analog.

B28-Nε-Pentadecanoyl-LysB28, ProB29-human insulin analog.

B1-Nα-Pentadecanoyl-LysB28, ProB29-human insulin analog.

A1-Nα-Pentadecanoyl-LysB28, ProB29-human insulin analog.

B28-Nε-Hexadecanoyl-LysB28, ProB29-human insulin analog.

B1-Nα-Hexadecanoyl-LysB28, ProB29-human insulin analog.

A1-Nα-Hexadecanoyl-LysB28, ProB29-human insulin analog.

B28-Nε-Heptadecanoyl-LysB28, ProB29-human insulin analog.

B1-Nα-Heptadecanoyl-LysB28, ProB29-human insulin analog.

A1-Nα-Heptadecanoyl-LysB28, ProB29-human insulin analog.

B28-Nε-Octadecanoyl-LysB28, ProB29-human insulin analog.

B1-Nα-Octadecanoyl-LysB28, ProB29-human insulin analog.

A1-Nα-Octadecanoyl-LysB28, ProB29-human insulin analog.

B29-Nε-Pentanoyl-GlyA21, ArgB31, ArgB32-human insulin.

B1-Nα-Hexanoyl-GlyA21, ArgB31, ArgB32-human insulin.

A1-Nα-Heptanoyl-GlyA21, ArgB31, ArgB32-human insulin.

B29-Nε-Octanoyl-, B1-Nα-octanoyl-GlyA21, ArgB31, ArgB32-human insulin.

B29-Nε-Propionyl-, A1-Nα-propionyl-GlyA21, ArgB31, ArgB32-human insulin.

A1-Nα-Acetyl, B1-Nα-acetyl-GlyA21, ArgB31, ArgB32-human insulin.

B29-Nε-Formyl-, A1-Nα-formyl-, B1-Nα-formyl-GlyA21, ArgB31, ArgB32-human insulin.

B29-Nε-Formyl-des(TyrB26)-human insulin.

B1-Nα-Acetyl-AspB28-human insulin.

B29-Nε-Propionyl-, A1-Nα-propionyl-, B1-Nα-propionyl-AspB1, AspB3, AspB21-human insulin.

A1-Nα-Butyryl-AspB10-human insulin.

B29-Nε-Pentanoyl-GlyA21-human insulin.

B1-Nα-Hexanoyl-GlyA21-human insulin.

A1-Nα-Heptanoyl-GlyA21-human insulin.

B29-Nε-Octanoyl-, B1-Nα-octanoyl-GlyA21-human insulin.

B29-Nε-Propionyl-, A1-Nα-propionyl-GlyA2l-human insulin.

A1-Nα-Acetyl, B1-Nα-acetyl-GlyA21-human insulin.

B29-Nε-Formyl-, A1-Nα-formyl-, B1-Nα-formyl-GlyA21-human insulin.

B29-Nε-Butyryl-des(ThrB30)-human insulin.

B1-Nα-Butyryl-des(ThrB30)-human insulin.

A1-Nα-Butyryl-des(ThrB30)-human insulin.

B29-Nε-Butyryl-, B1-Nα-butyryl-des(ThrB30)-human insulin.

B29-Nε-Butyryl-, A1-Nα-butyryl-des(ThrB30)-human insulin.

A1-Nα-Butyryl-, B1-Nα-butyryl-des(ThrB30)-human insulin.

B29-Nε-Butyryl-, A1-Nα-butyryl-, B1-Nα-butyryl-des(ThrB30)-human insulin.

Aqueous compositions containing water as the major solvent are preferred. Aqueous suspensions wherein water is the solvent are highly preferred.

The compositions of the present invention are used to treat patients who have diabetes or hyperglycemia. The formulations of the present invention will typically provide derivatized protein at concentrations of from about 1 mg/mL to about 10 mg/mL. Present formulations of insulin products are typically characterized in terms of the concentration of units of insulin activity (units/mL), such as U40, U50, U100, and so on, which correspond roughly to about 1.4, 1.75, and 3.5 mg/mL preparations, respectively. The dose, route of administration, and the number of administrations per day will be determined by a physician considering such factors as the therapeutic objectives, the nature and cause of the patient's disease, the patient's gender and weight, level of exercise, eating habits, the method of administration, and other factors known to the skilled physician. In broad range, a daily dose would be in the range of from about 1 nmol/kg body weight to about 6 nmol/kg body weight (6 nmol is considered equivalent to about 1 unit of insulin activity). A dose of between about 2 and about 3 nmol/kg is typical of present insulin therapy.

The physician of ordinary skill in treating diabetes will be able to select the therapeutically most advantageous means to administer the formulations of the present invention. Parenteral routes of administration are preferred. Typical routes of parenteral administration of suspension formulations of insulin are the subcutaneous and intramuscular routes. The compositions and formulations of the present invention may also be administered by nasal, buccal, pulmonary, or occular routes.

Glycerol at a concentration of 12 mg/mL to 25 mg/mL is preferred as an isotonicity agent. Yet more highly preferred for isotonicity is to use glycerol at a concentration of from about 15 mg/mL to about 17 mg/mL.

M-cresol and phenol, or mixtures thereof, are preferred preservatives in formulations of the present invention.

Insulin, insulin analogs, or proinsulins used to prepare derivatized proteins can be prepared by any of a variety of recognized peptide synthesis techniques including classical (solution) methods, solid phase methods, semi-synthetic methods, and more recent recombinant DNA methods. For example, see Chance, R. E., et al., U.S. Pat. No. 5,514,646, May 7, 1996; EPO publication number 383,472, Feb. 7, 1996; Brange, J. J. V., et al. EPO publication number 214,826, Mar. 18, 1987; and Belagaje, R. M., et al., U.S. Pat. No. 5,304,473, Apr. 19, 1994, which disclose the preparation of various proinsulin and insulin analogs. These references are expressly incorporated herein by reference.

Generally, derivatized proteins are prepared using methods known in the art. The publications listed above to describe derivatized proteins contain suitable methods to prepare derivatized proteins. Those publications are expressly incorporated by reference for methods of preparing derivatized proteins. To prepare acylated proteins, the protein is reacted with an activated organic acid, such as an activated fatty acid. Activated fatty acids are derivatives of commonly employed acylating agents, and include activated esters of fatty acids, fatty acid halides, activated amides of fatty acids, such as, activated azolide derivatives [Hansen, L. B., WIPO Publication No. 98/02460, Jan. 22, 1998], and fatty acid anhydrides. The use of activated esters, especially N-hydroxysuccinimide esters of fatty acids, is a particularly advantageous means of acylating a free amino acid with a fatty acid. Lapidot, et al. describe the preparation of N-hydroxysuccinimide esters and their use in the preparation of N-lauroyl-glycine, N-lauroyl-L-serine, and N-lauroyl-L-glutamic acid. The term "activated fatty acid ester" means a fatty acid which has been activated using general techniques known in the art [Riordan, J. F. and Vallee, B. L., *Methods in Enzymology, XXV*:494–499 (1972); Lapidot, Y., et al., *J. Lipid Res.* 8:142–145 (1967)]. Hydroxybenzotriazide (HOBT), N-hydroxysuccinimide and derivatives thereof are particularly well known for forming activated acids for peptide synthesis.

To selectively acylate the $\epsilon$-amino group, various protecting groups may be used to block the $\alpha$-amino groups during the coupling. The selection of a suitable protecting group is known to one skilled in the art and includes p-methoxybenzoxycarbonyl (pmZ). Preferably, the $\epsilon$-amino group is acylated in a one-step synthesis without the use of amino-protecting groups. A process for selective acylation at the N$\epsilon$-amino group of Lys is disclosed and claimed by Baker, J. C., et al., U.S. Pat. No. 5,646,242, Jul. 8, 1997, the entire disclosure of which is incorporated expressly by reference. A process for preparing a dry powder of an acylated protein is disclosed and claimed by Baker, J. C., et al., U.S. Pat. No. 5,700,904, Dec. 23, 1997, the entire disclosure of which is incorporated herein expressly by reference.

The primary role of zinc in the present invention is to facilitate formation of Zn(II) hexamers of the protein and derivatized protein, either separately as mixed hexamers, or together as hybrid hexamers. Zinc facilitates the formation of hexamers of insulin, and of insulin analogs. Zinc likewise promotes the formation of hexamers of derivatized insulin and insulin analogs. Hexamer formation is conveniently achieved by bringing the pH of a solution comprising protein, or derivatized protein, or both into the neutral region in the presence of Zn(II) ions, or by adding Zn(II) after the pH has been adjusted to the neutral region.

For efficient yield of microcrystals or amorphous precipitate, the molar ratio of zinc to total protein in the microcrystal and amorphous precipitate of the present invention is bounded at the lower limit by about 0.33, that is, the approximately two zinc atoms per hexamer which are needed for efficient hexamerization. The microcrystal and amorphous precipitate compositions will form suitably with about 2 to about 4–6 zinc atoms present when no compound that competes with insulin for zinc binding is present. Even more zinc may be used during the process if a compound that competes with the protein for zinc binding, such as one containing citrate or phosphate, is present. Excess zinc above the minimum amount needed for efficient hexamerization may be desirable to more strongly drive hexamerization. Also, excess zinc above the minimum amount can be present in a formulation of the present invention, and may be desirable to improve chemical and physical stability, to improve suspendability, and possibly to further extend time-action. Consequently, there is a fairly wide range of zinc:protein ratios allowable in the insoluble compositions, processes, and formulations of the present invention.

In accordance with the present invention, zinc is present in the formulation in an amount of from about 0.3 mole to about 7 moles per mole of total protein and more preferably about from 0.3 mole to about 1.0 mole of total protein. Yet more highly preferred is a ratio of zinc to derivatized protein from about 0.3 to about 0.7 mole of zinc atoms per mole of total protein. Most highly preferred is a ratio of zinc to total protein from about 0.30 to about 0.55 mole of zinc atoms per mole of total protein. For higher zinc formulations that are similar to PZI preparations, the zinc ratio is from about 5 to about 7 moles of zinc per mole of total protein.

The zinc compound that provides zinc for the present invention may be any pharmaceutically acceptable zinc compound. The addition of zinc to insulin preparations is known in the art, as are pharmaceutically acceptable sources of zinc. Preferred zinc compounds to supply zinc for the present invention include zinc chloride, zinc acetate, zinc citrate, zinc oxide, and zinc nitrate.

A complexing compound is required for the microcrystals and precipitates of the present invention. The complexing compound must be present in sufficient quantities to cause substantial precipitation and crystallization of the hexamers. Such quantities can be readily determined for a particular preparation of a particular complexing compound by simple titration experiments. Ideally, the complexing compound concentration is adjusted so that there is negligible complexing compound remaining in the soluble phase after completion of precipitation and crystallization. This requires combining the complexing compound based on an experimentally determined "isophane" ratio. This ratio is expected to be very similar to that of NPH and NPL. However, it may be slightly different because derivatization may affect the nature of the protein-protamine interaction.

When protamine is the complexing compound, it is present in the microcrystal in an amount of from about 0.15 mg to about 0.5 mg per 3.5 mg of the total protein. The ratio of protamine to total protein is preferably from about 0.25 to about 0.40 (mg/mg). More preferably the ratio is from about 0.25 to about 0.38 (mg/mg). Preferably, protamine is in an amount of 0.05 mg to about 0.2 mg per mg of the total protein, and more preferably, from about 0.05 to about 0.15 milligram of protamine per milligram of total protein. Protamine sulfate is the preferred salt form of protamine for use in the present invention. When protamine sulfate, or other salt form of protamine is used, the mass of it to be used would have to be adjusted with respect to the mass of protamine free base that would be used for the same application by a factor equal to the ratio of the molecular weights of the salt form and protamine.

To further extend the time action of the compositions of the present invention or to improve their suspendability, additional protamine and zinc may be added after crystallization. Thus, also within the present invention are formulations having protamine at higher than isophane ratios. For these formulations, the protamine ratio is from 0.25 mg to about 0.5 mg of protamine per mg of total protein.

A required component of the microcrystals and precipitates of the present invention is a hexamer stabilizing compound. The structures of three hexameric conformations have been characterized in the literature, and are designated T6, T3R3, and R6. In the presence of hexamer stabilizing compound, such as various phenolic compounds, the R6 conformation is stabilized. Therefore, it is highly likely that hexamers are in the R6 conformation, or the T3R3 conformation in the crystals and precipitates produced in the presence of a hexamer stabilizing compound, such as phenol or m-cresol, among others. A wide range of hexamer stabilizing compounds are suitable. They must be present in sufficient proportions with respect to total protein to stabilize the R6 hexamer conformation. To accomplish this, at least 2 or at least 3 moles of hexamer stabilizing compound per hexamer are required for effective hexamer stabilization. It is preferred that at least 3 moles of hexamer stabilizing compound per hexamer be present in the microcrystals and precipitates of the present invention. The presence of higher ratios of hexamer stabilizing compound, at least up to 25 to 50-fold higher, in the se data clearly show that soluble
B29-Nε- prepared will not adversely affect hexamer stabilization.

In formulations of the present invention, a preservative may be present, especially if the formulation is intended to be sampled multiple times. As mentioned above, a wide range of suitable preservatives are known. Preferably, the preservative is present in the solution in an amount suitable to provide an antimicrobial effect sufficient to meet pharmacopoeial requirements.

Preferred preservatives are the phenolic preservatives, which are enumerated above. Preferred concentrations for the phenolic preservative are from about 2 mg to about 5 mg per milliliter of the aqueous suspension formulation. These concentrations refer to the total mass of phenolic preservatives because mixtures of individual phenolic preservatives are contemplated. Suitable phenolic preservatives include, for example, phenol, m-cresol, and methylparaben. Preferred phenolic compounds are phenol and m-cresol. Mixtures of phenolic compounds, such as phenol and m-cresol, are also contemplated and highly preferred. Examples of mixtures of phenolic compounds are 0.6 mg/mL phenol and 1.6 mg/mL m-cresol, and 0.7 mg/mL phenol and 1.8 mg/mL m-cresol.

The microcrystals of the present invention are preferably oblong-shaped, also known as "rod-like", single crystals that are comprised of a protein, a derivatized protein, a divalent cation, and including a complexing compound and a hexamer-stabilizing compound. The mean length of the microcrystals of the present invention preferably is within the range of 1 micron to 40 microns, and more preferably is within the size range of 3 microns to 15 microns.

A preferred composition comprises from about 3 mg to about 6 mg of protamine sulfate per 35 mg of total protein, and from about 0.1 to about 0.4 mg zinc per 35 mg of total protein. Another preferred composition comprises from about 10 mg to about 17 mg of protamine sulfate per 35 mg of total protein, and from about 2.0 to about 2.5 mg zinc per 35 mg of total protein. Another preferred composition comprises, per mL, protamine sulfate, 0.34–0.38 mg; zinc, 0.01–0.04 mg; and total protein, 3.2–3.8 mg.

Both an un-derivatized protein and a derivatized protein are required for the present co-crystals and amorphous precipitates. The ratio between the masses of these proteins determines the degree of time extension of the preparations. A preferred ratio of the number of moles of the protein to the number of moles of the derivatized protein is between about 1:100 and about 100:1. A further preferred ratio of the number of moles of the protein to the number of moles of the derivatized protein is between about 1:1 and about 100:1. Another preferred ratio of the number of moles of the protein to the number of moles of the derivatized protein is between about 1:1 and about 20:1. Yet other preferred ratios of the number of moles of the protein to the number of moles of the derivatized protein are: between about:2:1 and about 20:1; between about 2:1 and 10:1; between about 2:1 and 5:1; between about 3:1 and 5:1; between 1:1 and 1:20; between 1:1 and 1:10; between about 1:2 and about 1:20; between about 1:2 and 1:10; between about 1:2 and 1:5; between about 1:3 and 1:5; between about 10:1 and about 1:10; between about 9:1 and about 1:9; between about 5:1 and about 1:5; and between about 3:1 and about 1:3.

The present invention provides processes for preparing the compositions. Also, the use of the present insoluble compositions to prepare medicaments for controlling blood glucose, and for treating diabetes or hyperglycemia is contemplated. The amorphous precipitates and microcrystals of the present invention can be prepared for use in medicaments, or other uses, by many different processes.

In summary, suitable processes are comprised generally of the steps in one of the following sequences: solubilization (if starting with dry material), hexamerization, homogenization, complexation, precipitation, crystallization, and optionally formulation; or solubilization (if starting with dry material), homogenization, hexamerization, complexation, precipitation, crystallization, and optionally formulation.

Solubilization means the dissolution of derivatized protein and protein sufficiently to allow them to form hexamers. Hexamerization refers to the process wherein molecules of protein and derivatized protein bind with zinc(II) atoms to form hexamers. Complexation denotes the formation of insoluble complexes between the hexamers of dissolution of protamine-zinc-
B29-Nε-octanoyl-Lys
B29 formation of insoluble complexes. Crystallization involves of human insulin to
B29-Nε-octanoyl-Lys
B29 human insulin into crystals, typically, rod-like crystals.

Solubilization is carried out by dissolving the derivatized protein and protein in an aqueous solvent. The aqueous solvent may be, for example, an acidic solution, a neutral solution, or a basic solution. The aqueous solvent may be comprised partially of a miscible organic solvent, such as ethanol, acetonitrile, dimethylsulfoxide, and the like. Acidic solutions may be, for example, solutions of HCl, advantageously from about 0.01 N HCl to about 1.0 N HCl. Other acids that are pharmaceutically acceptable may be employed as well. Basic solutions may be, for example, solutions of NaOH, advantageously from about 0.01 N NaOH to about 1.0 N NaOH, or higher. Other bases that are pharmaceutically acceptable may be employed as well. For the sake of protein stability, the concentration of acid or base is preferably as low as possible while still being effective to adequately dissolve the protein and derivatized protein.

Most proteins (insulin, insulin analogs, and proinsulins) and many derivatized proteins may be dissolved to suitable concentrations at neutral pH. Solutions to dissolve derivatized proteins at neutral pH may contain a buffer and optionally, one or more additional solutes such as salts, phenolic compounds, zinc, and isotonicity agents.

When hexamerization occurs before homogenization, two populations of homogenous hexamers are formed first, and then the populations are mixed, thereby forming mixed hexamers. When homogenization occurs first, hexamerization yields hybrid hexamers. As mentioned above, to prepare insoluble compositions comprised of hybrid hexamers, protein and derivatized protein are homogenized under conditions favoring dissociation to monomer or dimer aggregation states prior to hexamerization with a divalent metal cation. To achieve the necessary dissociation, the protein and derivatized protein may be mixed under strongly acidic or strongly basic conditions. The degree of dissociation, and therefore, homogenization is influenced by the solution conditions chosen for this step. Insulin and related proteins readily self-associate in a series of reactions producing dimers, hexamers, and other associated forms. The distribution of these association forms at equilibrium is dependent on many parameters, including pH. These association reactions are commonly thought to involve primarily monomer-dimer-hexamer assembly. Consequently, depending on the solution conditions chosen, homogenization should accomplish the mixing of monomers, dimers, or a mixture thereof. Homogenization in 1 N HCl, for example, could involve a higher fraction of monomer mixing than in 0.1 N HCl, which would probably involve more dimer mixing. For the preparation of compositions comprised of hybrid hexamers, the homogenization process will be effective provided that only a very small or negligible fraction of homogeneous hexamers of the protein or derivatized protein exist under the homogenization conditions employed.

Compositions comprised of mixed hexamers incorporate predominantly two types of hexamers, namely hexamers of the protein, and hexamers of the derivatized protein. In this case, the homogenization step occurs after the hexamerization step, and achieves the homogenization of the hexamers prior to complexation with the complexing compound. Consequently, the homogenization step is performed under solution conditions that stabilize the Zn(II)-insulin hexamer. Solution conditions that stabilize insulin hexamers are well known in the literature.

The solution conditions required for hexamerization are those that allow the formation of the hybrid hexamers or mixed hexamers in solution. These conditions will be identical or very similar to the conditions under which insulin or insulin analogs are made to hexamerize. Typically, hexamerization requires zinc and a neutral to slightly basic pH, which is taken to be from about pH 6.8 to about pH 8.4. The presence of a hexamer-stabilizing compound advantageously influences hexamerization by promoting the R6 or the T3R3 conformations of the derivatized protein, and in certain instances, of the protein also. For certain monomeric insulin analogs, a hexamer-stabilizing compound is required to form hexamers.

For compositions comprised of hybrid hexamers, seven hexameric species are expected: $P_6$, $P_5D_1$, $P_4D_2$, $P_3D_3$, $P_2D_4$, $P_1D_5$, and $D_6$, where P represents the protein monomer, and D represents the derivatized protein monomer. The statistical distribution of hexamers is expected to conform to a Poisson distribution, and will be influenced by the relative proportion of protein and derivatized protein, and by the degree of dissociation prior to hexamerization. For example, from a homogenized solution constituted predominantly of dimers, four major hybrid hexamer species are expected: $P_6$, $P_4D_2$, $P_2D_4$, and $D_6$. For compositions comprised of mixed hexamers, only two hexameric species are expected to predominate: $P_6$ and $D_6$.

The complexation step must involve the combination a complexing compound with hexamer under solution conditions where each is initially soluble. This could be accomplished by combining separate solutions of hexamers and of protamine, or by first forming a solution of protein, derivatized protein, and protamine at acidic or basic pH, and then shifting the pH to the neutral range.

During crystallization, the solution conditions must stabilize the crystallizing species, and promote the conversion of precipitate to solute to crystal. Thus, the solution conditions will determine the rate and outcome of crystallization. Crystallization likely involves a complex equilibrium involving non-crystalline precipitate, dissolved hexamer-protamine complexes, and crystal. To obtain microcrystals, the conditions chosen for crystallization must drive the equilibrium toward crystal formation. Also, in light of the hypothesized equilibrium, the solubility of the derivatized protein is expected to profoundly affect crystallization rate and size because lower solubility will likely slow the net conversion from precipitate to solution to crystal. Furthermore, it is well-recognized that slowing the rate of crystallization often results in larger crystals. Thus, the crystallization rate and crystal size are thought to depend on the size and nature of the derivatizing moiety on the derivatized protein.

Crystallization parameters that influence the crystallization rate and the size of crystals of the present invention are: acyl group size and nature; temperature; the presence and concentration of compounds that compete with the protein and derivatized protein for zinc, such as citrate, phosphate, and the like; the nature and concentration of phenolic compound(s); zinc concentration; the presence and concentration of a miscible organic solvent; the time permitted for crystallization; the pH and ionic strength; buffer identity and concentration; the concentration of precipitants; the presence of seeding materials; the shape and material of the container; the stirring rate; and the total protein concentration. Temperature and the concentration of competing compounds are thought to be of particular importance.

Competing compounds, such as citrate, may affect the rate at which crystals form, and indirectly, crystal size and quality. These compounds may exert their effect by forming coordination complexes with zinc in solution, thus competing with the relatively weak zinc binding sites on the surface of the hexamer for zinc. Occupation of these weak surface binding sites probably impedes crystallization. Additionally, many derivatized proteins are partially insoluble in the presence of little more than 0.333 zinc per mole of derivatized protein, and the presence of competing compounds restores solubility, and permits crystallization. The optimum concentration of competing compound can be determined using routine techniques for any combination of protein and derivatized protein. As an upper limit, of course, is the concentration at which zinc is precipitated by the competing compound, or the concentration at which residual competing compound would be pharmaceutically unacceptable, such as, when it would cause pain or irritation at the site of administration.

An example of a process for preparing the precipitates and crystals of the present invention follows. A measured amount of the derivatized protein and a measured amount of the protein are dissolved in, or are combined to form a solution in an aqueous solvent containing a hexamer-stabilizing compound, such as a phenolic compound. To this solution is added a solution of zinc as one of its soluble salts, for example $Zn(II)Cl_2$, to provide from about 0.3 moles of zinc per mole of derivatized insulin to about 0.7 moles, or to as much as 1.0 moles, of zinc per mole of total protein (protein+derivatized protein). Absolute ethanol, or another miscible organic solvent, may optionally be added to this solution in an amount to make the solution from about 5% to about 10% by volume organic solvent. This solution may then be filtered through a 0.22 micron, low-protein binding filter. A protamine solution is prepared by dissolving a measured amount of protamine in an aqueous solvent. This solution may be filtered through a 0.22 micron, low-protein binding filter. The solution of protein and derivatized protein and the protamine solution are combined, whereupon a precipitate forms initially. The resulting suspension is stirred slowly at room temperature (typically about 20–25° C.), whereupon microcrystals are formed within a period from about 4 hours to about 10 days.

The microcrystals may then be separated from the mother liquor and introduced into a different solvent, for storage and administration to a patient. Examples of appropriate aqueous solvents are as follows: water for injection containing 25 mM TRIS, 5 mg/mL phenol and 16 mg/mL glycerol; water for injection containing 2 mg/mL sodium phosphate dibasic, 1.6 mg/mL m-cresol, 0.65 mg/mL phenol, and 16 mg/mL glycerol; and water for injection containing 25 mM TRIS, 5 mg/mL phenol, 0.1 M trisodium citrate, and 16 mg/mL glycerol.

In another process for preparing the insoluble compositions of the present invention, for example, a measured mass of dry derivatized protein and a measured mass of dry protein are dissolved together in an acidic aqueous solvent, such as 0.1 N–1.0 N HCl. This solution is stirred to insure thorough mixing of derivatized protein and protein. The ratio of derivatized protein powder to protein powder in this mixture is predefined to achieve a similar ratio of derivatized protein to protein in the insoluble composition to be produced. A separately prepared aqueous solution comprised of a phenolic preservative and, optionally, a pharmaceutically acceptable buffer, is combined with the acidic solution of the proteins. The pH of the resulting solution is then adjusted to about 6.8 to about 8.4, preferably from about 6.8 to about 8.0, or preferably to a pH of from about 7.2 to about 7.8, and most preferably from about 7.4 to about 7.8. To this solution is added a solution of zinc as one of its soluble salts, for example $Zn(II)Cl_{2,1}$ to provide from about 0.3 moles of zinc per mole of total insulin to about 4 moles of zinc per mole of total insulin. This solution is adjusted to a pH as given above, and preferably to about 7.4–7.6, and may then be filtered through a 0.22 micron, low-protein binding filter. A solution of protamine is prepared by dissolving a measured mass of protamine in an aqueous solvent. The protamine solution may be filtered through a 0.22 micron, low-protein binding filter. The solution of protein and derivatized protein and the protamine solution are combined, whereupon a precipitate forms initially. The resulting suspension is stirred slowly at room temperature (typically about 20–25° C.), whereupon microcrystals are formed within a period from about 4 hours to about 10 days.

In another process for preparing the insoluble compositions of the present invention, a measured amount of a derivatized protein is first dissolved in an aqueous solvent containing a phenolic preservative. To this solution is added a solution of zinc as one of its soluble salts, for example $Zn(II)Cl_2$, to provide from about 0.3 moles of zinc per mole of derivatized protein to about 4 moles of zinc per mole of derivatized protein. The pH of the resulting solution is then adjusted to about 6.8 to about 8.4, preferably from about 6.8 to about 8.0, or preferably to a pH of from about 7.2 to about 7.8, and most preferably from about 7.4 to about 7.8. A second solution is prepared separately wherein a measured amount of a protein selected from the group consisting of insulin, insulin analogs, and proinsulin is dissolved in an aqueous solvent containing a phenolic preservative. To this solution is added a solution of zinc as one of its soluble salts, for example $Zn(II)Cl_2$, to provide from about 0.3 moles of zinc per mole of protein to about 4 moles of zinc per mole of protein. The pH of the resulting solution is then adjusted to about 6.8 to about 8.4, preferably from about 6.8 to about 8.0, or preferably to a pH of from about 7.2 to about 7.8, and most preferably from about 7.4 to about 7.8, or 7.4–7.6. Portions of the derivatized protein solution and the protein solution are combined in a ratio that is predefined in order to achieve a similar ratio of derivatized protein to protein in the insoluble composition. This solution is stirred to insure thorough mixing of derivatized protein and protein. This solution is then adjusted to a pH of about 7.6, and may then be filtered through a 0.22 micron, low-protein binding filter. A protamine solution is prepared separately by dissolving a measured amount of protamine in an aqueous solvent. This protamine solution may be filtered through a 0.22 micron, low-protein binding filter. The solution of protein and derivatized protein and the protamine solution are combined, whereupon a precipitate forms initially. The resulting suspension is stirred slowly at room temperature (typically about 20–25° C.), whereupon microcrystals are formed within a period from about 4 hours to about 10 days.

While not describing all of the very many types of processes that will produce the insoluble compositions of the present invention in any way, the following are yet further processes of the present invention:

dissolving a protein, a derivatized protein, a hexamer-stabilizing compound, and a divalent metal cation in an aqueous solvent having a pH that will permit the formation of hexamers, and adding a complexing compound;

dissolving a protein, a derivatized protein, a hexamer-stabilizing compound, and a divalent metal cation in an aqueous solvent having a pH that will not permit the formation of hexamers, adjusting the pH to between about 6.8 and about 7.8, and adding a complexing compound;

dissolving a protein, a hexamer-stabilizing compound, and a divalent metal cation in an aqueous solvent having a pH that will permit the formation of hexamers, separately, dissolving a derivatized protein, a hexamer-stabilizing compound, and a divalent metal cation in an aqueous solvent having a pH that will permit the formation of hexamers, thoroughly mixing together these two solution, and then adding a complexing compound;

dissolving a protein, a hexamer-stabilizing compound, a divalent metal cation, and a complexing compound in an aqueous solvent, wherein the resulting solution has a pH at which precipitation does not occur, separately, dissolving a derivatized protein, a hexamer-stabilizing compound, a divalent metal cation, and a complexing compound in an aqueous solvent, wherein the resulting solution has a pH at which precipitation does not occur, thoroughly mixing together these two solutions, and adjusting the pH of the solution of to a value at which precipitation occurs;

dissolving a protein, a derivatized protein, a hexamer-stabilizing compound, a divalent metal cation, and a complexing compound in an aqueous solvent, wherein the resulting solution has a pH at which precipitation does not occur and adjusting the pH of the solution to a value at which precipitation occurs;

dissolving a protein, a derivatized protein, a hexamer-stabilizing compound, and a divalent metal cation, in an aqueous solvent, wherein the resulting solution has a pH at which precipitation will not occur when a complexing agent is added, adding a complexing compound, and adjusting the pH of the solution of step b) to a value at which precipitation occurs;

dissolving a protein, a hexamer-stabilizing compound, and a divalent metal cation in an aqueous solvent, wherein the resulting solution has a pH at which precipitation will not occur when a complexing compound is added, separately, dissolving a derivatized protein, a hexamer-stabilizing compound, and a divalent metal cation in an aqueous solvent, wherein the resulting solution has a pH at which precipitation will not occur when a complexing compound is added, thoroughly mixing together these two solutions, adding complexing compound to the solution, and adjusting the pH to a value at which precipitation occurs;

dissolving a protein, a protein derivative, a hexamer-stabilizing compound, and a divalent metal cation in an aqueous solvent, wherein the resulting solution has a pH at which precipitation will not occur when a complexing compound is added, adjusting the pH of the solution to a value at which precipitation will occur when a complexing compound is added, and adding a complexing compound to the solution;

dissolving a protein, a hexamer-stabilizing compound, and a divalent metal cation in an aqueous solvent, wherein the resulting solution has a pH at which precipitation will not occur when a complexing compound is added, separately, dissolving a derivatized protein, a hexamer-stabilizing compound, and a divalent metal cation in an aqueous solvent, wherein the resulting solution has a pH at which precipitation will not occur when a complexing compound is added; thoroughly mixing together these two solutions, adjusting the pH of the solution of step c) to a value at which precipitation will occur when a complexing compound is added, and adding a complexing compound to the solution;

In a preferred embodiment, the microcrystals are prepared in a manner that obviates the need to separate the microcrystals from the mother liquor. Thus, it is preferred that the mother liquor itself be suitable for administration to the patient, or that the mother liquor can be made suitable for administration by dilution with a suitable diluent. The term diluent will be understood to mean a solution comprised of an aqueous solvent in which is dissolved various pharmaceutically acceptable excipients, including without limitation, a buffer, an isotonicity agent, zinc, a preservative, protamine, and the like.

In addition to the protein, derivatized protein, divalent cation, complexing compound, and hexamer-stabilizing compound, pharmaceutical compositions adapted for parenteral administration in accordance with the present invention may employ additional excipients and carriers such as water miscible organic solvents such as glycerol, sesame oil, aqueous propylene glycol and the like. When present, such agents are usually used in an amount less than about 2.0% by weight based upon the final formulation. For further information on the variety of techniques using conventional excipients or carriers for parenteral products, please see Remington's Pharmaceutical Sciences, 17th Edition, Mack Publishing Company, Easton, Pa., USA (1985), which is incorporated herein by reference.

In the broad practice of the present invention, it is also contemplated that a formulation may contain a mixture of the microcrystals and a soluble fraction of a protein selected from insulin, derivatized insulin, insulin analogs, and derivatized insulin analogs. Examples of such pharmaceutical compositions include sterile, isotonic, aqueous saline solutions of insulin, an insulin analog, a derivatized insulin, or a derivatized insulin analog, buffered with a pharmaceutically acceptable buffer and pyrogen-free. Preferred for the soluble phase are insulin or a rapid-acting insulin analog, such as, LysB28, ProB29-human insulin, or AspB28-human insulin. Such mixtures are designed to provide a combination of meal-time control of glucose levels, which is provided by the soluble insulin, and basal control of glucose levels, which is provided by the insoluble insulin. The ratio of total protein (protein plus derivatized protein) in the insoluble phase and total protein in the soluble phase is in the range of about 9:1 to about 1:9. A preferred range of this ratio is from about 9:1 to about 1:1, and more preferably, about 7:3. Other ratios are 1:1, and 3:7.

The following preparations and examples illustrate and explain the invention. The scope of the invention is not limited to these preparations and examples. Reference to "parts" for solids means parts by weight. Reference to "parts" for liquids means parts by volume. Percentages, when used to express concentration, mean mass per volume (×100). All temperatures are degrees Centigrade (° C.). "TRISO" refers to 2-amino-2-hydroxymethyl-1,3,-propanediol. The 1000 part-per-million (ppm) zinc solution was prepared by diluting 1.00 mL of a 10,000 ppm zinc atomic absorption standard solution [Ricca Chemical Company, zinc in dilute nitric acid] with water to a final volume of 10.00 mL.

In many of the preparations described below, the yield of precipitates and crystals was estimated. The yield estimate relied on determination of the amount of total protein in the precipitate or crystal, and on an estimate of the amount of same initially in solution. To determine the amount of total protein, samples of re-dissolved precipitate or crystal, and of the supernatant above the precipitate or crystals, were analyzed by reversed-phase gradient HPLC, as described below.

Briefly, the analytical system relied on a C8 reversed-phase column, at 23° C. The flow rate was 1.0 mL/min and UV detection at 214 nm was used. Solvent A was 0.1% (vol:vol) trifluroacetic acid in 10:90 (vol:vol) acetonitrile:water. Solvent B was 0.1t (vol:vol) trifluroacetic acid in 90:10 (vol:vol) acetonitrile:water. The development program was (minutes, %B): (0.1,0); (45.1,75); (50.1,100); (55,100); (57,0); (72,0). All changes were linear. Other analytical systems could be devised by the skilled person to achieve the same objective.

To prepare for the HPLC analysis, aliquots of the well-mixed suspensions were dissolved by diluting with either 0.01 N HCl or 0.03 N HCl. Results of HPLC analysis of these solutions permitted calculation of total protein. Aliquots of the suspensions were centrifuged for approximately 5 minutes in an Eppendorf 5415C microcentrifuge at 14,000 rpm. The decanted supernatant was diluted with either 0.01 N or 0.03 N HCl and analyzed by HPLC. The precipitate was washed by re-suspending in Dulbecco's phosphate buffered saline (without calcium or magnesium) and re-pelleted by centrifugation. The buffer was decanted and the solid was re-dissolved in 0.01 N HCl. The re-dissolved precipitate was analyzed by HPLC.

HPLC was used to confirm the presence of the expected proteins in the acidified suspension, re-dissolved precipitate, and supernatant and also to determine protein concentrations. The retention times of peaks in the chromatograms of the re-dissolved precipitates were compared with the retention times observed for protamine and the active compounds used to make the formulations. The agreement between retention times was always good, showing that protamine, protein, and derivatized proteins were actually incorporated into the microcrystals. Concentrations of protein and derivatized protein were determined by comparing the appropriate peak areas to the areas of a standard. A 0.22 mg/mL solution of derivatized insulin was used as the standard. A standard containing protamine was run, but only for the purpose of determining the retention time. Protamine concentration was not quantitated.

In many of the preparations described below, a standard spectrophotometric assay was used to determine how rapidly the crystals dissolved in Dulbecco's phosphate buffered saline (pH 7.4) at room temperature. Significant deviations from the procedure described immediately below are noted where appropriate in the descriptions of the preparations. A spectrophotometer suitable for measuring in the ultraviolet range, and equipped with a 1 cm cuvette and a magnetic cuvette stirrer was used for all the dissolution assays. The cuvette, containing a small stir bar and 3.00 mL of phosphate buffered saline (PBS), was put into the cell compartment of the spectrophotometer. The instrument was set to 320 nm and zeroed against the same buffer. Then 4.0 microliters of a well suspended formulation, usually having a total concentration approximately equivalent to a U50 formulation, or about 1.6 to 1.8 mg/mL, was added to the cuvette. After waiting 1.0 minute for mixing, the optical density at 320 nm was recorded. Since the proteins involved in this work do not absorb light at 320 nm, the decrease in optical density was due to reduction in light scattering as the crystals dissolved. The time for the optical density to drop to half of its initial value is typically reported (t1/2). As a control, 2.0 microliters of U100 Humulin® N (i.e., human insulin NPH, which is also known as human NPH density at 320 nm monitored as above. The dissolution half-time (t1/2) for the Humulin® N formulation was about 6 minutes.

PREPARATION 1

9:1 Co-crystals of Human Insulin and B29-Nε-octanoyl-human Insulin

A dry powder of B29-Nε-octanoyl-LysB29 human insulin (0.7 parts by mass) and a dry powder of human insulin (6.3 parts by mass) are dissolved in 1000 parts by volume of an aqueous solvent composed of 50 mM TRIS, 0.1 M trisodium citrate, and 10 mg/ml phenol at pH 7.6. To this solution is added 75 parts of a 15.3 mM solution of zinc chloride. The pH is adjusted to 7.6 with 1 N HCl and/or 1 N NaOH. This solution is filtered through a 0.22 micron, low-protein binding filter. A second solution is prepared by dissolving 7 parts by mass of protamine sulfate in 10,000 parts by volume of water then filtering through a 0.22 micron, low-protein binding filter. Equal volumes of the solution containing insulin and acylated insulin and of the protamine sulfate solution are combined. Initially, an amorphous precipitate forms. This suspension is allowed to stand for about 24 hours at room temperature (typically about 22° C.). The amorphous precipitate converts to a co-crystalline microcrystalline solid.

PREPARATION 2

3:1 Co-crystals of Human Insulin and B29-Nε-Octanoyl-human Insulin

The procedure of Preparation 1 is followed, except that 1.75 parts by mass of a dry powder of B29-Nε-octanoyl-LysB29 human insulin and 5.25 parts by mass of a dry powder of human insulin are used. After equal volumes of the solution containing insulin and acylated insulin and of the protamine sulfate solution are combined, an amorphous precipitate forms. This suspension is allowed to stand for about 24 hours at room temperature (typically about 22° C.). The amorphous precipitate converts to a co-crystalline microstalline solid.

PREPARATION 3

Formulation of 3:1 Co-crystals of human insulin and B29-Nε-Octanoyl-human Insulin The co-crystalline microcrystals prepared by the method of Preparation 1 are separated from the supernatant and are recovered by conventional solid/liquid separation methods, such as, filtration, centrifugation, or decantation. The recovered co-crystalline microcrystals are then suspended in a solution consisting of 25 mM TRIS, 5 mg/ml phenol, and 16 mg/ml glycerol, pH 7.8, so that the final concentration of insulin activity is about 100 U/mL.

PREPARATION 4

1:1 co-crystals of Human Insulin and B29-Nε-Octanoyl-human Insulin

The procedure of Preparation 1 is followed, except that 3.5 parts by mass of a dry powder of B29-Nε-octanoyl-LysB29 human insulin and 3.5 parts by mass of a dry powder of human insulin are used. After equal volumes of the solution containing insulin and acylated insulin and of the protamine sulfate solution are combined, an amorphous precipitate forms. This suspension is allowed to stand for about 24 hours at room temperature (typically about 22° C.). The amorphous precipitate converts to a co-crystalline microcrystalline solid.

PREPARATION 5

1:3 Co-crystals of human insulin and B29-Nε-Octanoyl-human Insulin

The procedure of Preparation 1 is followed, except that 5.25 parts by, mass of a dry powder of B29-Nε-octanoyl-LysB29 human insulin and 1.75 parts by mass of a dry powder of human insulin are used. After equal volumes of the solution containing insulin and acylated insulin and of the protamine sulfate solution are combined, an amorphous recipitate forms. This suspension is allowed to stand for about 24 hours at room temperature (typically about 22° C.). The amorphous precipitate converts to a co-crystalline microcrystalline solid.

PREPARATION 6

3:1 Co-crystals of Human Insulin and B29-Nε-Hexanoyl-human Insulin

The procedure of Preparation 1 is followed, except that 1.75 parts by mass of a dry powder of B29-Nε-hexanoyl-LysB29 human insulin and 5.25 parts by mass of a dry powder of human insulin are used. After equal volumes of the solution containing insulin and acylated insulin and of the protamine sulfate solution are combined, an amorphous precipitate forms. This suspension is allowed to stand for about 24 hours at room temperature (typically about 22° C.). The amorphous precipitate will convert to a co-crystalline microcrystalline solid.

PREPARATION 7

3:1 Co-crystals of Human Insulin and B29-Nε-Butyryl-human Insulin

The procedure of Preparation 1 is followed, except that 1.75 parts by mass of a dry powder of B29-Nε-butyryl-LysB29 human insulin and 5.25 parts by mass of a dry powder of human insulin are used. After equal volumes of the solution containing insulin and acylated insulin and of the protamine sulfate solution are combined, an amorphous precipitate forms. This suspension is allowed to stand for about 24 hours at room temperature (typically about 22° C.). The amorphous precipitate will convert to a co-crystalline microcrystalline solid.

PREPARATION 8

Co-crystalline Microcrystals of Protamine-zinc-B29-Nε-octanoyl-human Insulin-human Insulin B29-Nε-octanoyl-LysB29 human insulin (20.1 mg) was dissolved in 1 mL of a solvent composed of 0.1 N HCl. Human insulin (19.3 mg) was dissolved in 1 mL of a solvent composed of 0.1 N HCl. Five solutions comprising different ratios of B29-Nε-octanoyl-LysB29 human insulin to human insulin were prepared by combining volumes of each solution in the ratios shown below.

TABLE 3

Volumes of solutions of human insulin and of B29-Nε-octanoyl-human insulin used to prepare precipitates and microcrystals.

| | Ratio of Human Insulin to Acylated Human Insulin | | | | |
|---|---|---|---|---|---|
| Volume (μl) | 1:0 | 3:1 | 1:1 | 1:3 | 0:1 |
| Human insulin solution | 400 | 300 | 200 | 100 | 0 |
| B29-Nε-octanoyl-human insulin solution | 0 | 100 | 200 | 300 | 400 |

To each of these five solutions, 1.6 mL of a solvent composed of 50 mM TRIS buffer, 0.1 M trisodium citrate, and 10 mg/mL phenol at pH 7.6 was added. To each of the five solutions, 0.15 ml of a 15.3 mM solution of zinc chloride was added. Each of the resulting five solutions were adjusted to a pH of 7.6 with 1 N NaOH. Each of the resulting five solutions were filtered through a 0.22 micron, low-protein binding filter. An additional solution was prepared by dissolving 3.50 mg of protamine sulfate in 10 mL of water then filtered through a 0.22 micron, low-protein binding filter. A volume of 1.9 mL of each of the five solutions and 1.9 mL of the protamine sulfate solution were combined respectively, in each of the five solutions resulting in the immediate appearance of an amorphous precipitate. These five solutions were allowed to stand for 24 hours at room temperature (approximately 22° C.). This procedure resulted in the formation of a white-to-off-white microcrystalline solid in each of the five solutions.

PREPARATION 9

9:1 Co-crystals of Human Insulin and B29-Nε-Octanoyl-human Insulin

A dry powder of B29-Nε-octanoyl-LysB29 human insulin (0.7 parts by mass) is dissolved in 100 parts by volume of an aqueous solvent composed of 50 mM TRIS, 0.1 M trisodium citrate, and 10 mg/ml phenol at pH 7.6. To this solution is added 7.5 parts of a 15.3 mM solution of zinc chloride. A second solution is prepared wherein a dry powder of human insulin (6.3 parts by mass) is dissolved in 900 parts by volume of an aqueous solvent composed of 50 mM TRIS, 0.1 M trisodium citrate, and 10 mg/ml phenol at pH 7.6. To this solution is added 67.5 parts of a 15.3 mM solution of zinc chloride. The acylated insulin solution and the insulin solution are combined together and stirred to insure mixing of the two solutions. This solution is filtered through a 0.22 micron, low-protein binding filter. A protamine solution is prepared by dissolving 7 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is allowed to stand for about 24 hours at room temperature (typically about 22° C.). The amorphous precipitate will convert to a co-crystalline microcrystalline solid.

PREPARATION 10

3:1 Co-crystals of Human Insulin and B29-Nε-Octanoyl-human Insulin

A dry powder of B29-Nε-octanoyl-LysB29 human insulin. (1.75 parts by mass) is dissolved in 250 parts by volume of an aqueous solvent composed of 50 mM TRIS, 0.1 M trisodium citrate, and 10 mg/ml phenol at pH 7.6. To this solution is added 18.75 parts of a 15.3 mM solution of zinc chloride. A second solution is prepared wherein a dry powder of human insulin (5.25 parts by mass) is dissolved in 750 parts by volume of an aqueous solvent composed of 50 mM TRIS, 0.1 M trisodium citrate, and 10 mg/ml phenol at pH 7.6., To this solution is added 56.25 parts of a 15.3 mM solution of zinc chloride. The acylated insulin solution and the insulin solution are combined together and stirred to insure mixing of the two solutions. This solution is filtered through a 0.22 micron, low-protein binding filter. A protamine solution is prepared by dissolving 7 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is allowed to stand for about 24 hours at room temperature (typically about 22° C.). The amorphous precipitate converts to a co-crystalline microcrystalline solid.

PREPARATION 11

1:1 Co-crystals of Human Insulin and B29-Nε-Octanoyl-human Insulin

A dry powder of B29-Nε-octanoyl-LysB29 human insulin (3.5 parts by mass) is dissolved in 500 parts by volume of an aqueous solvent composed of 50 mM TRIS, 0.1 M trisodium citrate, and 10 mg/ml phenol at pH 7.6. To this solution is added 1.75 parts of a 15.3 mM solution of zinc chloride. A second solution is prepared wherein a dry powder of human insulin (3.5 parts by mass) is dissolved in 500 parts by volume of an aqueous solvent composed of 50 mM TRIS, 0.1 M trisodium citrate, and 10 mg/ml phenol at pH 7.6. To this solution is added 37.5 parts of a 15.3 mM solution of zinc chloride. The acylated insulin solution and the insulin solution are combined together and stirred to insure mixing of the two solutions. This solution is filtered through a 0.22 micron, low-protein binding filter. A protamine solution is prepared by dissolving 7 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is allowed to stand for about 24 hours at room temperature (typically about 22° C.). The amorphous precipitate converts to a co-crystalline microcrystalline solid.

PREPARATION 12

1:3 Co-crystals of Human Insulin and B29-Nε-Octanoyl-human Insulin

A dry powder of B29-Nε-octanoyl-LysB29 human insulin (5.25 parts by mass) is dissolved in 750 parts by volume of an aqueous solvent composed of 50 mM TRIS, 0.1 M trisodium citrate, and 10 mg/ml phenol at pH 7.6. To this solution is added 56.25 parts of a 15.3 mM solution of zinc chloride. A second solution is prepared wherein a dry powder of human insulin (1.75 parts by mass) is dissolved in 250 parts by volume of an aqueous solvent composed of 50 mM TRIS, 0.1 M trisodium citrate, and 10 mg/ml phenol at pH 7.6. To this solution is added 18.75 parts of a 15.3 mM solution of zinc chloride. The acylated insulin solution and the insulin solution are combined together and stirred to insure mixing of the two solutions. This solution is filtered through a 0.22 micron, low-protein binding filter. A protamine solution is prepared by dissolving 7 parts by mass of protamine sulfate in 10,000 parts by volume of water then filtering through a 0.22 micron, low-protein binding filter. Equal volumes of the acylated insulin solution and of the protamine sulfate solution are combined. An amorphous precipitate forms. This suspension is allowed to stand for about 24 hours at room temperature (typically about 22° C.). The amorphous precipitate converts to a co-crystalline microcrystalline solid.

PREPARATION 13

Co-crystals of Human Insulin and B29-Nε-Hexanoyl-human Insulin

An acidic solution of B29-Nε-hexanoyl-human insulin was prepared by dissolving 12.3 mg of B29-Nε-hexanoyl-human insulin in 0.3 mL of 0.1 N HCl. An acidic solution of human insulin was prepared by dissolving 4.6 mg of human insulin (zinc crystals) in 0.1 mL of 0.1 N HCl. The two solutions were combined giving a total volume of 0.4 mL. This resulting solution was stirred for approximately 5 minutes. To this resulting solution was added, with stirring, 0.150 mL of a 1000 ppm zinc(II) solution. A crystallization diluent was prepared comprising 32 mg/mL glycerol, 50 mM tris buffer, 10 mg/mL phenol, 100 mM trisodium citrate, at a pH of 7.6. To the insulin solution was added 1.6 mL of the crystallization diluent. The pH of the solution was adjusted to 7.59 using 1 N NaOH and 1 N HCl. The solution was filtered through a 0.22 micron, low protein binding filter. A protamine solution was prepared by dissolving 7.47 mg of protamine sulfate in 10 mL of water. Two milliliters (2 mL) of the protamine solution was added to 2 mL of the insulin solution. The resulting solution was allowed to stand undisturbed for 18 hours at a controlled temperature of 25° C.

Microscopic inspection (at 18 hours) revealed that crystallization had occurred and that the preparation yielded uniform, single, rod-like crystals possessing approximate average lengths of 3 microns.

Four milliliters (4 mL) of the crystal formulation produced above after 18 hours were allowed to stand undisturbed overnight, and the crystals sedimented completely. The supernatant was then removed, and replaced with 4 mL of a diluent comprising 16 mg/mL glycerol, 20 mM tris buffer, 1.6 mg/mL m-cresol, 0.65 mg/mL phenol, 40 mM trisodium citrate, pH 7.6. The crystals were then resuspended, and allowed to sediment again. This procedure was carried out three times except that on the third occasion the supernatant was replaced with only 3 mL of diluent.

The dissolution rate of the crystals was measured by placing 0.005 mL of the uniformly suspended formulation into 3 mL of Dulbecco's phosphate buffered saline (without calcium or magnesium) in a 1 cm path length square quartz cuvette at a temperature of 22° C. This solution was stirred at a constant rate using a magnetic cuvette stirrer. Absorbance measurements at 320 nm were taken at 1 minute intervals. The absorbance at 320 nm corresponds to the light scattered by the insoluble particles present in the aqueous suspension. Consequently, as the microcrystals dissolve, the absorbance approaches zero. The time required for the 0.005 mL of this formulation to dissolve was greater than 150 minutes. The time required for dissolution of a 0.005 mL sample of U100 commercial Humulin N to dissolve when subjected to the same conditions was about 10 minutes.

The amount of total protein in the formulation was analyzed by HPLC to quantitate the total potency. The total potency refers to the total concentration of human insulin and B29-Nε-hexanoyl-human insulin. An aliquot (0.050 mL) of the fully resuspended formulation was dissolved in 0.950 mL of 0.01 N HCL, and subjected to HPLC analysis, as described below. The total potency determined from this analysis was 4.54 mg/mL.

For HPLC analyses, the following conditions were used: a C8-reversed phase column; constant 23° C.; 1.0 mL/min, detection at 214 nm; solvent A=10% acetonitrile (vol/vol) in 0.1% aqueous trifluoroacetic acid; solvent B=90% acetonitrile (vol/vol) in 0.1% aqueous trifluoroacetic acid; linear gradients (0.1 min, 0%B; 45.1 min, 75%B; 50.1 min, 100%B; 55 min 100%B; 57 min, 0%B; 72 min, 0%B). Standards were prepared by dissolving bulk insulin and bulk acyl insulin in 0.01 N HCl. The concentration of each standard was determined by UV spectroscopy. A solution of 1.0 mg/ml of human insulin in a 1 cm cuvette was assumed to have an absorbance of 1.05 optical density units at the wavelength maximum (approximately 276 nm). This corresponds to a molar extinction coefficient of 6098. Acylated insulins were assumed to have the same molar extinction coefficient as human insulin. The solutions calibrated by UV were then diluted to get standards at 0.220, 0.147, 0.073, and 0.022 mg/mL. The standards were run on HPLC and a standard curve of area vs. concentration was obtained.

The supernatant was analyzed to determine the total concentration of soluble human insulin and B29-Nε-hexanoyl-human insulin present in the formulation. To 0.040 mL of the supernatant, were added 0.160 mL of 0.01 N HCl. The acidified supernatant was analyzed by HPLC, as described above. The concentration of soluble human insulin and B29-Nε-hexanoyl-human insulin in the supernatant was determined to be 0.07 mg/mL.

The ratios of B29-Nε-hexanoyl-human insulin and human insulin in the crystal were determined by sedimenting an aliquot (0.100 mL) of the formulation using a bench-top centrifuge, decanting the supernatant, resuspending the crystals in 0.400 mL of Dulbecco's phosphate-buffered saline, recentrifuging, removing the supernatant, and finally dissolving the crystals in 1.50 mL of 0.01 N HCl. The HPLC analysis described above was performed. The result of this analysis was 84.2% B29-Nε-hexanoyl-human insulin and 15.8% human insulin.

PREPARATION 14

Co-crystal Suspension Formulation Comprising Human Insulin and B29-Nε-Decanoyl-human Insulin An acidic solution of B29-Nε-decanoyl-human insulin was prepared by dissolving 10.4 mg of B29-Nε-decanoyl-human insulin in 0.25 mL of 0.1 N HCl. An acidic solution of human insulin was prepared by dissolving 30.3 mg of human insulin (zinc crystals) in 0.75 mL of 0.1 N HCl. The two solutions were combined, giving a total volume of 1 mL. This resulting solution was stirred for approximately 5 minutes. To this solution was added, with stirring, 0.305 mL of a 1000 ppm zinc(II) solution. To the resulting solution, was added 4 mL of a crystallization diluent (40 mg/mL glycerol, 50 mM tris buffer, 4 mg/mL m-cresol, 1.625 mg/mL phenol, 100 mM trisodium citrate, pH 7.4). The pH of the resulting solution was adjusted to 7.58. This solution was filtered through a 0.22 micron, low protein binding filter. Five milliliters (5 mL) of protamine solution (37.6 mg of protamine sulfate in 50 mL of water) was added to 5 mL of the filtered solution. The resulting solution was allowed to stand undisturbed for 63 hours at a controlled temperature of 25° C.

Microscopic inspection (at 63 hours) revealed that crystallization had occurred, and that the preparation had yielded uniform, single, rod-like crystals possessing approximate average lengths of 8 microns.

The dissolution rate of the crystals was measured by placing 0.006 mL of the uniformly suspended crystal formulation into 3 mL of Dulbecco's phosphate buffered saline (without calcium or magnesium) in a 1 cm path length square quartz cuvette at a temperature of 22° C. The time required for the 0.006 mL of this crystal formulation to dissolve was greater than 300 minutes. The time required for a 0.005 mL sample of U100 commercial Humulin N to dissolve under the same conditions was about 10 minutes.

To prepare for HPLC analysis, the crystals were sedimented by allowing the formulation to stand undisturbed. Eight milliliters (8 mL) of the supernatant were then removed, and were replaced with 8 mL of a diluent [16 mg/mL glycerol, 20 mM tris buffer, 1.6 mg/mL m-cresol, 0.65 mg/mL phenol, 40 mM trisodium citrate, pH 7.6]. The co-crystals were then resuspended. This procedure was carried out in the same way three times, except that on the third occasion, the 8 mL of supernatant was replaced with 7 mL of diluent.

Potency of the crystal formulation, and in the supernatant, was analyzed by HPLC, essentially as described in Preparation 13. The total potency determined from this analysis was 3.87 mg/mL. The concentration of soluble human insulin and B29-Nε-decanoyl-human insulin in the supernatant was determined to be 0.06 mg/mL. The proportions of human insulin and B29-Nε-decanoyl-human insulin in the crystal phase were determined by the procedure of Preparation 13 to be 74.3% human insulin, and 25.7t B29-Nε-decanoyl-human insulin.

A particle sizing measurement was performed on a sample of the formulation utilizing a particle sizing instrument (Multisizer Model IIE, Coulter Corp., Miami, Fla. 33116-9015). To perform this measurement, 0.25 mL of the crystal formulation was added to 100 mL of a diluent consisting 14 mM dibasic sodium phosphate, 16 mM glycerol, 1.6 mg/mL m-cresol, 0.65 mg/mL phenol, pH 7.4. The instrument aperture tube orifice size was 50 microns. Particle size data was collected for 50 seconds. This measurement showed that the mean particle diameter of the crystals was approximately 6 microns with an approximately normal distribution encompassing a range of particle sizes from approximately 2 microns to approximately 9 microns. This result is similar to the particle size distribution of commercial NPH determined using an analogous method [DeFelippis, M. R., et al. J. Pharmaceut. Sci. 87:170–176 (1998)].

PREPARATION 15

Co-crystal Suspension Formulation Comprising Human Insulin and B29-Nε-Octanoyl-human Insulin An acidic solution of B29-Nε-octanoyl-human insulin was prepared by dissolving 30.3 mg of B29-Nε- octanoyl-human insulin in 0.75 mL of 0.1 N HCl. An acidic solution of human insulin was prepared by dissolving 59.7 mg of human insulin (zinc crystals) in 1.5 mL of 0.1 N HCl. An aliquot (0.25 mL) of the human insulin solution was combined with the 0.75 mL B29-Nε-octanoyl-human insulin solution, giving a total volume of 1 mL, which was stirred for approximately 5 minutes. To this was added, with stirring, 0.365 mL of a 1000 ppm zinc(II) solution. To the insulin plus zinc solution was added 4 mL of crystallization diluent (40 mg/mL glycerol, 35 mM sodium phosphate dibasic buffer, 4 mg/mL m-cresol, 1.625 mg/mL phenol, 15 mM trisodium citrate, pH 7.4). The pH of the resulting solution was adjusted to 7.60. The solution was filtered through a 0.22 micron, low protein binding filter. Five milliliters (5 mL) of protamine solution (37.9 mg of protamine sulfate in 50 mn of water) was added to 5 mL of the filtered insulin plus zinc solution. The resulting solution was allowed to stand undisturbed for 48 hours at a controlled temperature of 25° C.

Microscopic inspection (at 48 hours) revealed that crystallization had occurred and that the preparation had yielded uniform, single, rod-like crystals possessing approximate average lengths of 5 microns.

To prepare for HPLC analysis and dissolution testing, the crystals were sedimented by allowing the formulation to stand undisturbed. Eight milliliters (8 mL) of the supernatant were then removed and replaced with 8 mL of a diluent [16 mg/mL glycerol, 14 mM sodium phosphate dibasic buffer, 1.6 mg/mL m-cresol, 0.65 mg/mL phenol, 6 mM trisodium citrate, pH 7.6]. The crystals were then resuspended. This procedure was carried out in the same way three times, except that on the third occasion the 8 mL of supernatant was replaced with 7 mL of diluent.

The dissolution rate was determined essentially as described in Preparation 13, above. The approximate time required for 0.005 mL of the present formulation to dissolve was more than 300 minutes. The time required for a 0.005 mL sample of U100 commercial Humulin N to dissolve under the same conditions was about 10 minutes.

Total potency, and potency in the supernatant, se data clearly show that soluble B29-Nε- Preparation 13. The total potency was 3.44 mg/mL. The concentration of soluble human insulin and B29-Nε-octanoyl-human insulin in the crystal formulation was determined to be 0.01 mg/mL. The proportions of human insulin and B29-Nε-octanoyl-human insulin in the crystal phase were determined, essentially by the procedure of Preparation 13, to be 25.5% human insulin, and 74.5% B29-Nε-octanoyl-human insulin.

The mean particle diameter of the crystals, determined as described in Preparation 14, was approximately 6 microns, with an approximately normal distribution, encompassing a range of particle sizes from approximately 2 microns to approximately 12 microns. This result is similar to the particle size distribution of commercial NPH as reported in DeFelippis, M. R., et al. supra.

PREPARATION 16

Three Co-crystal Formulations Compared with an Insulin Formulation

An acidic solution of B29-Nε-octanoyl-human insulin was prepared by dissolving 24.18 mg of B29-Nε-octanoyl-human insulin in 0.6 mL of 0.1 N HCl. An acidic solution of human insulin was prepared by dissolving 41.1 mg of human insulin (as zinc crystals) in 1 mL of 0.1 N HCl. Four 0.4 mL solutions were prepared by combining different volumes of the B29-Nε-octanoyl-human insulin and human insulin solutions as indicated below in Table 4.

TABLE 4

Preparation of formulations of microcrystals

| | Formulation | | | |
|---|---|---|---|---|
| | D | C | B | A |
| Nominal Mass Percent of B29-Nε-octanoyl-human insulin | 75 | 50 | 25 | 0 |
| Volume of B29-Nε-octanoyl-human insulin solution added (μL) | 300 | 200 | 100 | 0 |
| Volume of human insulin solution added (μL) | 100 | 200 | 300 | 400 |

To each of the four 0.4 mL solutions, 0.15 mL of a 1000 ppm zinc(II) solution was added. To each of the four 0.55 mL solutions, 1.6 mL of a crystallization diluent (50 mM tris buffer, 10 mg/mL phenol, 100 mM trisodium citrate, with a pH of 7.6) were added. Each of the four solutions was adjusted to pH 7.6 with small quantities of 1 N NaOH and 0.1 N HCl. Each solution was filtered through a 0.22 micron, low protein binding filter. Two milliliters (2 mL) of each of the four protein solutions were combined with 2 mL of protamine solution (7.34 mg of protamine sulfate in 10 mL of water). In each case, a precipitate formed immediately. These four 4 mL suspensions were allowed to stand undisturbed at room temperature (approximately 22° C.) for 16 hours.

Microscopic inspection (at 16 hours) revealed that each of the four preparations had yielded uniform, single, rod-like crystals with approximate average lengths of about 10 microns.

Each 4 mL formulation was transferred to a test tube and centrifuged in a bench-top centrifuge at 3000 rpm for 20 minutes to fully sediment the crystals. For each formulation, 3 mL of the supernatant were removed and replaced with 3 mL of a diluent (25 mM tris buffer, 5 mg/mL phenol, 16 mg/mL glycerol, pH 7.4). The crystals were then resuspended. This procedure was carried out three times except that on the third occasion the 3 mL of supernatant was replaced with 2.5 mL of diluent for each formulation.

Each of the four formulations was analyzed by HPLC to quantitate the total potencies of the formulations and the compositions of the respective crystals, essentially as described above. The total potency refers to the total concentration of human insulin and B29-Nε-octanoyl-human insulin. The total potency and percentage of B29-Nε-octanoyl-human insulin were determined by analyzing an aliquot of the uniformly suspended formulation. The supernatant was analyzed to determine the total concentration of soluble human insulin and soluble B29-Nε-octanoyl-human insulin present in each formulation. The results of these analyses are presented below. Dissolution times were determined as described above in Preparation 13.

TABLE 5

Characteristics of formulations of microcrystals.

| | Formulation | | | | |
|---|---|---|---|---|---|
| | D | C | B | A | NPH |
| B29-Nε-octanoyl-human insulin in crystal (%) | 77.7 | 51.4 | 23.7 | 0 | — |
| Human insulin in crystal (%) | 22.3 | 48.6 | 76.3 | 100 | — |

TABLE 5-continued

Characteristics of formulations of microcrystals.

| | Formulation | | | | |
|---|---|---|---|---|---|
| | D | C | B | A | NPH |
| Total potency (mg/mL) | 3.21 | 3.48 | 3.38 | 3.43 | — |
| Supernatant potency (mg/mL) | <0.01 | <0.01 | <0.01 | <0.01 | — |
| Dissolution Time (min) | 300 | 120 | 50 | 20 | 10 |

PREPARATION 17

Preparation of Insoluble Compositions

The following is an outline of another method that was used to prepare precipitates and micro-crystals of the present invention. The outline is to be read together with the data in Table 6, below.

A measured mass of a derivatized protein, prepared as described herein, was dissolved in 0.6 mL of 0.1 N HCl. A measured mass of a protein was dissolved in 0.2 mL of 0.1 N HCl (zinc crystals of human insulin or LysB28, Pro29-human insulin analog). The two solutions were thoroughly mixed together by stirring for five to ten minutes. A volume (0.32 mL) of an aqueous solution containing 1000 ppm Zn(II) and a volume (3.2 mL) of a diluent solution (about 50 mM Tris reagent, about 10 mg/ mL phenol, about 16 mg/mL glycerol, and about 29.5 mg/mL trisodium citrate) were added to the mixture of the two proteins. The pH of the resulting solution was adjusted to about 7.6 (7.55–7.64) using 1 N HCl or 1 N NaOH. The pH-adjusted solution was filtered through a 0.22 micron, low-protein binding filter. To four milliliters of the filtrate was added four milliliters of a solution of protamine in water (about 37.3 mg protamine sulfate per 100 mL, range 37.18–37.48). Precipitate formed immediately upon adding the protamine solution. The preparation was allowed to stand undisturbed at 25° C. Dissolution tests were carried out as previously described. Under the same conditions, insulin NPH dissolved in about 6 minutes.

TABLE 6

Preparation of insoluble compositions.

| Protein | Lys (B28), Pro (B29)-human insulin analog | | | | |
|---|---|---|---|---|---|
| Protein mass (mg) | 4.28 | 4.02 | 3.84 | 3.96 | 4.15 |
| Derivatized protein | B29-aceylated-human insulin | | | | |
| Derivatizing group | butanoyl | pentanoyl | hexanoyl | nonanoyl | decanoyl |
| Derivatized protein mass (mg) | 11.90 | 12.1 | 12.08 | 12.13 | 12.20 |
| Crystal shape | rod-like | rod-like | rod-like | rod-like | rod-like |
| Yield (%) | >80 | >90 | >90 | >90 | >90 |
| Derivatized protein in insoluble phase (%) | 77.5 | 75.1 | 77 | 76.5 | 76.6 |
| Dissolution time (min) | 23–24 | 31 | 54 | 67 | 37–38 |

TABLE 6-continued

Preparation of insoluble compositions.

| Protein | human insulin | | | | |
|---|---|---|---|---|---|
| Protein mass | 12.09 | 12.18 | 12.12 | 12.21 | 12.27 |
| Derivatized protein | B28-acylated-Lys (B28), Pro (B29)-human insulin analog | | | A1, B28-diacylated-Lys (B28), Pro (B29)-human insulin | |
| Derivatizing group | butanoyl | hexanoyl | octanoyl | di-butanoyl | di-hexanoyl |
| Derivatized protein mass (mg) | 4.39 | 4.21 | 4.28 | 4.11 | 4.23 |
| Crystal shape | rod-like | rod-like | rod-like | rod-like | rod-like |
| Yield (%) | >80 | >90 | >90 | >90 | >90 |
| Derivatized protein in insoluble phase (%) | 27.6 | 25 | 27 | 26.8 | 24.1 |
| Dissolution time (min) | 16–17 | 10–11 | 27–28 | 10–11 | 20–21 |

| Protein | human insulin | | | | |
|---|---|---|---|---|---|
| Protein mass (mg) | 4.26 | 4.26 | 4.13 | 4.23 | 12.09 |
| Derivatized protein | B29-acylated-human insulin | | | | |
| Derivatizing group | butanoyl | pentanoyl | hexanoyl | nonanoyl | Tetra-decanoyl |
| Derivatized protein mass (mg) | 12.39 | 12.39 | 12.03 | 12.06 | 4.16 |
| Crystal shape | rod-like | rod-like | rod-like | rod-like | rod-like |
| Yield (%) | >90 | 72 | >90 | >90 | >90 |
| Derivatized protein in insoluble phase (%) | 76.3 | 76.5 | 75 | 72.5 | 25.07 |
| Dissolution time (min) | 45–46 | 62–63 | 77–78 | 77–78 | 61 |

| Protein | human insulin |
|---|---|
| Protein mass (mg) | 12.19 |
| Derivatized protein | B29-acylated-human insulin |
| Derivatizing group | hexa-decanoyl |
| Derivatized protein mass (mg) | 3.99 |
| Crystal shape | rod-like |
| Yield (%) | >90 |
| Derivatized protein in insoluble phase (%) | 24.7 |
| Dissolution time (min) | 71–72 |

The following is an outline of another method that was used to prepare precipitates and micro-crystals of the present invention. The outline is to be read together with the data in Table 7, below.

A measured mass of a derivatized protein, prepared as described herein, was dissolved in 3.2 mL of diluent solution (about 50 mM Tris reagent, about 10 mg/ mL phenol, about 16 mg/mL glycerol, and about 29.5 mg/mL trisodium citrate). A measured mass of a protein was dissolved in 0.6 mL of 0.1 N HCl (zinc crystals of human insulin or LysB28, Pro29-human insulin analog). The two solutions were thoroughly mixed together by stirring for five to ten minutes. The pH of the resulting solution was adjusted to about 7.6 (7.55–7.64) using 1 N HCl or 1 N NaOH. The pH-adjusted solution was filtered through a 0.22 micron, low-protein binding filter. To a volume of the filtrate was added an equal volume of a solution of protamine in water (about 37.3 mg protamine sulfate per 100 mL, range 37.18–37.48). Precipitate formed immediately upon adding the protamine solution. The preparation was allowed to stand undisturbed at 25° C. Dissolution tests were carried out as previously described. Under the same conditions, insulin NPH dissolved in about 6 minutes.

TABLE 7

Preparation of insoluble compositions.

| Protein | human insulin | | | | |
|---|---|---|---|---|---|
| Protein mass (mg) | 12.19 | 11.87 | 12.15 | 12.28 | 12.22 |
| Derivatized Protein | A1, B29-diacyl-human insulin | | | A1, B28-diacyl-LysB28, ProB29 human insulin | B29-acyl-AspB28 human insulin analog |
| Derivatizing group | di-octanoyl | di-nonanoyl | di-decanoyl | di-octanoyl | octanoyl |
| Derivatized protein mass (mg) | 4.29 | 4.07 | 4.06 | 4.29 | 3.98 |
| Crystal shape | rod-like | rod-like | rod-like | rod-like | rod-like |
| Yield (%) | >90 | >90 | >90 | >90 | >90 |
| Derivatized protein in insoluble phase (%) | 25.2 | 24.6 | 26.6 | 27.4 | 24.4 |
| Dissolution time (min) | 73–74 | 25 | 31–32 | 47–48 | 43–44 |

The following is an outline of another method that was used to prepare precipitates and micro-crystals of the present invention. The outline is to be read together with the data in Table 8, below.

A measured mass of a derivatized protein, prepared as described herein, was dissolved in a measured volume of 0.1 N HCl. A measured mass of a protein was dissolved in a measured volume of 0.1 N HCl (zinc crystals of human insulin or LysB28, Pro29-human insulin analog). Measured volumes of each of the two solutions were thoroughly mixed together by stirring for five to ten minutes. Measured volumes of an aqueous solution containing 1000 ppm Zn(II) and of a diluent solution (about 50 mM Tris reagent, about 10 mg/mL phenol, about 32 mg/mL glycerol, and about 30 mg/mL trisodium citrate dihydrate, pH 8.47) were added to the mixture of the two proteins. The pH of the resulting solution was adjusted to about 7.6 (7.58–7.63) using 1 N HCl or 1 N NaOH. The pH-adjusted solution was filtered through a 0.22 micron, low-protein binding filter. To two milliliters of the filtrate was added two milliliters of a solution of protamine in water (about 37.5 mg protamine sulfate per 100 mL). Precipitate formed immediately upon adding the protamine solution. The preparation was allowed to stand undisturbed at 25° C. Dissolution tests were carried out as previously described. Under the same conditions, insulin NPH dissolved in about 6 minutes.

TABLE 8

Preparation of insoluble compositions.

| Protein | human insulin | | | | |
|---|---|---|---|---|---|
| Protein mass (mg) | 11.3 | 11.3 | 33.6 | 33.6 | 16.5 |
| Volume of 0.1 N HCl | 0.57 | 0.57 | 1.68 | 1.68 | 0.83 |
| Derivatized protein | B29-acylated-human insulin | | | | |
| Derivatizing group | 2-methyhexanoyl | 2-ethylhexanoyl | 4-methyloctanoyl | 3-methyldecanoyl | dodecanoyl |
| Derivatized protein mass (mg) | 6.07 | 6.3 | 6.12 | 2.12 | 6.3 |
| Volume of 0.1 N HCl | 0.3 | 0.3 | 0.3 | 0.1 | 0.3 |
| mL of protein solution combined with mL of derivatized protein solution | 0.10 + 0.30 | 0.10 + 0.30 | 0.10 + 0.30 | 0.30 + 0.10 | 0.10 + 0.30 |
| mL 1000 ppm zinc | 0.152 | 0.152 | 0.112 | 0.096 | 0.152 |
| mL diluent added | 1.6 | 1.6 | 1.6 | 1.6 | 1.6 |
| Crystal shape | rod-like | rod-like | rod-like | rod-like | small-irregular |
| Yield (%) | >90 | >90 | | | >80 |
| Derovatized protein in insoluble phase (%) | 74.1 | 75.5 | | | 81.9 |
| Dissolution time (min) | 116 | 236 | | | 40 |

| Protein | human insulin | | | |
|---|---|---|---|---|
| Protein mass (mg) | 22.3 | 22.3 | 22.3 | 22.3 |
| Volume of 1.0 N HCl | 1.12 | 1.12 | 1.12 | 1.12 |
| Derivatized protein | B29-acylated-rabbit insulin | B29-acylated-pork insulin | B29-acylated-sheep insulin | B29-acylated beef insulin |
| Derivatizing group | octanoyl | octanoyl | hexanoyl | hexanoyl |
| Derivatized protein mass (mg) | 6.21 | 6.07 | 6.07 | 6.21 |
| Volume of 0.1 N HCl | 0.3 | 0.3 | 0.3 | 0.3 |
| mL of protein solution combined with mL of derivatized protein solution | 0.1 ± 0.3 | 0.1 ± 0.3 | 0.1 ± 0.3 | 0.1 ± 0.3 |
| mL 1000 ppm zinc | 0.152 | 0.152 | 0.152 | 0.152 |
| mL diluent added | 1.6 | 1.6 | 1.6 | 1.6 |
| Crystal shape | rod-like | rod-like | small-irregular | rod-like |

TABLE 8-continued

Preparation of insoluble compositions.

| Yield (%) | >90 | >90 | >90 | >90 |
|---|---|---|---|---|
| Derivatized protein in insoluble phase (%) | 74.6 | 74.7 | 75.4 | 75.9 |
| Dissolution time (min) | 111 | >300 | 227 | >300 |
| Protein | human insulin | | | |
| Protein mass (mg) | 33.6 | | 2.4 | 22.6 |
| Volume of 0.1 N HCl | 1.68 | | 0.1 | 1.12 |
| Derivatized protein | B29-acylated-Gly (A21), Arg (b31), Arg (B32)-human insulin analog | | B29-acylated human insulin | B29-acylated-desThr (B30)-human insulin analog |
| Derivatizing group | decanoyl | | 1,4-dichlorophenyl-thio-acetyl | octanoyl |
| Derivatized protein mass (mg) | 2.23 | | 5.1 | 6.06 |
| Volume of 0.1 N HCl | 0.1 | | 0.3 | 0.3 |
| mL of protein solution combined with mL of derivatized protein solution | 0.3 + 0.1 | | 0.1 + 0.3 | 0.1 + 0.3 |
| mL 1000 ppm zinc | 0.096 | | 0.152 | 0.152 |
| mL diluent added | 1.6* | | 1.6 | 1.6 |
| Crystal shape | rod-like | | small, irregular crystals | rod-like |
| Yield (%) | >90 | | >90 | >90 |
| Derivatized protein in insoluble phase (%) | 20.4 | | 71.8 | 74.2 |
| Dissolution time (min) | 63 | | 66 | >300 |

*2.096 mL of 37.5 mg/100 mL protamine sulfate solution were added before the diluent was added. The pH was adjusted after adding the diluent.

PREPARATION 18

Preparation of an Amorphous Suspension

A measured mass (13.84 mg of protein) of solid B28-tetradecanoyl-Lys(B28), Pro(B29) human insulin analog was dissolved in 0.375 mL of 0.1 N HCl. A measured mass of zinc human insulin (7.40 mg protein) was dissolved in 207 microliters of 0.1 N HCl. An aliquot (125 μL) of the insulin solution (containing 4.47 mg of human insulin) was added to the solution of B28-tetradecanoyl-Lys(B28), Pro(B29)-human insulin analog. A volume (180 μL) of 1000 ppm zinc and 2.0 mL of diluent (1.6 mg/mL phenol, 4 mg/mL m-cresol, 40 mg/mL glycerol, 5 mg/mL anhydrous sodium dibasic phosphate, 7.5 mg/mL trisodium phosphate dihydrate, pH 7.6) were added. The pH was increased from 5.6 to 8.0 with 100 microliters of 1N NaOH and back to 7.59 with 20 microliters of 1N HCl and 1N NaOH. The concentration of B28-tetradecanoyl-Lys(B28), Pro(B29) human insulin analog was 4.94 mg/mL and the human insulin concentration was 1.60 mg/mL. The solution was passed through a 0.22 micron, low-protein binding filter and refrigerated overnight. The next morning, the solution had no precipitate present. To 2.50 mL of the solution was added 2.88 mL of a protamine solution (0.75 mg/mL of solid protamine sulfate dissolved in water). An amorphous precipitate formed when the protamine was added.

After adding the protamine, the concentration of B28-tetradecanoyl-Lys(B28), Pro(B29) human insulin analog and human insulin in the soluble phase was again determined. Samples for HPLC analysis were prepared promptly after the protamine was added. From peak retention times, HPLC analysis showed that the insoluble material in the suspension contained protamine, B28-tetradecanoyl-Lys(B28), Pro(B29) human insulin analog, and human insulin. The concentration of B28-tetradecanoyl-Lys(B28), Pro(B29) human insulin analog in the soluble phase was 2.30 mg/mL and the concentration of human insulin was 0.74 mg/mL.

The concentrations of B28-tetradecanoyl-Lys(B28), Pro(B29) human insulin analog and human insulin in acidified samples of the suspension, supernatant, and precipitate were determined and are tabulated below. They are in reasonable agreement with expected values. Protamine concentrations were not quantitated.

TABLE 9

Preparation of insoluble compositions.

| | Concentration (mg/mL) | | |
|---|---|---|---|
| Sample | B28-tetradecanoyl-Lys(B28),Pro(B29) human insulin analog | human insulin | Mass Percent (%) |
| Suspension | 2.52 | 0.79 | 76.2 |
| Supernatant | 0.006 | 0.057 | 8.9 |
| Precipitate | 2.29 | 0.60 | 79.2 |

PREPARATION 19

Preparation of Amorphous Suspensions

The following is an outline of another method used for preparing precipitates of the present invention. The method was used to prepare formulations of amorphous precipitates of insulin with each of three derivatized proteins: B29-Nε-octanoyl-human insulin; B29-Nε-nonanoyl-human insulin; and B28-Nε-octanoyl-LysB28, ProB29-human insulin analog.

A measured mass of solid derivatized protein was dissolved in 3 mL of 0.1 N HCl to produce a solution containing approximately 16 mg/mL derivatized protein. A measured mass of zinc human insulin crystals (73 mg, of which 67.17 mg was protein) was dissolved in 4.198 mL of 0.1 N HCl to produce a solution containing approximately 16 mg/mL insulin). Three milliliters of the solution of derivatized protein and one milliliter of the insulin solution were combined and thoroughly mixed. Measured volumes of a 1000 ppm zinc solution (1.137 mL) and of a diluent (16 mL, containing, per mL: 1.625 mg phenol, 4 mg m-cresol, 40 mg glycerol, 5 mg anhydrous sodium dibasic phosphate, 7.5 mg trisodium citrate dihydrate, pH 7.6) were added. The pH was adjusted to about 7.6 (7.58–7.61) using 5 N NaOH and 5 N HCl solutions. The volume added during pH adjustment was from 0.11 to 0.12 mL. The solution was passed through a 0.22 micron, low-protein binding filter and refrigerated overnight. The next morning, the solution had no precipitate present. The solution was comprised of protein and derivatized protein (approximately a 1:3 mass ratio), and the total protein concentration was equivalent to about 85 units per milliliter. Just prior to testing in rats, equal volumes of the solution and of a solution of protamine sulfate (0.352 mg/mL) were combined and mixed thoroughly. An amorphous precipitate formed immediately. A sample of the suspension formulation containing the amorphous precipitate was promptly injected into test animals. After mixing with protamine, the concentration of total protein was about 42.4 units/ml.

PREPARATION 20

Gly(A21), Arg(B31), Arg(B32)-Human Insulin Analog

Gly(A21)Arg(B31)Arg(B32)-human insulin was obtained from an *E. coli* fermentation in which a Gly(A21)-human proinsulin precursor molecule was overexpressed into inclusion bodies. A portion (94.7 g) of inclusion bodies was solubilized in 500 mL of 6 M guanidine hydrochloride containing 0.1 M TRIS, 0.27 M sodium sulfite, and 0.1 M sodium tetrathionate, pH 10.5 at room temperature. The pH was quickly lowered to 8.8 with 12 N HCl. After vigorously stirring in an open container for 45 minutes the pH was lowered to 2.1 with phosphoric acid and the sample centrifuged overnight at 4° C. The supernatant was decanted and stored at 4° C. for additional processing. The pellet was re-extracted with 200 mL of additional pH 10.5 solution (see above) and then centrifuged for 3 hours at 4° C. This and the previously obtained supernatant were each diluted 4×with 100 mM sodium phosphate, pH 4, precipitating the product and other acidic components. After allowing the precipitate to settle, most of the supernatant was decanted and discarded. The resulting suspension was centrifuged, followed by decanting and discarding of additional supernatant, leaving wet pellets of the crude Gly(A21)-human proinsulin S-sulfonate precursor. The pellets were solubilized in 1.5 liters of 7 M deionized urea, adjusting the pH to 8 with 5 N NaOH and stirring over several hours at 4° C. Salt (NaCl) was then added to achieve 1 M concentration and the sample was loaded onto a XAD-7 column (14 cm×20 cm, Toso-Haas, Montgomeryville, Pa.), previously flushed with 50% acetonitrile/50% 50 mM ammonium bicarbonate, 10% acetonitrile/90% 50 mM ammonium bicarbonate, and finally with 7 M deionized urea/1M NaCl/20 mM TRIS, pH 8. Once loaded, the column was pumped with 4.5 liters of a 7 M deionized urea/1 M NaCl/20 mM TRIS, pH 8 solution, followed by 2.8 liters of 50 mM ammonium bicarbonate/1 M NaCl, and 6.5 liters of 50 mM ammonium bicarbonate. The column was eluted with a linear gradient of acetonitrile in 50 mM ammonium bicarbonate, while monitoring the eluant by UV at 280 nm. The peak of interest, partially purified Gly(A21)-human proinsulin S-sulfonate precursor, was collected, lyophilized, and subjected to a folding/disulfide bond procedure was dissolved in 3 liters of 20 mM glycine, pH 10.5, 4° C. Then, 15 mL of 240 mM cysteine HCl were added with stirring, while maintaining the pH at 10.5 and the temperature at 4° C. The reaction solution was stirred gently at 4° C. for 27 hours and then quenched by lowering the pH to 3.1 with phosphoric acid. Acetonitrile (155 mL) was added, and the solution was then loaded onto a 5×25 cm C4 reversed-phase column previously pumped with 60% acetonitrile/40% water/0.1% TFA and equilibrated in 10% acetonitrile/90% water/0.1% TFA. Once loaded the column was pumped with 1 liter of 17.5% acetonitrile/82.5% water/0.1% TFA, then eluted with a linear gradient of acetonitrile in 0.1% TFA while monitoring at 280 nm. Selected fractions were pooled and lyophilized with a recovery of 714 mg. For conversion of the proinsulin precursor to the desired insulin analog, 697 mg of the Gly(A21) human proinsulin precursor were dissolved in 70 mL 50 mM ammonium bicarbonate, then chilled to 4° C., pH 8.3. A volume (0.14 mL) of a 1 mg/mL solution of pork trypsin (Sigma Chemical Company, St. Louis, Mo.) in 0.01 N HCl was added to the sample solution which was stirred gently at 4° C. for about 24 hours. An additional 0.14 mL of the trypsin solution was added to the reaction solution which was then stirred for an additional 21 hours, 45 minutes. The reaction was quenched by lowering the pH to 3.2 with 0.7 mL glacial acetic acid and 0.3 mL phosphoric acid. The quenched Gly(A21)Arg(B31)Arg(B32)-human insulin sample solution from the tryptic cleavage reaction was diluted 4×with 30% acetonitrile/70% 50 mM acetic acid, pH 3.1, and loaded onto a 1×30 cm S HyperD F (Biosepra, Marlborough, Mass.) cation exchange column previously pumped with 30% acetonitrile/70% 50 mM acetic acid/500 mM NaCl, pH 3.3, and equilibrated in 30% acetonitrile/70% 50 mM acetic acid. Once loaded the column was pumped with about 50 mL of 30% acetonitrile/70% 50 mM acetic acid, then eluted with a linear gradient of NaCl in 30% acetonitrile/50 mM acetic acid while monitoring the eluant at 276 nm. Selected fractions containing the Gly(A21)Arg(B31)Arg(B32)-human insulin were pooled, diluted 3×with purified water and loaded onto a 2.2×25 cm C4 reversed-phase column (Vydac, Hesperia, Calif.) previously pumped with 60% acetonitrile/40% water/0.1% TFA, then 10% acetonitrile/90% water/0.1% TFA. Once loaded, the column was pumped with about 200 mL of 10% acetonitrile/90% water/0.1% TFA, then eluted with a linear gradient of acetonitrile in 0.1% TFA. Selected fractions were pooled and lyophilized giving a recovery of 101 mg. Analytical HPLC revealed a purity of greater that 95% main peak. Electrospray mass spectroscopy (ESMS) analysis of the purified protein yielded a molecular weight of 6062.9 (6063.0, theory).

PREPARATION 21

Des(B30)-Human Insulin

Des(B30)-human insulin was prepared from human proinsulin by controlled tryptic hydrolysis. A mass (2 g) of human proinsulin biosynthesized in recombinant *E. coli* and purified by conventional methods [Frank, B. H., et al., in *PEPTIDES: Synthesis-Structure-Function. Proceedings of the Seventh American Peptide Symposium*, Rich, D. H. and Gross, E. (Eds.), Pierce Chemical Company, Rockford, pp. 729–738, 1981; also, Frank, B. H., U.S. Pat. No. 4,430,266, issued Feb. 7, 1984, each of which is incorporated by reference] were dissolved in 400 mL of 0.1 M, pH 7.5 HEPES buffer. After addition of 8 mL of 1 M $CaCl_2$ (in water) and pH adjustment to 7.5 with 5 N NaOH, 2 mL of a 10 mg/mL solution of pork trypsin (Sigma) in 0.01 N HCl were transferred to the sample solution while gently stirring. The reaction solution was allowed to stir at ambient temperature for 2 hours and 42 minutes, at which time it was transferred to a 37° C. environment while stirring occasionally. After 1 hour and 45 minutes at 37° C. the enzymatic reaction was quenched by lowering the pH to 3.0 with phosphoric acid and the temperature to 4° C. for storage. Subsequently, the solution was brought to room temperature and diluted with 50 mL acetonitrile, then to a final volume of 500 mL with purified water, then loaded onto a 2.5×58 cm CG-161 (Toso-Haas) column previously pumped with 1 c.v. (column volume) of 40% acetonitrile/60% 0.1 M ammonium sulfate, pH 2.5, and 2 c.v. of 10% acetonitrile/90% 0.1 M ammonium sulfate, pH 2.5. Once loaded, the column was pumped with 1 c.v. of 10% acetonitrile/90% 0.1 M ammonium sulfate, pH 2.5. The column was eluted with a linear gradient of acetonitrile in 0.1 M ammonium sulfate, pH 2.5, while monitoring the eluant at 276 nm. The peak of interest, partially purified des(B30)-human insulin, was collected by pooling selected fractions. This pooled sample of partially purified des(B30)-human insulin was diluted to 1.28 liters with purified water, pH 3.5, and applied to a 1×29 cm S HyperD F (Biosepra) cation exchange column previously pumped with 1 c.v. of 30% acetonitrile/70% 0.1% TFA/0.5 M NaCl, pH 1.9, and 2 c.v. of 30% acetonitrile/70% 0.1% TFA, pH 2.3. Once loaded the column was pumped with 1 c.v. 30% acetonitrile/70% 0.1% TFA, pH 2.3, then eluted with a linear gradient of NaCl in 30% acetonitrile/70% 0.1% TFA, pH 1.9 to 2.3, while monitoring the eluant at 276 nm. Selected fractions containing the purified des(B30)-human insulin were pooled, diluted 2.5×with purified water and loaded onto a 35-c.c. C8 SepPak (Waters, Milford, Mass.) previously cleaned and primed with 2 c.v. of acetonitrile, 2 c.v. of 60% acetonitrile/40% 0.1% TFA, and 2 c.v. of 10% acetonitrile/90% 0.1% TFA. Once loaded the SepPak was flushed with 3 c.v. of 10% acetonitrile/90% 0.1% TFA and then eluted with 2 c.v. of 60% acetonitrile/40% 0.1% TFA. The lyophilized eluant yielded 500 mg. An analytical HPLC assay suggested greater than 95% main peak. Electrospray mass spectroscopy (ESMS) analysis of the purified protein yielded a molecular weight of 5706.5 (5707, theory).

PREPARATION 22

Rabbit Insulin

Rabbit Insulin was Prepared as described in Chance, R. E., et al. [*Proinsulin, Insulin, C-Peptide*, Baba, S., et al. (Eds.), *Excerpta Medica*, Amsterdam-Oxford, pp. 99–105 (1979)].

PREPARATION 23

Asp(B28)-Human Insulin Analog

Asp(B28)-human insulin was prepared and purified essentially according to the teaching of examples 31 and 32 of Chance, R. E., et al. (U.S. Pat. No. 5,700,662, issued Dec. 23,1997) which is expressly incorporated herein by reference. Des(B23–30)-human insulin [Bromer, W. W. and Chance, R. E., *Biochim. Biophys. Acta*, 133:219–223 (1967), which is incorporated herein by reference] and a synthetic octapeptide Gly-Phe-Phe-Tyr-Thr-Asp-Lys(Tfa)-Thr were condensed using trypsin-assisted semisynthesis, purified by gel filtration and reversed-phased HPLC, treated with 15% ammonium hydroxide (v/v) for four hours at ambient temperature to remove the trifluoroacetate (Tfa) blocking group from Lys(B29), purified by reversed-phase HPLC, and lyophilized.

PREPARATION 24

Syntheses of Derivatized Proteins

The following is an outline of the syntheses of certain derivatized proteins used to prepare the precipitates and microcrystals of the present invention. The outline is to be read together with the data in Table 10, below.

A measured mass of purified insulin or of an insulin analog was dissolved in a measured volume of dimethyl-sulfoxide (DMSO) with stirring. Then, a measured volume of tetramethylguanidine hydrochloride (TMG) was added and the solution mixed thoroughly. In a separate container, a measured mass of an N-acyl-succinimide (NAS) was dissolved in a measured volume of DMSO. A measured volume of the second solution was added to the first solution. The reaction was carried out at room temperature, and the progress of the reaction was monitored by analyzing samples of the reaction mixture using HPLC. The reaction was quenched by adding a measured volume of ethanolamine, and then acidifying to pH 2–3.

The reaction mixture was then subjected to purification using reversed-phase chromatography alone, or using a combination of cation exchange chromatography followed by reversed-phase chromatography. The reversed-phase purification was carried out using an FPLC® system (Pharmacia) with UV detection at 214 nm or at 280 nm, a fraction collector, 2.2×25 cm or 5×30 cm C18 column, 2.5 or 5 mL/min flow rate, at room temperature. The liquid phases were mixtures of Solution A [0.1% trifluroacetic acid (TFA) in 10:90 acetonitrile:water (vol:vol)] and Solution B [0.1% trifluroacetic acid (TFA) in 70:30 acetonitrile:water (vol:vol)] appropriate to elute and separate the species of interest. Typically, the column was equilibrated and loaded while in 100% Solution A. Then, a linear gradient to some proportion of Solution B was used to separate the reaction products adequately. Fractions containing product were pooled. The development of purification methods is within the skill of the art.

Table 10 below provides experimental data, according to the outline above, for the synthesis of the derivatized proteins that were used to prepare various embodiments of the present invention. The starting proteins were prepared as described above, or according to conventional methods. Conventional purification was used to provide highly purified starting proteins for the syntheses described below. The synthesis of insulin, insulin analogs, and proinsulin is within the skill of the art, and may be accomplished using recombinant expression, semisythesis, or solid phase synthesis followed by chain combination. The purification of synthesized proteins to a purity adequate to prepare the derivatives used in the present invention is carried out by conventional purification techniques.

Molecular weight of the purified derivatives was confirmed by mass spectrometry via electrospray mass analysis (ESMS). Assignment of the acylation site was based either on a chromatographic analysis ("HPLC"), or on an N-terminal analysis ("N-terminal"), or both.

TABLE 10

Summary of synthesis of various derivatized proteins.

| Starting protein | human insulin | human insulin | human insulin |
| --- | --- | --- | --- |
| protein mass (mg) | 141.3 | 1,080 | 120 |
| DMSO (mL) | 42 | 30 | 36 |
| TMG (µL) | 30.5 | 233 | 25.9 |
| NAS acyl chain | n-hexanoyl | n-octanoyl | n-dodecanoyl |
| Mass of NAS (mg) | 7.76 | 85.7 | 9.22 |
| Volume of DMSO (mL) | 1.0 | 1.0 | 0.701 |
| Volume of NAS solution added (mL) | 0.494 | 0.785 | 0.701 |
| Reaction time (min) | 40 | 105 | 40 |
| Ethanolamine volume (µL) | 20 | 100 | 120 |
| Total yield (%) | 40 | 33 | 36 |
| Mol. Wt. (theory) | 5906.0 | 5933.9 | 5990.0 |

TABLE 10-continued

Summary of synthesis of various derivatized proteins.

| Starting protein | human insulin | human insulin | human insulin |
|---|---|---|---|
| Mol. Wt. (ESMS) | 5906.8 | 5933.9 | 5990.0 |
| HPLC Purity (%) | 96 | 94 | 98 |
| Acylation site (HPLC) | Nε | Nε | Nε |
| Acylation site (N-terminal) | Nε | Nε | Nε |
| protein mass (mg) | 194 | 2040 | 2050 |
| DMSO (mL) | 60 | 62 | 58 |
| TMG (μL) | 41.9 | 441 | 443 |
| NAS acyl chain | n-tetradecanoyl | n-butyryl | n-hexanoyl |
| Mass of NAS (mg) | 23.4 | 269.3 | 209 |
| Volume of DMSO (mL) | 1.0 | 1.0 | 2.0 |
| Volume of NAS solution added (mL) | 0.756 | 0.29 | 1.44 |
| Reaction time (min) | 20 | 30 | 30 |
| Ethanolamine volume (μL) | 5 | 100 | 100 |
| Total yield (%) | 45 | 27* | 22 |
| Mol. Wt. (theory) | 6018.1 | 5877.8 | 5905.9 |
| Mol. Wt. (ESMS) | 6018.2 | 5877.8 | 5906.0 |
| HPLC Purity (%) | 98 | 94 | 93 |
| Acylation site (HPLC) | Nε | Nε | Nε |
| Acylation site (N-terminal) | Nε | — | — |

*purification involved first reversed-phase HPLC, then cation exchange HPLC, then reversed-phase HPLC The following is an outline of the synthesis of additional derivatized proteins. The outline is to be read together with the data in Table 11, below, to provide full synthetic schemes.

A measured mass of purified insulin or of an insulin analog was dissolved by adding to it a measured volume of 50 mM boric acid, pH 2.57. A measured volume of acetonitrile, equal to the volume of boric acid solution, was then added slowly with stirring. The 'solvent' volume is the sum of the volumes of the boric acid and acetonitrile. The pH of the solution was adjusted to between 10.2 and 10.5 using NaOH. In a separate container, a measured mass of an N-acyl-succinimide ("NAS") was dissolved in a measured volume of DMSO. A measured volume of the second solution was added to the first solution. The reaction was carried out at room temperature, the pH was maintained above 10.2 as necessary, and the progress of the reaction was monitored by analyzing samples of the reaction mixture using HPLC. The reaction was quenched by acidifying to pH 2–3. The reaction mixture was then subjected to purification using a reversed-phase chromatography system as described above.

Table 11 provides experimental data, according to the outline above, for the synthesis of the derivatized proteins that were used to prepare various embodiments of the present invention. Molecular weight of the purified derivatives was confirmed by mass spectrometry via electrospray mass analysis (ESMS). Assignment of the acylation site was based either on a chromatographic analysis ("HPLC"), or on an N-terminal analysis ("N-terminal"), or both.

TABLE 11

Summary of synthesis of various derivatized proteins.

| Starting protein | human insulin | human insulin | human insulin |
|---|---|---|---|
| protein mass (mg) | 2,170 | 2,420 | 2,250 |
| solvent (mL) | 200 | 240 | 200 |
| NAS acyl chain | n-butyryl | n-pentanoyl | n-octanoyl |
| Mass of N-acyl-succinimide (mg) | 108.7 | 1155 | 173 |
| Volume of DMSO (mL) | 1.0 | 5 | 1.0 |
| Volume of NAS solution added (mL) | 0.955 | 0.719 | 0.81 |
| Reaction time (min) | 40 | 40 | 40 |
| Total yield (%) | 25 | 12 | 31 |
| Mol. Wt. (theory) | 5877.8 | 5891.8 | 5933.9 |
| Mol. Wt. (ESMS) | 5877.7 | 5891.9 | 5933.8 |
| HPLC Purity (%) | 96 | 95 | 96 |
| Acylation site (HPLC) | Nε | Nε | Nε |
| protein mass (mg) | 1,960 | 2,750 | 1,040 |
| solvent (mL) | 200 | 200 | 200 |
| NAS acyl chain | n-nonanoyl | n-dodecanoyl | n-tetradecanoyl |
| Mass of N-acyl-succinimide (mg) | 145.8 | 19.9 | 102.3 |
| Volume of DMSO (mL) | 1.0 | 1.0 | 1.0 |
| Volume of NAS solution added (mL) | 0.887 | 0.711 | 0.885 |
| Reaction time (min) | 40 | 30 | 35 |
| Total yield (%) | 35 | 14 | 39 |
| Mol. Wt. (theory) | 5947.9 | 5990.0 | 6018.1 |
| Mol. Wt. (ESMS) | 5948.1 | 5989.9 | 6018.1 |
| HPLC Purity (%) | 94 | 93 | 94 |
| Acylation site (HPLC) | Nε | Nε | Nε |

| Starting protein | sheep insulin | beef insulin | pork insulin |
|---|---|---|---|
| protein mass | 312 | 275 | 200 |
| solvent (mL) | 100 | 100 | 100 |
| NAS acyl chain | n-hexanoyl | n-hexanoyl | n-octanoyl |
| Mass of N-acyl-succinimide (mg) | 27.2 | 19.9 | 16.4 |
| Volume of DMSO (mL) | 1.0 | 1.0 | 1.0 |
| volume of NAS solution added (mL) | 0.644 | 0.771 | 0.764 |
| Reaction time (min) | 45 | 30 | 82 |
| Total yield (%) | 31 | 50 | 41 |
| Mol. Wt. (theory) | 5801.7 | 5831.8 | 5903.9 |
| Mol. Wt. (ms) | 5801.8 | 5831.7 | 5903.9 |
| HPLC Purity (%) | 96 | 96 | 96 |
| Acylation site (HPLC) | Nε | Nε | Nε |

| Starting protein | rabbit insulin | des(B30)-human insulin | AspB28-human insulin |
|---|---|---|---|
| Protein mass (mg) | 211.4 | 205.3 | 132.3 |
| Solvent (mL) | 100 | 20 | 20 |
| NAS acyl chain | n-octanoyl | n-octanoyl | n-octanoyl |
| Mass of N-acyl-succinimide (mg) | 16.8 | 21.5 | 11.5 |
| Volume of DMSO (mL) | 1.0 | 0.5 | 1.0 |
| Volume of NAS solution added (mL) | 0.786 | 0.303 | 0.715 |
| Reaction time (min) | 57 | 40 | 85 |
| Total yield (%) | 39 | 47 | 32 |
| Mol. Wt. (theory) | 5919.9 | 5833.6 | 5951.9 |
| Mol. Wt. (ms) | 5920.0 | 5832.1 | 5952.2 |
| HPLC Purity (%) | 95 | 96 | 94 |
| Acylation site (HPLC) | Nε | Nε | Nε |

TABLE 11-continued

Summary of synthesis of various derivatized proteins.

| Starting protein | GlyA21, ArgB31, ArgB32-human insulin analog | human insulin | des(B27)-human insulin analog |
|---|---|---|---|
| Protein mass (mg) | 86.2 | 134.8 | 44.8 |
| Solvent (mL) | 10 | 20 | 7 |
| NAS acyl chain | n-octanoyl | 2-methyl-hexanoyl | n-octanoyl |
| Mass of N-acyl-succinimide (mg) | 22.4 | 749 | 3.6 |
| Volume of DMSO (mL) | 0.5 | 4.93* | 1.0 |
| Volume of NAS solution added (mL) | 0.115 | 0.052 | 0.993 |
| Reaction time (min) | 40 | 45 | 40 |
| Total yield (%) | 45 | 45 | 53 |
| Mol. Wt. (theory) | 6189.2 | 5919.9 | 5832.8 |
| Mol. Wt. (ms) | 6189.2 | 5919.9 | 5832.9 |
| HPLC Purity (%) | 97 | 96 | 93 |
| Acylation site (HPLC) | Nε | Nε | Nε |

| Starting protein | human insulin | human insulin | human insulin |
|---|---|---|---|
| Protein mass (mg) | 160 | 147.1 | 2,080 |
| Solvent (mL) | 20 | 20 | 200 |
| NAS acyl chain | 4-methyl-octanoyl | 3-methyl-decanoyl | n-octanoyl |
| Mass of N-acyl-succinimide (mg) | 715 | 22.5 | 146.7 |
| Volume of DMSO (mL) | 4.97* | 1.0* | 1.0* |
| Volume of NAS solution added (mL) | 0.0734 | 0.609 | 0.884 |
| Reaction time (min) | 60 | 45 | 40 |
| Total yield (%) | 54 | 38 | 5.3** |
| Mol. Wt. (theory) | 5947.9 | 5976.0 | 6060.1 |
| Mol. Wt. (ms)*** | 5947.8 | 5976.2 | 6060.5 |
| HPLC Purity (%) | 96 | 96 | 92 |
| Acylation site (HPLC) | Nε | Nε | A1-Nα, Nε |

| Starting protein | des(B30)-human insulin analog | human insulin | human insulin |
|---|---|---|---|
| Protein mass (mg) | 205.3 | 1,960 | 2,110 |
| Solvent (mL) | 20 | 200 | 200 |
| NAS acyl chain | n-octanoyl | n-nonanoyl | n-decanoyl |
| Mass of N-acyl-succinimide (mg) | 21.5 | 145.8 | 150.5 |
| Volume of DMSO (mL) | 0.5 | 1.0 | 1.0 |
| Volume of NAS solution added (mL) | 0.089 | 0.0887 | 0.975 |
| Reaction time (min) | 40 | 40 | 60 |
| Total yield (%) | 11.0 | 11.5 | 11.1 |
| Mol. Wt. (theory) | 5959.5 | 6088.2 | 6116.2 |
| Mol. Wt. (ms) | 5959.3 | 6088.3 | 6116.4 |
| HPLC Purity (%) | 96 | 92 | 92 |
| Acylation site (HPLC) | A1-Nα, Nε | A1-Nα, Nε | A1-Nα, Nε |

*Dissolved in acetonitrile instead of DMSO.
**Yield of the A1-Nα,B29-Nε-diacyl-human insulin derivative
***Determined by Matrix-Assisted Laser Desorption Ionization (MALDI) mass spectroscopy instead of electrospray mass spectroscopy The following is a general outline of a synthetic scheme to produce additional derivatized proteins. In a specific instance, the outline is to be read together with the data in Table 12, below, to a provide full synthetic scheme for a particular derivatized protein. A measured mass of purified insulin or insulin analog was dissolved by adding to it a measured volume DMSO. The pH of the solution was adjusted with 10 equivalents of tetramethylguanidine. In a separate container, a measured mass of an N-acyl-succinimide ("NASO") was dissolved in a measured volume of DMSO. A measured volume of the second solution was added to the first solution to provide a 1.9 fold molar excess of N-acyl-succinimide. The reaction was carried out at room temperature and the progress of the reaction was monitored by analyzing samples of the reaction mixture using HPLC. The reaction was quenched with 20 microliters of ethanolamine, chilled in ice/water bath and diluted 2.1 times with 0.1N HCl. The reaction mixture was then subjected to desalting on reversed phase chromatography column using the following protocol: 1) the column was wetted with 100% acetonitrile, then was washed using three to four column volumes of 0.1% TFA/70% acetonitrile (Buffer B); and finally was washed using four to five column volumes of 0.1% TFA/10% acetonitrile (Buffer A); 2) diluted reaction mixtures were loaded, and the column was again washed with five to six column volumes of Buffer A; and 3) the derivatized protein was eluted by passing five to six column volumes of Buffer B through the column. The fluid collected during elution was frozen, then lyophilized. The lyophilized crude product (86.1 mg) was then subjected to re-purification using a reversed-phase chromatography system as described above.

Table 12 provides experimental data, according to the outline above, for the synthesis of the derivatized proteins that were used to prepare various embodiments of the present invention. Molecular weight of the purified derivatives was confirmed by mass spectrometry via electrospray mass analysis (ESMS). Assignment of the acylation site was based either on a chromatographic analysis ("HPLC").

TABLE 12

Summary of synthesis of various derivatized proteins.

| Starting protein | Human Insulin |
|---|---|
| protein mass (mg) | 179 |
| DMSO to dissolve human insulin (mL) | 20 |
| NAS acyl chain | 1,4-dichlorophenylthio-acetyl |
| Mass of N-acyl-succinimide (mg) | 30 |
| Volume of DMSO (mL) | 1.0 |
| Volume of NAS solution added (mL) | 0.412 |
| Reaction time (min) | 50 |
| Total yield (%) | 32.2* |
| Mol. Wt. (theory) | 6026.78 |
| Mol. Wt. (ESMS) | 6026.9 |
| HPLC Purity (%) | 96 |
| Acylation site (HPLC) | Nε |

*Yield calculate based on the desalted and lyophilized crude product weight.

EXPERIMENT 1

Time Action of Co-crystals in Dogs

The time-action of three co-crystal compositions of the present invention was determined in normal dogs that received a constant infusion of somatostatin to create a transient diabetic state. The first co-crystal formulation, comprising human insulin and B29-Nε-octanoyl-human insulin, was prepared essentially as described for Formulation D in Preparation 16 above, and was administered subcutaneously at a dose of 3 nmol/kg ("8753"). The second co-crystal formulation, comprising human insulin and B29-Nε-octanoyl-human insulin, was prepared as described for Formulation D in Preparation 16 above, and was administered subcutaneously at a dose of 2.5 nmol/kg ("8752.5"). Finally, a third co-crystal formulation, comprising human insulin and B29-Nε-decanoyl-human insulin, was prepared as described in Preparation 14 above, and was administered subcutaneously at a dose of 2.5 nmol/kg ("10252.5"). The data were compared to that observed in the same model after administration of Humulin N (2.0 nmol/kg "NPH"), Beef/Pork Ultratlente insulin (3 nmol/kg, "BP-UL"), and saline.

Experiments were conducted in overnight-fasted, chronically cannulated, conscious male and female beagles weighing 10–17 kg (Marshall Farms, North Rose, N.Y.). At least ten days prior to the study, animals were anesthetized with isoflurane (Anaquest, Madison, Wiss.), and silicone catheters attached to vascular access ports (V-A-P™, Access Technologies, Norfolk Medical, Skokie, Ill.) were inserted into the femoral artery and femoral vein. The catheters were filled with a glycerol/heparin solution (3:1, v/v; final heparin concentration of 250 KIU/ml; glycerol from Sigma Chemical Co., St. Louis, Mo., and heparin from Elkins-Sinn, Inc., Cherry Hill, N.J.) to prevent catheter occlusion, and the wounds were closed. Kefzol (Eli Lilly & Co., Indianapolis, Ind.) was administered pre-operatively (20 mg/kg, IV and 20 mg/kg, I.M.), and Keflex was administered post-operatively (250 mg, p.o. once daily for seven days) to prevent infections. Torbugesic (1.5 mg/kg, I.M.) was administered post-operatively to control pain.

Blood was drawn just prior to the study day to determine the health of the animal. Only animals with hematocrits above 38% and leukocyte counts below 16,000/mm$^3$ were used (hematology analyzer: Cell-Dyn 900, Sequoia-Turner, Mountain View, Calif.).

The morning of the experiment, the ports were accessed (Access Technologies, Norfolk Medical, Skokie, Ill.); the contents of the catheters were aspirated; the catheters were flushed with saline (Baxter Healthcare Corp., Deerfield, Ill.); the dog was placed in a cage; and extension lines (protected by a stainless steel tether and attached to a swivel system [Instech Laboratories, Plymouth Meeting, Pa.]) were attached to the port access lines.

Dogs were allowed at least 10 minutes to acclimate to the cage environment before an arterial blood sample was drawn for determination of fasting insulin, glucose, and glucagon concentrations (time=−30 minutes). At this time, a continuous, IV infusion of cyclic somatostatin (0.65 μg/kg/min; BACHEM Calif., Torrance, Calif.) was initiated and continued for the next 30.5 hours. Thirty minutes after the start of infusion (time=0 minutes), an arterial blood sample was drawn, and a subcutaneous bolus of test substance, or vehicle, was injected in the dorsal aspect of the neck. Arterial blood samples were taken every 3 hours thereafter for the determination of plasma glucose and insulin concentrations and every 6 hours for determination of plasma glucagon concentrations. The entire study lasted 30 hours.

Arterial blood samples were collected in vacuum blood collection tubes containing disodium EDTA (Terumo Medical Corp., Elkton, Md.) and immediately placed on ice. A portion of the blood sample (1.5 ml) was transferred to a polypropylene tube containing 40 μl of aprotinin (10,000 KIU/ml; Trasylol, Miles, Inc., Diagnostics Division, Kankakee, Ill.) in preparation for the determination of the plasma glucagon concentration. The samples were centrifuged, and the resulting plasma was transferred to polypropylene test tubes and stored on ice for the duration of the study.

Plasma glucose concentrations were determined the day of the study using a glucose oxidase with a commercial glucose analyzer. Samples for other assays were stored at −80° C. until time for analysis. Insulin concentrations were determined using a double antibody radioimmunoassay. Glucagon concentrations were determined using a radioimmunoassay kit (LINCO Research, Inc., St. Charles, Mo.).

At the conclusion of the experiment, the catheters were flushed with fresh saline, treated with Kefzol (20 mg/kg), and filled with the glycerol/heparin mixture; antibiotic (Keflex; 250 mg) was administered p.o. To minimize the number of animals being used and to allow pairing of the data base when possible, animals were studied multiple times. Experiments in animals being restudied were carried out a minimum of one week apart.

The 1:3 Co-crystal of human insulin and B29-Nε-octanoyl-human insulin had a time-action 9 hours longer than NPH human insulin (24 hours vs. 15 hours) for the higher dose (8753), and a time-action 6 hours longer than NPH human insulin (21 hours vs. 15 hours) for the lower dose (8752.5). The time-action was determined by statistically comparing the mean glucose levels with those of the control group (saline). The glucose profiles for the 1:3 Co-crystal formulations of human insulin and B29-Nε-octanoyl-human insulin were more like that expected of a basal insulin than was the profile for NPH-human insulin. The 1:3 Co-crystals also had greater activity and a more desirable glucose profile than did Beef/Pork Ultralente insulin. The reduction in blood glucose, compared with the control (saline), that the co-crystal formulations caused persisted longer than that caused by this Beef/Pork Ultralente insulin.

The 3:1 Co-crystal formulation of human insulin and B29-Nε-decanoyl-human insulin (10252.5) had a time-action 9 hours longer than NPH human insulin (24 hours vs. 15 hours). The difference was significant statistically ($p<0.05$). In the same animals, the 3:1 Co-crystal formulation of human insulin and B29-Nε-decanoyl-human insulin (2.5 nmol/kg, SC) had a time-action 6 hours longer than either Humulin U or Beef U preparations (24 hours vs.18 hours). The differences were also significant statistically ($p<0.05$). The glucose profile for the co-crystal formulations was more like that expected of a basal insulin than was the profile for NPH-human insulin. Furthermore, the variability in time-action among the dogs was the least when the 3:1 Co-crystal was administered.

In conclusion, these data demonstrate that the co-crystals of the present invention are effective for controlling glucose levels for protracted periods of time in dogs. They also support a conclusion that the co-crystals of the present invention will be effective for overnight glucose control of patients with type 2 diabetes or as the basal arm of basal/bolus insulin therapy for patients with type 1 or type 2 diabetes. They also suggest that these preparations may produce less variable responses than commercially available insulin preparations.

EXPERIMENT 2

Time Action of Co-crystals in Pigs

Studies were performed on normal, conscious female pigs weighing 17–25 kg. An arterial (carotid or femoral) catheter was surgically pre-implanted for sampling along with jugular venous lines for the administration of somatostatin. Prior to experiments, the cannulated pigs were fasted 22–24 hours. Subcutaneous insulin injections were given in the soft skin behind the ear at a dosage of 3.0 nmol/kg (0.5 unit/kg). Somatostatin was administered concurrently at 0.3 µg/kg/min (dissolved in 0.9% NaCl containing 1% human serum albumin, Miles Canada, Etobicoke, ON) to suppress endogenous insulin secretion. Near normoglycemia was maintained by infusing 20% dextrose at a variable rate, with frequent monitoring of glucose concentrations. The plasma glucose levels were determined on fresh plasma samples the day of the study using a glucose oxidase method with a commercial glucose analyzer.

In a euglycemic clamp study, a formulation of the present microcrystals comprised of 1:3 insulin:B29-Nε-octanoyl-human insulin was administered subcutaneously at a dose of 0.5 U/kg (equivalent to about 3 nmol/kg) at the start of the study (time 0) to five pigs. The rate of glucose infusion required to maintain euglycemia (set point=about 90 mg/dL) was determined continuously. A control group received Humulin N (U100) by subcutaneous administration at the same dose (n=6). A concomitant infusion of somatostatin (0.3 pg/kg/min) was maintained for the entire duration of the experiment. For the microcrystals of the present invention, the glucose infusion rate increased steadily over the first two hours, reaching a maximum of about 7 mg/kg/min. From then, until about 17.5 hours, the glucose infusion rate decreased fairly steadily to about 0.5 mg/kg/min. For most of the time between 17.5 hours and the end of the study at 24 hours, the glucose infusion rate remained between about 0.5 and about 2 mg/kg/min.

By contrast, the mean glucose infusion rate in the control group (Humulin NPH) increased steadily, reaching a maximum of about 14 mg/kg/min at about 3 hours after administration. Thereafter, the infusion rate decreased to about 7 mg/kg/min by about 4.5 hours, and to about 5 mg/kg/min by 13 hours after administration. No further data were taken for the control group. These results are consistent with a conclusion that the microcrystalline formulation comprised of insulin and B29-Nε-octanoyl-human insulin in a 1:3 molar ratio has a flatter glucodynamic profile than does insulin NPH.

EXPERIMENT 3

Time Action of Co-crystals in Rats

A formulation of the present microcrystals comprised of 1:3 insulin:B29-Nε-octanoyl-human insulin was tested in BBDP/Wor rats, a genetically-characterized animal model, maintained by, and available from, the University of Massachusetts Medical Center (Worchester, Mass.) in connection with Biomedical Research Models, Inc. (Rutland, Mass.). The DPBB/Wor rat line is diabetes-prone, and exhibits insulin-dependent (autoimmune) diabetes mellitus. All preparations were administered subcutaneously at a dose of 0.9 U/100 g body weight.

Male BBDP/Wor rats, aged 4–5 months and maintained on a long-acting insulin (PZI), were randomly assigned to five experimental groups, A, B, C, D and E. Group A (n=22) was treated for three days with a U40 human insulin ultralente (Humulin UL); group B (n=18) was treated for 3 days with a U40 preparation of Iletin Ultralente (65% beef insulin, 35% pork insulin); group C (n=10) was treated for three days with a formulation of microcrystals comprised of 1:3 insulin:B29-Nε-octanoyl-human insulin, prepared as described above; group D (n=21) was treated with a formulation of microcrystals comprised of 100% B29-Nε-octanoyl-human insulin; and group E received U40 beef-pork PZI insulin (PZI). Each rat was given daily injections of its group's formulation for the two days before blood glucose was determined, and on the day that the blood glucose was determined.

Blood was obtained half an hour before administering the test formulations. Samples of the formulations were injected at 11:30 A.M. Blood was obtained by nicking the tail (not anaesthetized). The samples were stored briefly on ice, then were centrifuged, and glucose determined using a Beckman II glucose analyzer. Blood 10 samples were obtained just prior to administering the test formulations, and at 2, 4, 6, 8, 12, 16, 20, and 24 hours after administration. Considering adequate control to be indicated by blood glucose levels less than 200 mg/dL, the preparations provided about 9.5 hours (Humulin UL), about 12 hours (Iletin U), about 15.5 hours (the present invention), about 20.5 hours (100% B29-Nε-octanoyl-human insulin), and about 21.5 hours (PZI) of control. Therefore, the microcrystal formulation of the present invention controlled blood glucose longer than both Humulin UL and Iletin U and 20 for a shorter period of time than did either the 100% B29-Nε-octanoyl-human insulin microcrystal preparation or the PZI preparation.

EXPERIMENT 4

Time Actions of Amorphous Precipitates in Rats

Formulations of amorphous precipitates comprised of 1:3 insulin:

B29-Nε-octanoyl-human insulin, 1:3 insulin:B28-Nε-octanoyl-Lys(B28), Pro(B29)-human insulin, and 1:3 insulin:B29-Nε-nonanoyl-human insulin, prepared as described in Preparation 19, were tested in BBDP/Wor rats. All preparations were administered subcutaneously at a dose of 0.9 U1100 g body weight.

Male BBDP/Wor rats, aged 4–5 months and maintained on a long-acting insulin (PZI), were randomly assigned to 35 five experimental groups, A, B, C, D, and E. Group A (n=7) was treated with a preparation of U40 NPH (Humulin N). Group B (n=8) was treated with a U42.4 preparation of 1:3 insulin:

B29-Nε-octanoyl-human insulin. Group C (n=8) was treated with a U42.6 preparation of 1:3 insulin:B28-Nε-octanoyl-Lys(B28), Pro (B29)-human insulin. Group D(n=8) was treated with a U42.7 preparation of 1:3 insulin:B29-Nε-nonanoyl-human insulin. Group E was treated with U40 beef-pork PZI insulin (PZI).

Blood was obtained half an hour before administering the test formulations. Animals were injected subcutaneously (0.9 U/100 g body weight) at 11:30 A.M. Blood was obtained by nicking the tail (not anaesthetized). The samples were stored briefly on ice, then centrifuged, and glucose was determined using a commercial glucose analyzer. Blood samples were obtained just prior to administering the test formulations, and at 2, 4, 6, 8, 10, 12, 14, 16, 18, 20, 22, and 24 hours after administration. Considering adequate control to be indicated by blood glucose levels less than 200 mg/dL, the preparations provided about 7.5 hours (1:3 insulin:B28-Nε-octanoyl-Lys(B28), Pro(B29)-human insulin), about 9 hours (NPH), about 15.5 hours (1:3 insulin:B29-Nε-octanoyl-human insulin), about 16 hours (1:3 insulin:B29-Nε-nonanoyl-human insulin) and about 22.5 hours (PZI) of control.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

I claim:

1. An insoluble composition, comprising:
   a) a protein selected from the group consisting of insulin, insulin analog, and proinsulin;
   b) a derivatized protein selected from the group consisting of fatty acid-acylated insulin, fatty acid-acylated insulin analogs, and fatty acid acylated proinsulins;
   c) a complexing compound;
   d) a hexamer-stabilizing compound; and
   e) a divalent metal cation.

2. The composition of claim 1, wherein the complexing compound is protamine, the hexamer-stabilizing compound is a phenolic preservative, and the divalent metal cation is zinc.

3. The composition of claim 1, wherein the derivatized protein is selected from the group consisting of fatty acid-acylated insulin and fatty acid-acylated insulin analogs.

4. The composition of claim 3, wherein the complexing compound is protamine, the hexamer-stabilizing compound is a phenolic preservative, and the divalent metal cation is zinc.

5. The composition of claim 1, wherein the derivatized protein is mono-acylated at its Lys-Nε-amino group.

6. The composition of claim 5, wherein the complexing compound is protamine, which is present at about 0.15 mg to about 0.5 mg per 3.5 mg of total protein.

7. The composition of claim 6, wherein the divalent metal cation is zinc, which is present at about 0.3 mole to about 0.7 mole per mole of total protein.

8. The composition of claim 7, wherein the hexamer-stabilizing compound is a phenolic preservative selected from the group consisting of phenol, m-cresol, o-cresol, p-cresol, chlorocresol, methylparaben, and mixtures thereof, and is present at a ratio of at least 3 moles of phenolic preservative to 6 moles of total protein.

9. The composition of claim 8, wherein the protein is selected from the group consisting of insulin and insulin analogs.

10. The composition of claim 9, wherein the protein is insulin.

11. The composition of claim 10, wherein the derivatized protein is insulin that is mono-acylated at the LysB29-Nε-amino group.

12. The composition of claim 11, wherein the derivatized protein is insulin that is acylated with a straight-chain, saturated fatty acid.

13. The composition of claim 12, wherein the straight-chain, saturated fatty acid is selected from the group consisting of n-hexanoic acid, n-heptanoic acid, n-octanoic acid, n-nonanoic acid, and n-decanoic acid.

14. The composition of claim 13, wherein the mole ratio between the protein and the derivatized protein is from about 1:9 to about 9:1.

15. The composition of claim 14, wherein the straight-chain, saturated fatty acid is selected from the group consisting of n-hexanoic acid, n-octanoic acid, and n-decanoic acid.

16. The composition of claim 15, wherein the straight-chain, saturated fatty acid is selected from the group consisting of n-octanoic acid and n-decanoic acid.

17. The composition of claim 16, wherein the straight-chain, saturated fatty acid is n-octanoic acid.

18. The composition of claim 17, wherein the mole ratio between the protein and the derivatized protein is from about 1:3 to about 3:1.

19. The composition of claim 15, wherein the mole ratio between the protein and the derivatized protein is from about 1:9 to about 1:1.

20. The composition of claim 9, wherein the protein is an insulin analog.

21. The composition of claim 20, wherein the protein is LysB28, ProB29-human insulin analog.

22. The composition of claim 20, wherein the protein is AspB28-human insulin analog.

23. The composition of claim 1, wherein the protein is insulin or an insulin analog, and the derivatized protein is a fatty acid-acylated protein selected from the group consisting of fatty acid-acylated insulin and fatty acid-acylated insulin analogs.

24. The composition of claim 1, wherein the derivatized protein is insulin that is mono-acylated at its LysB29-Nε amino group with a straight-chain, saturated fatty acid.

25. The composition of claim 24, wherein the straight-chain, saturated fatty acid is selected from the group consisting of n-hexanoic acid, n-heptanoic acid, n-octanoic acid, n-nonanoic acid, and n-decanoic acid.

26. The composition of claim 25, wherein the derivatized protein is selected from the group consisting of B29-Nε-hexanoyl-human insulin, B29-Nε-octanoyl-human insulin, and B29-Nε-decanoyl-human insulin.

27. The composition of claim 24, wherein the straight-chain, saturated fatty acid selected from the group consisting of n-dodecanoic acid, n-tetradeccanoic acid, and n-hexadecanoic acid.

28. The composition of claim 1, wherein the derivatized protein is di-acylated at the Lys-Nε-amino group and is also acylated at one N-terminal Nα-amino group, and wherein the fatty acid is selected from the group consisting of n-hexanoic acid, n-heptanoic acid, n-octanoic acid, n-nonanoic acid, and n-decanoic acid.

29. The composition of claim 1, wherein the derivatized protein is acylated with a branched-chain, saturated fatty acid.

30. The composition of claim 29, wherein the derivatized protein is acylated with a branched-chain, saturated fatty acid having from three to ten carbon atoms in its longest branch.

31. The composition of claim 1, wherein the derivatized protein is an insulin analog that is mono-acylated at its Lys-Nε-amino group with a straight-chain, saturated fatty acid.

32. The composition of claim 31 wherein the fatty acid is selected from the group consisting of n-hexanoic acid, n-heptanoic acid, n-octanoic acid, n-nonanoic acid, and n-decanoic acid.

33. The composition of claim 31, wherein the derivatized protein is an insulin analog that is mono-acylated at the Nε-amino group with a fatty acid selected from the group consisting of n-dodecanoic acid, n-tetradecanoic acid, and n-hexadecanoic acid.

34. The composition of claim 31, wherein the derivatized protein is selected from the group consisting of fatty acid-acylated animal insulins, fatty acid-acylated monomeric insulin analogs, fatty acid-acylated deletion analogs, and fatty acid-acylated pi-shifted insulin analogs.

35. The composition of claim 34, wherein the derivatized protein is fatty acid-acylated des(B30)-human insulin analog, fatty acid-acylated LysB28, ProB29-human insulin analog, or fatty acid-acylated AspB28-human insulin analog.

36. The composition of claim 35, wherein the derivatized protein is fatty acid-acylated des(B30)-human insulin analog.

37. The composition of claim 36, wherein the derivatized protein is B29-Nε-myristoyl-des(B30)-human insulin analog.

38. The composition of claim 35, wherein the derivatized protein is fatty acid-acylated LysB28, ProB29-human insulin analog.

39. The composition of claim 38, wherein the derivatized protein is B28-Nε-myristoyl-LysB28, ProB29-human insulin analog.

40. The composition of claim 35, wherein the derivatized protein is fatty acid-acylated AspB28-human insulin analog.

41. The composition of claim 6, wherein the mole ratio between the protein and the derivatized protein is from about 1:9 to about 9:1.

42. The composition of claim 41, wherein the ratio is from about 1:3 to about 3:1.

43. The composition of claim 41, wherein the ratio is from about 1:9 to about 1:1.

44. The composition of claim 1, wherein the protein is insulin.

45. The composition of claim 1, wherein the protein is an insulin analog.

46. The composition of claim 45, wherein the protein is a monomeric insulin analog.

47. The composition of claim 20, wherein the protein is GlyA21, ArgB31, Arg B32 human insulin analog.

* * * * *

UNITED STATES PATENT AND TRADEMARK OFFICE
CERTIFICATE OF CORRECTION

PATENT NO. : 6,531,448 B1
DATED : March 11, 2003
INVENTOR(S) : Mark Laurence Brader It is certified that error appears in the above-identified patent and that said Letters Patent is hereby corrected as shown below:

<u>Column 68,</u>
Line 33, delete "n-tetradeccanoic" and insert -- n-tetradecanoic --.
Line 65, delete "pi-shifted" and insert -- pI-shifted --.

<u>Column 70,</u>
Line 1, delete "claim 6" and insert -- claim 1 --.

Signed and Sealed this

Fourteenth Day of October, 2003

JAMES E. ROGAN
*Director of the United States Patent and Trademark Office*